US009932300B2

(12) United States Patent
Aktas et al.

(10) Patent No.: US 9,932,300 B2
(45) Date of Patent: Apr. 3, 2018

(54) N,N'-DIARYLUREA COMPOUNDS AND N,N'-DIARYLTHIOUREA COMPOUNDS AS INHIBITORS OF TRANSLATION INITIATION

(71) Applicant: President and Fellows of Harvard College, Cambridge, MA (US)

(72) Inventors: Bertal Huseyin Aktas, Newton, MA (US); José A. Halperin, Brookline, MA (US); Michael Chorev, Chestnut Hill, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/216,057

(22) Filed: Jul. 21, 2016

(65) Prior Publication Data
US 2016/0318857 A1 Nov. 3, 2016

Related U.S. Application Data

(62) Division of application No. 13/322,607, filed as application No. PCT/US2010/036584 on May 28, 2010, now Pat. No. 9,421,211.

(60) Provisional application No. 61/181,920, filed on May 28, 2009.

(51) Int. Cl.
| | | |
|---|---|---|
| *A61K 31/519* | (2006.01) | |
| *C07C 275/30* | (2006.01) | |
| *A61K 31/5377* | (2006.01) | |
| *C07D 213/75* | (2006.01) | |
| *C07D 249/14* | (2006.01) | |
| *C07C 275/34* | (2006.01) | |
| *C07C 275/38* | (2006.01) | |
| *C07C 275/40* | (2006.01) | |
| *C07D 213/81* | (2006.01) | |
| *C07D 215/06* | (2006.01) | |
| *C07D 231/56* | (2006.01) | |
| *C07D 233/36* | (2006.01) | |
| *C07D 237/30* | (2006.01) | |
| *C07D 239/34* | (2006.01) | |
| *C07D 239/42* | (2006.01) | |
| *C07D 261/14* | (2006.01) | |
| *C07D 271/12* | (2006.01) | |
| *C07D 277/18* | (2006.01) | |
| *C07D 277/66* | (2006.01) | |
| *C07D 285/14* | (2006.01) | |
(Continued)

(52) U.S. Cl.
CPC ........ *C07C 275/30* (2013.01); *A61K 31/5377* (2013.01); *C07C 275/34* (2013.01); *C07C 275/38* (2013.01); *C07C 275/40* (2013.01); *C07D 213/75* (2013.01); *C07D 213/81* (2013.01); *C07D 215/06* (2013.01); *C07D 231/56* (2013.01); *C07D 233/36* (2013.01); *C07D 237/30* (2013.01); *C07D 239/34* (2013.01); *C07D 239/42* (2013.01); *C07D 249/14* (2013.01); *C07D 261/14* (2013.01); *C07D 271/12* (2013.01); *C07D 277/18* (2013.01); *C07D 277/66* (2013.01); *C07D 285/14* (2013.01); *C07D 295/088* (2013.01); *C07D 295/135* (2013.01); *C07D 295/192* (2013.01); *C07D 307/88* (2013.01); *C07D 317/66* (2013.01); *C07D 319/08* (2013.01); *C07D 333/20* (2013.01); *C07D 333/38* (2013.01); *C07D 405/12* (2013.01); *C07D 409/04* (2013.01); *C07C 2601/02* (2017.05); *C07C 2602/08* (2017.05)

(58) Field of Classification Search
CPC ... C07C 275/30; C07C 275/34; C07C 275/38; C07C 275/40; C07C 2601/02; C07C 2602/08; C07C 2601/102; A61K 31/5377; C07D 213/75; C07D 213/81; C07D 215/06; C07D 231/56; C07D 233/36; C07D 237/30; C07D 239/34; C07D 239/42; C07D 249/14; C07D 261/14; C07D 271/12; C07D 277/18; C07D 277/66; C07D 285/14; C07D 295/088; C07D 295/135; C07D 295/192; C07D 307/88; C07D 317/66; C07D 319/08; C07D 333/20; C07D 333/38; C07D 405/12; C07D 409/04
See application file for complete search history.

(56) References Cited

U.S. PATENT DOCUMENTS 6,525,091 B2 * 2/2003 Robinson ............. C07C 275/30
514/517
6,984,647 B2 1/2006 Dax et al.
(Continued)

FOREIGN PATENT DOCUMENTS

| WO | WO 9900357 A1 * | 1/1999 | ........... C07C 275/28 |
|---|---|---|---|
| WO | 2006049941 A2 | 5/2006 | |
| WO | 2006125540 A1 | 11/2006 | |

OTHER PUBLICATIONS

RN685123-54-0, available May 24, 2004.*
(Continued)

Primary Examiner — Kortney L Klinkel
Assistant Examiner — Ibrahim D Bori
(74) Attorney, Agent, or Firm — Banner & Witcoff, Ltd.

(57) ABSTRACT

Compositions and methods for inhibiting translation initiation are provided. Compositions, methods and kits for treating (1) cellular proliferative disorders, (2) non-proliferative, degenerative disorders, (3) viral infections, and/or (4) disorders associated with viral infections, using N,N'-diarylureas and/or N,N'-diarylthiourea compounds are described.

1 Claim, 21 Drawing Sheets

(51) Int. Cl.
  C07D 295/088   (2006.01)
  C07D 295/135   (2006.01)
  C07D 295/192   (2006.01)
  C07D 307/88    (2006.01)
  C07D 317/66    (2006.01)
  C07D 319/08    (2006.01)
  C07D 333/20    (2006.01)
  C07D 333/38    (2006.01)
  C07D 405/12    (2006.01)
  C07D 409/04    (2006.01)

(56) References Cited

U.S. PATENT DOCUMENTS

2005/0038031 A1   2/2005   Dumas et al.
2007/0099976 A1   5/2007   Halperin et al.
2008/0045589 A1   2/2008   Kelley

OTHER PUBLICATIONS

RN685123-54-0 (available May 24, 2004).*
International Search Report and Written Opinion relating to PCT/US2010/036584.
Aktas, et al., "Depletion of Intracellular Ca2+ Stores, Phosphorylation of eIF2., and Sustained Inhibition of Translation Initiation Mediate the Anticancer Effects of Clotrimazole,".
Berns, Anton, "A tRNA with Oncogenic Capacity," Cell, 133, Apr. 4, 2008.
Kozak, Marilyn, "An Analysis of Vertebrate mRNA Sequences: Intimations of Translational Control," The Journal of Cell Biology, vol. 115, No. 4, Nov. 1991, 887-903.
Kozak, M., "Determinants of Translational Fidelity and Efficiency in Vertebrate mRNAs," Biochimie, (1994) 76, 815-821.
Kozak, Marilyn, "Initiation of Translation in Prokaryotes and Eukaryotes," Gene, 234 (1999) 187-208.
Marshall, et al., "Elevated tRNAiMET Synthesis Can Drive Cell Proliferation and Oncogenic Transformation," Cell, 133, 78-89, Apr. 4, 2008.
Palakurthi, et al., "Inhibition of Translation Initiation Mediates the Anticancer Effect of the n-3 Polyunsaturated Fatty Acid Eicosapentaenoic Acid," Cancer Research, 60, 2919-2925, Jun. 1, 2000.
Palakurthi, et al., "Anticancer Effects of Thiazolidinediones are Independent of Peroxisome Proliferator-activated Receptor . and Mediated by Inhibition of Translation Initiation," Cancer Research, 61, 6213-6218, Aug. 15, 2001.

* cited by examiner

A
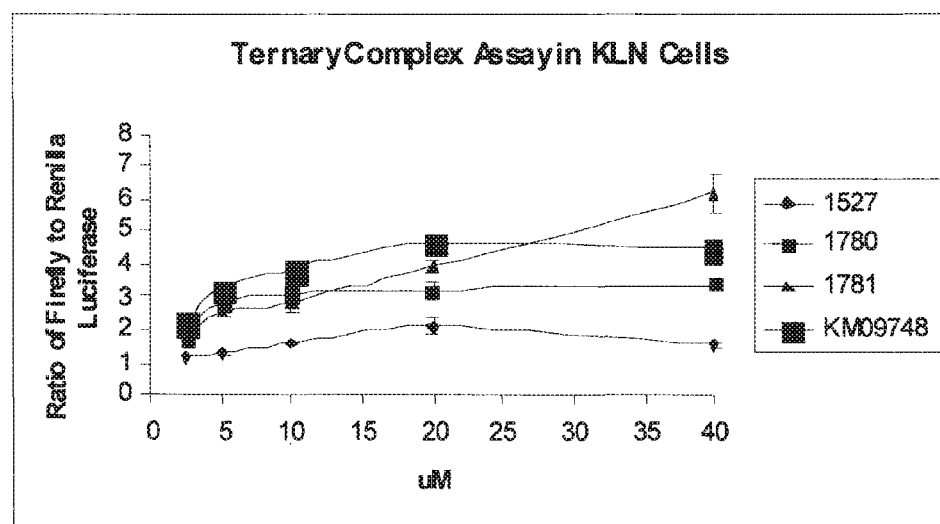
B
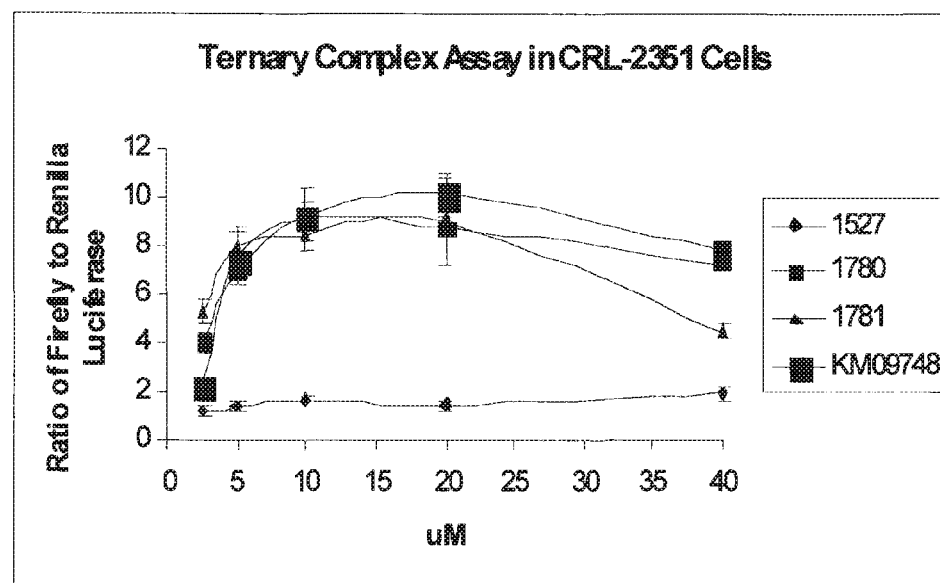
Figure 1

C
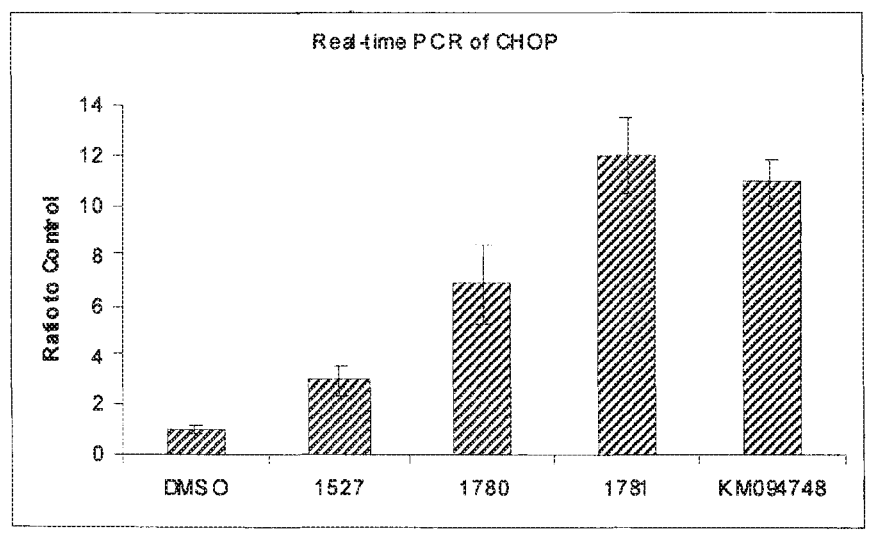
D
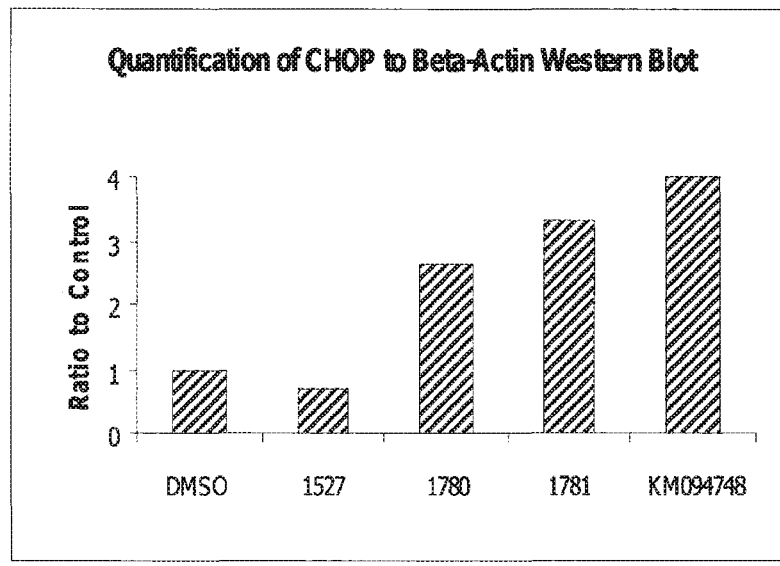
Figure 1 (Cont.)

A
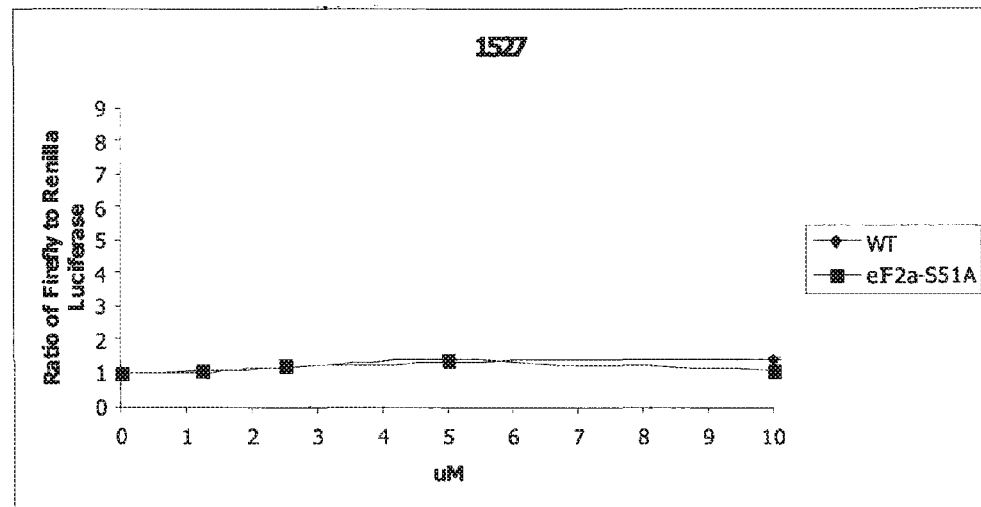
B
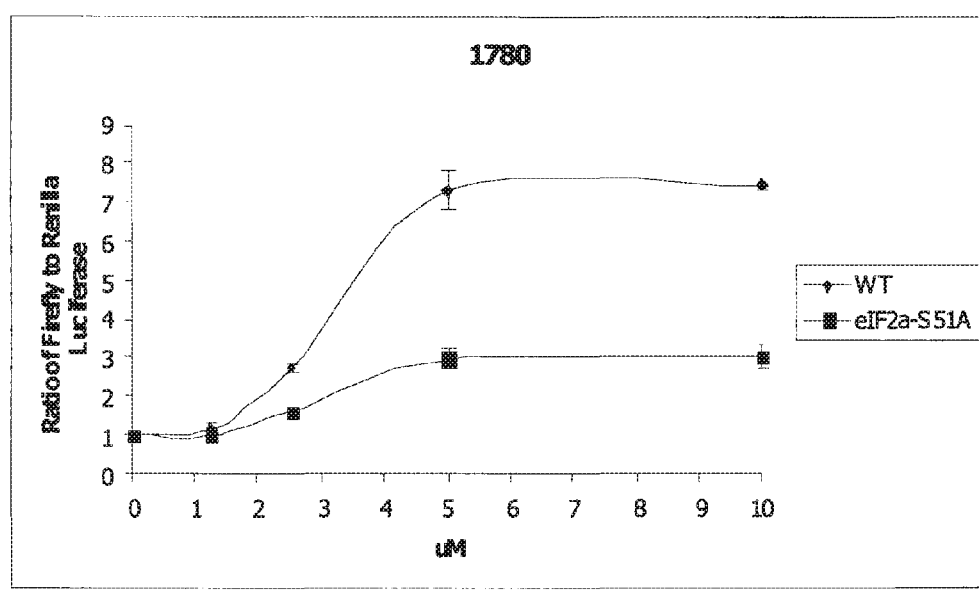
Figure 3

C
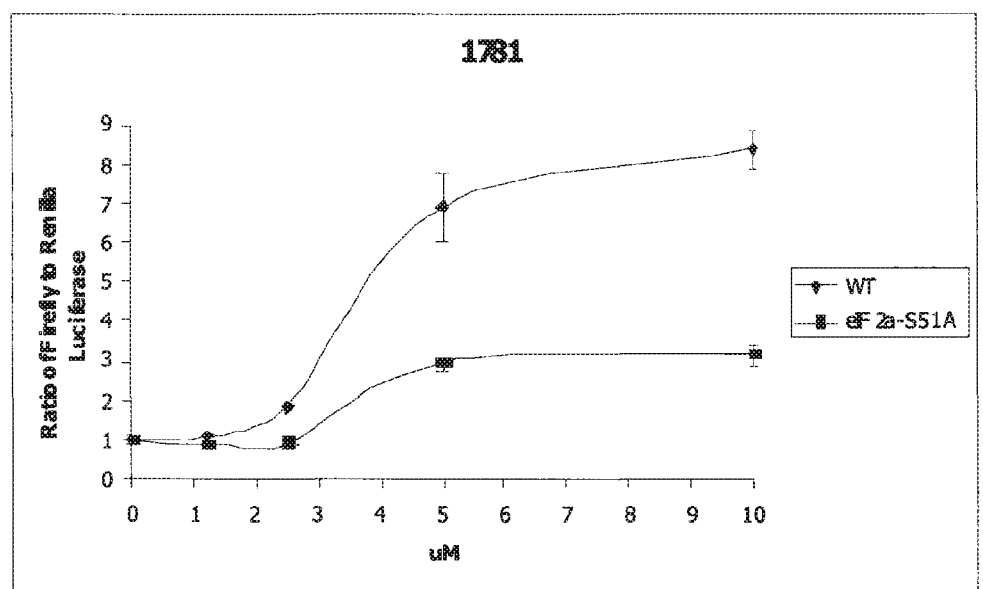
D
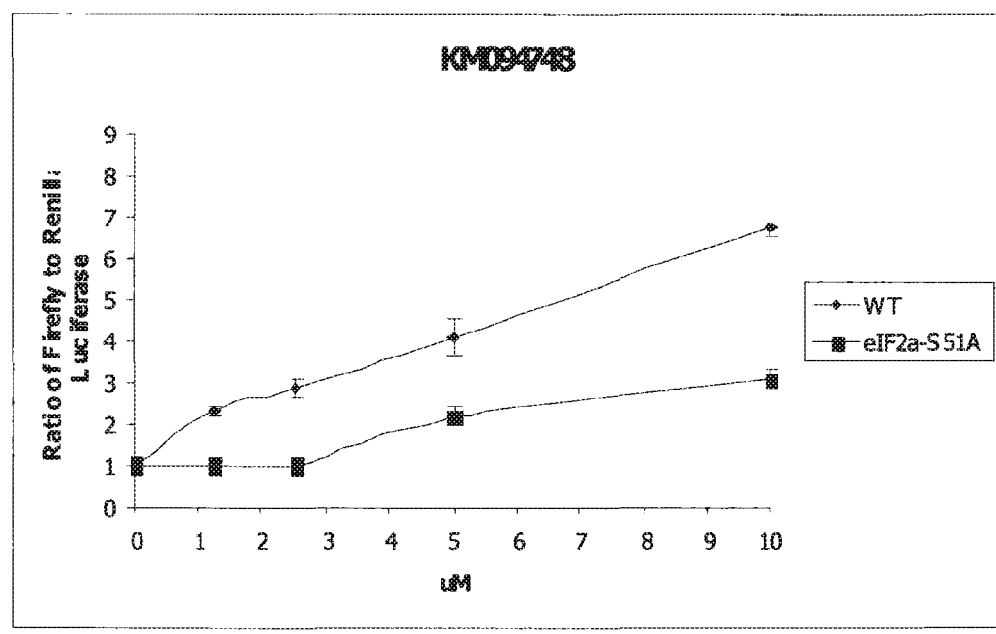
Figure 3 (Cont.)

A
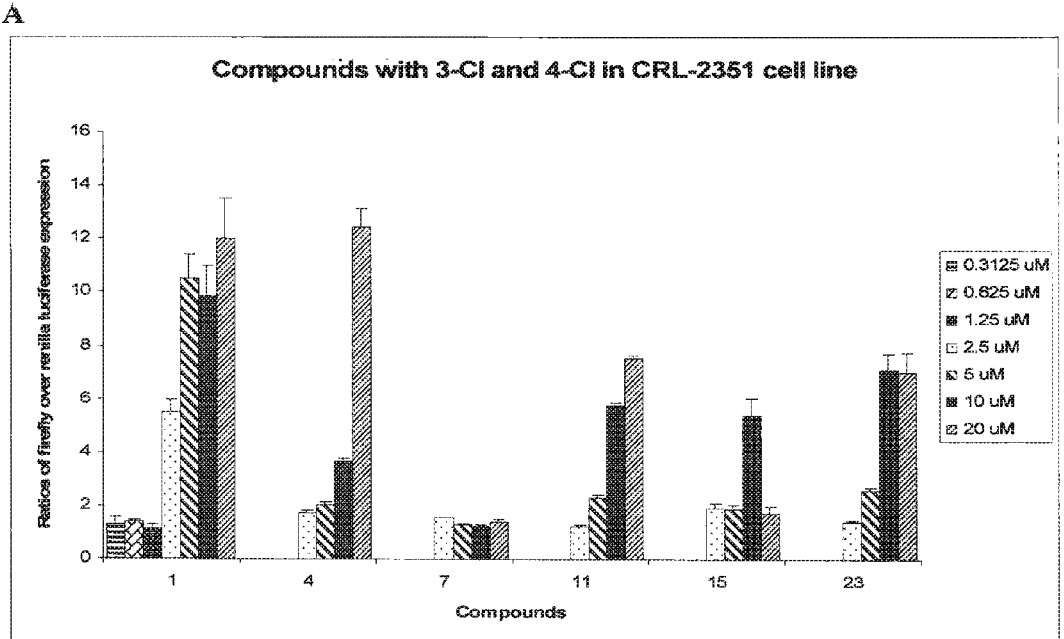
B
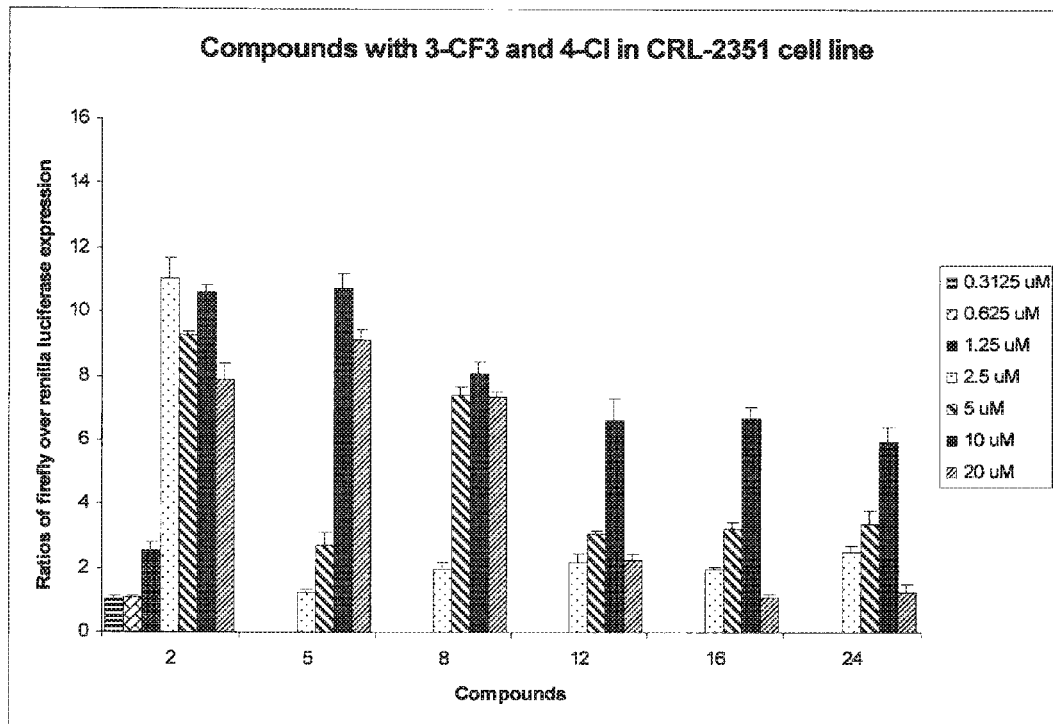
Figure 4

C
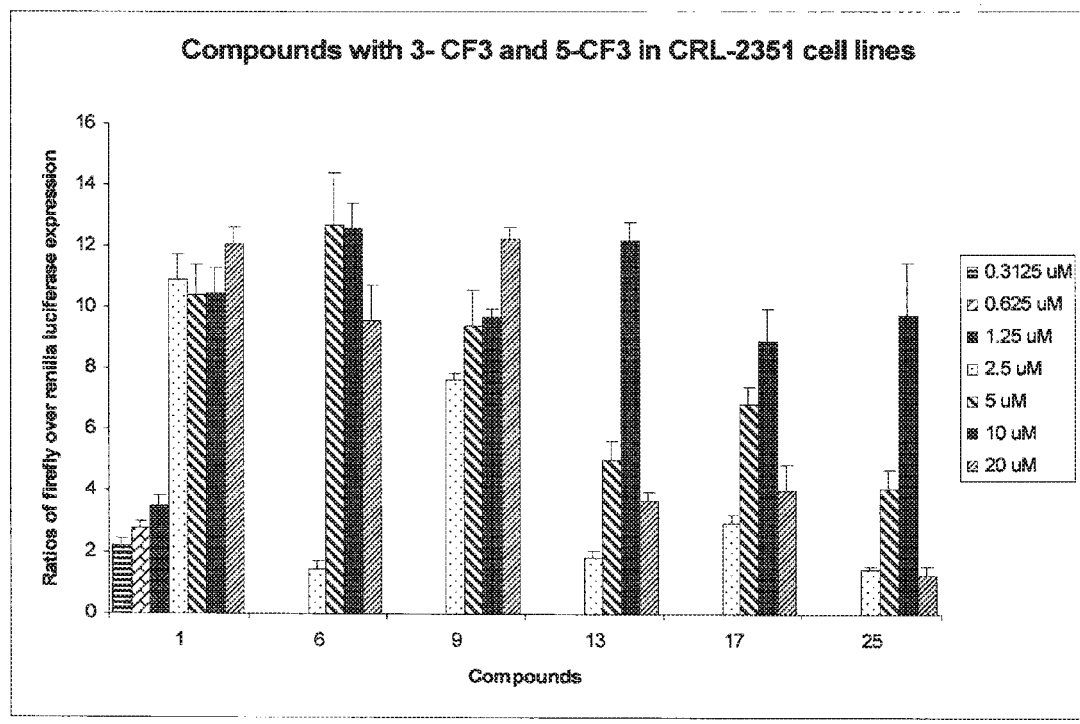
D
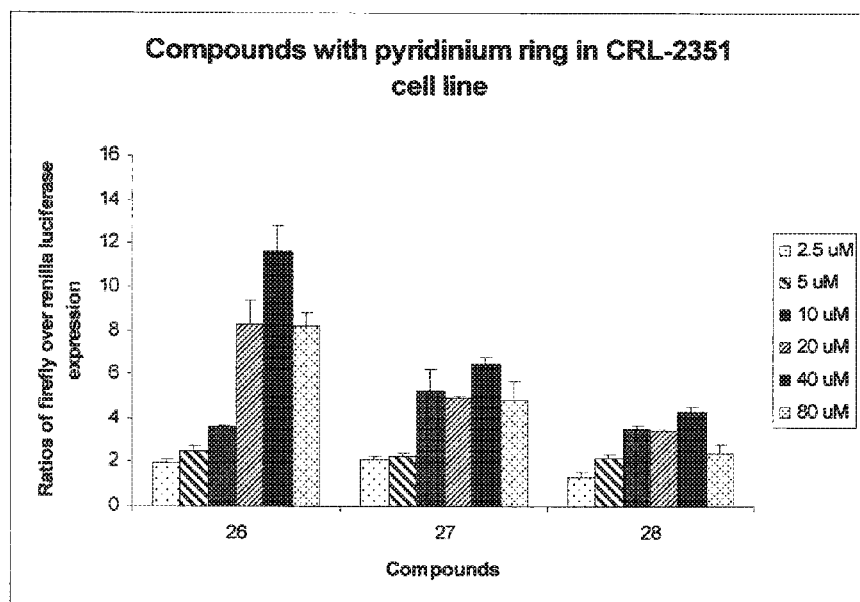
Figure 4 (Cont.)

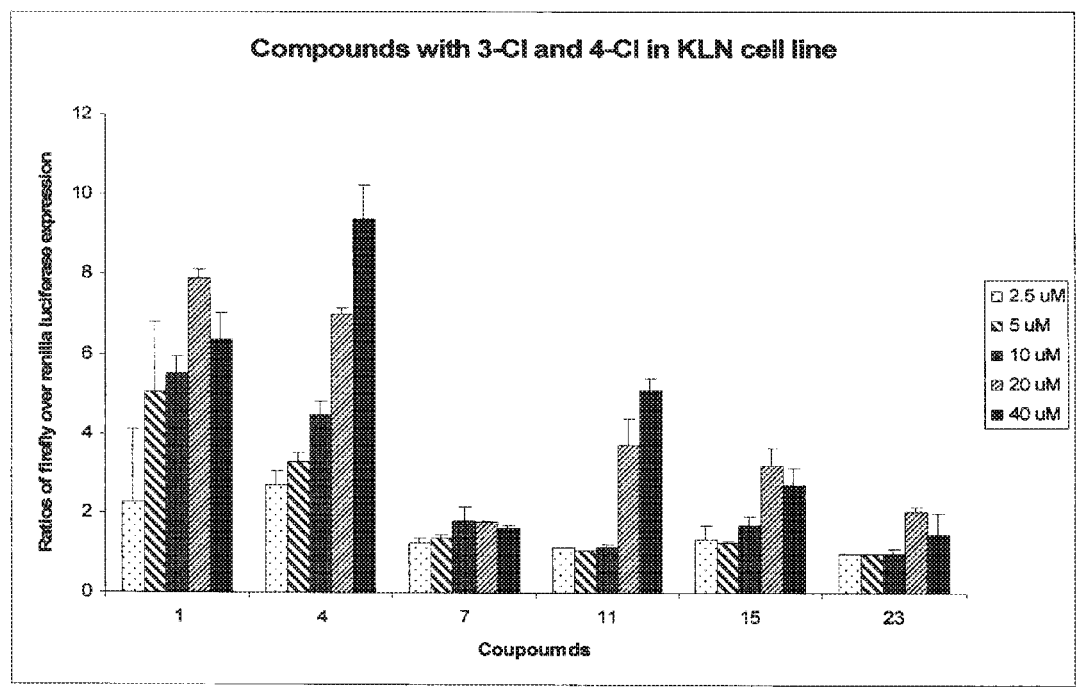
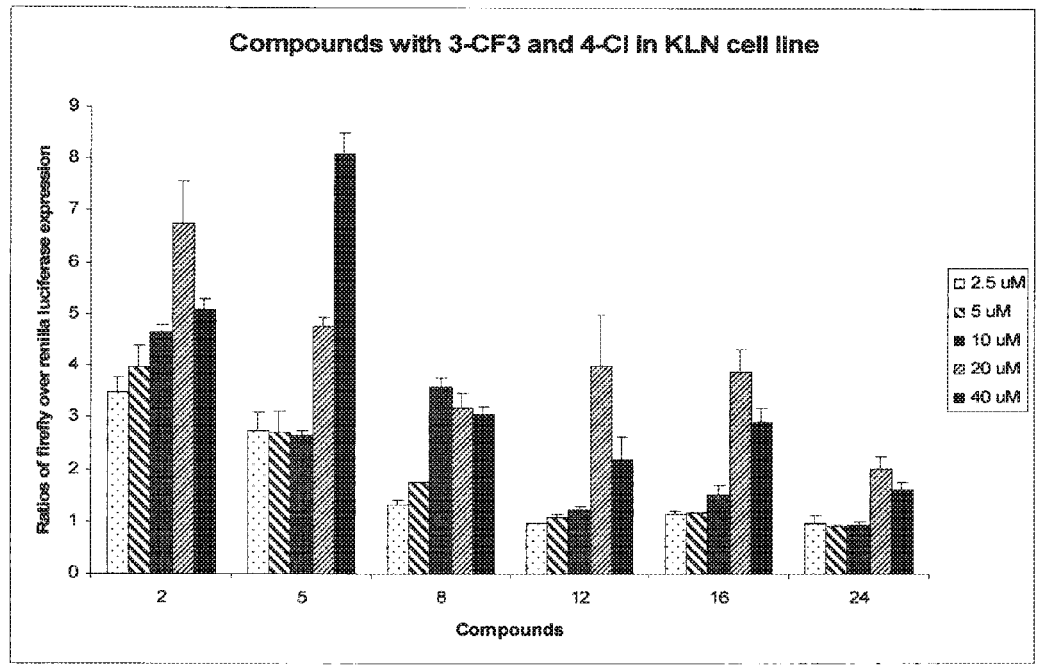
Figure 5

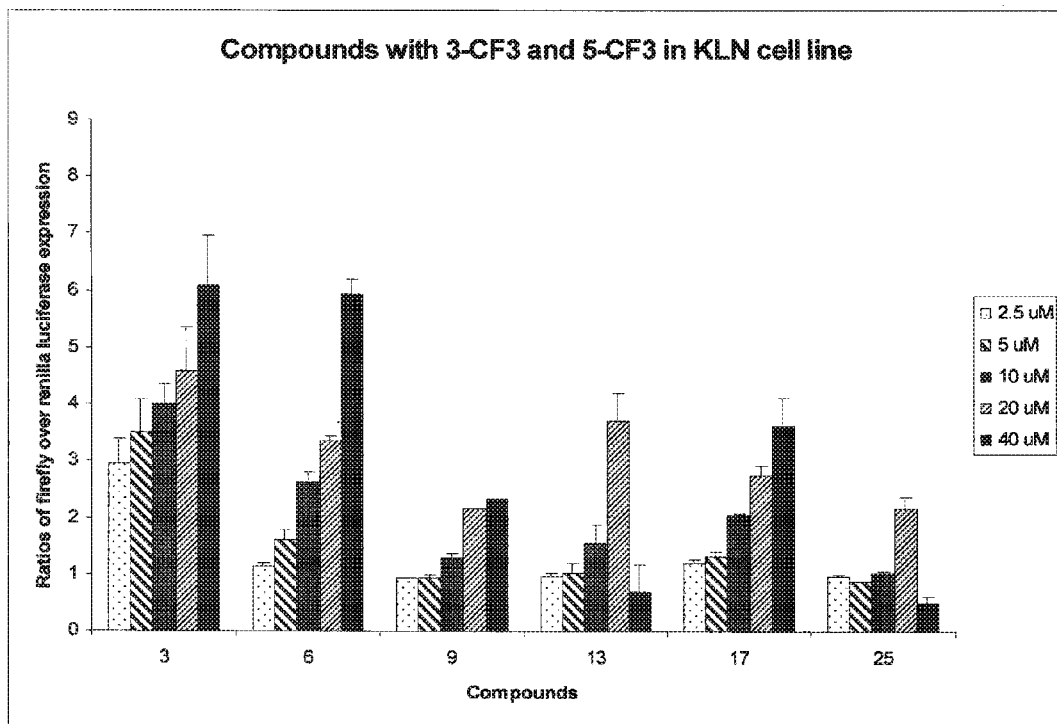
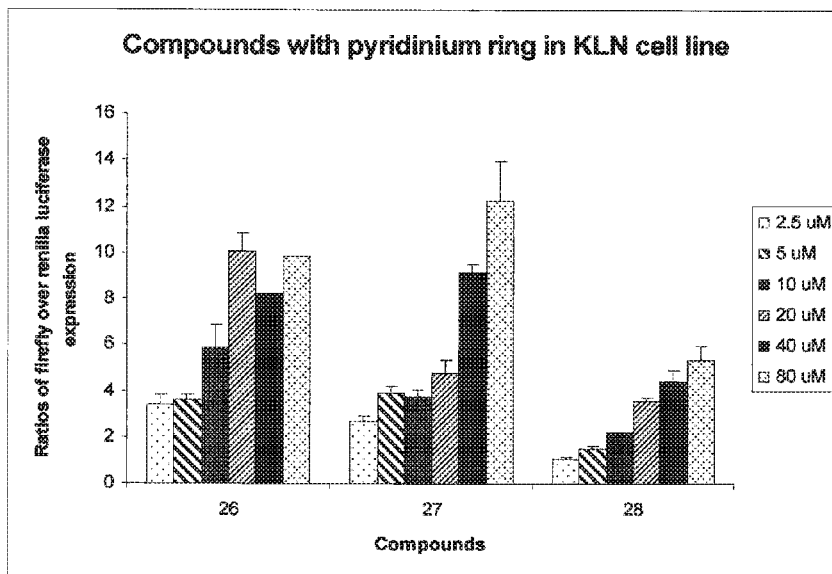
Figure 5 (Cont.)

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: PCR Primer

<400> SEQUENCE: 1
agaaccagga aacggaaaca ga                                            22

<210> SEQ ID NO 2
<211> LENGTH: 20
<212> TYPE: DNA
<213> ORGANISM: Artificial Sequence
<220> FEATURE:
<223> OTHER INFORMATION: PCR Primer

<400> SEQUENCE: 2
tctccttcat gcgctgcttt                                               20

<210> SEQ ID NO 3
<211> LENGTH: 22
<212> TYPE: DNA
<213> ORGANISM: Artificial Sequence
<220> FEATURE:
<223> OTHER INFORMATION: PCR Primer

<400> SEQUENCE: 3
catacaccac cacacctgaa ag                                            22

<210> SEQ ID NO 4
<211> LENGTH: 22
<212> TYPE: DNA
<213> ORGANISM: Artificial Sequence
<220> FEATURE:
<223> OTHER INFORMATION: PCR Primer

<400> SEQUENCE: 4
ccgtttccta gttcttcctt gc                                            22

```
<210> SEQ ID NO 5
<211> LENGTH: 18
<212> TYPE: DNA
<213> ORGANISM: Artificial Sequence
<220> FEATURE:
<223> OTHER INFORMATION: PCR Primer

<400> SEQUENCE: 5
cggaggagaa caaacaga                                                 18

<210> SEQ ID NO 6
<211> LENGTH: 18
<212> TYPE: DNA
<213> ORGANISM: Artificial Sequence
<220> FEATURE:
<223> OTHER INFORMATION: PCR Primer

<400> SEQUENCE: 6
tgaggcggta gtaggaca                                                 18

<210> SEQ ID NO 7
<211> LENGTH: 21
<212> TYPE: DNA
<213> ORGANISM: Artificial Sequence
<220> FEATURE:
<223> OTHER INFORMATION: PCR Primer

<400> SEQUENCE: 7
taccgcacaa cgcactttct t                                             21

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
cgcaggcttg actccagaag                                               20

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
cggcgacgac ccattcgaac                                               20

<210> SEQ ID NO 10
<211> LENGTH: 23
<212> TYPE: DNA
<213> ORGANISM: Artificial Sequence
<220> FEATURE:
<223> OTHER INFORMATION: PCR Primer

<400> SEQUENCE: 10
gaatcgaacc ctgattcccc gtc                                           23
```

N,N'-DIARYLUREA COMPOUNDS AND N,N'-DIARYLTHIOUREA COMPOUNDS AS INHIBITORS OF TRANSLATION INITIATION

RELATED APPLICATION DATA

This application is a continuation application which claims priority to U.S. patent application Ser. No. 13/322,607, filed on Jan. 24, 2012, which is a National Stage Application under 35 U.S.C. 371 of co-pending PCT application PCT/US2010/036584 designating the United States and filed May 28, 2010; which claims the benefit of U.S. provisional application Ser. No. 61/181,920 filed May 28, 2009, each of which are hereby incorporated by reference in their entireties.

STATEMENT OF GOVERNMENT INTERESTS

This invention was made with government support under 5 U19 CA87427 awarded by the National Institutes of Health. The government has certain rights in the invention.

FIELD

The present invention relates to novel compounds which inhibit translation initiation, pharmaceutical compositions of the novel compounds, and methods of treating medical disorders.

BACKGROUND

Translation, the mRNA-directed synthesis of proteins, occurs in three distinct steps: initiation, elongation and termination. Translation initiation is a complex process in which the two ribosomal subunits and methionyl tRNA (Met-tRNA$_i$) assemble on a properly aligned mRNA to commence chain elongation at the AUG initiation codon. The established scanning mechanism for initiation involves the formation of a ternary complex among eukaryotic initiation factor 2 (eIF2), GTP and Met-tRNA$_i$. The ternary complex recruits the 40S ribosomal subunit to form the 43S pre-initiation complex. This complex recruits mRNA in cooperation with other initiation factors such as eukaryotic initiation factor 4E (eIF4E), which recognizes the 7-methyl-guanidine cap (m-$^7$GTP cap) in an mRNA molecule and forms the 48S pre-initiation complex. Cap recognition facilitates the 43S complex entry at the 5' end of a capped mRNA. Subsequently, this complex migrates linearly until it reaches the first AUG codon, where a 60S ribosomal subunit joins the complex, and the first peptide bond is formed (Pain (1996) *Eur. J. Biochem.*, 236:747-771). After each initiation, the GTP in the ternary complex is converted to GDP. The eIF2 GDP binary complex must be converted to eIF2 GTP by the guanidine exchange factor, eIF2B for a new round of translation initiation to occur. Inhibition of this exchange reaction by phosphorylation of eIF2α reduces the abundance of the ternary complex and inhibits translation initiation. Forced expression of non-phosphorylatable eIF2α or Met-tRNA$_i$ causes transformation of normal cells (Marshall (2008) *Cell* 133:78; Berns (2008) *Cell* 133:29). In contrast, pharmacologic agents that restrict the amount of eIF2-GTP-Met-tRNA$_i$ ternary complex inhibit proliferation of cancer cells in vitro and tumors in vivo (Aktas (1998) *Proc. Natl. Acad. Sci. U.S.A.* 95:8280), Palakurthi (2000) *Cancer Res.* 60:2919, Palakurthi (2001) *Cancer Res.* 61: 6213). These findings indicate that more potent and specific agents that reduce amount of ternary complex are potent anti-cancer agents.

Several features of the mRNA structure influence the efficiency of its translation. These include the m-$^7$GTP cap, the primary sequence surrounding the AUG codon and the length and secondary structure of the 5' untranslated region (5' UTR). Indeed, a moderately long, unstructured 5' UTR with a low G and C base content seems to be optimal to ensure high translational efficiency. Surprisingly, sequence analysis of a large number of vertebrate cDNAs has shown that although most transcripts have features that ensure translational fidelity, many do not appear to be designed for efficient translation (Kozak (1991) *J. Cell. Biol.*, 115:887-903). Many vertebrate mRNAs contain 5' UTRs that are hundreds of nucleotides long with a remarkably high GC content, indicating that they are highly structured because G and C bases tend to form highly stable bonds. Because highly structured and stable 5' UTRs are the major barrier to translation, mRNAs with stable secondary structure in their 5' UTR are translated inefficiently and their translation is highly dependent on the activity of translation initiation factors. mRNAs with complex, highly structured 5' UTRs include a disproportionately high number of proto-oncogenes such as the G1 cyclins, transcription and growth factors, cytokines and other critical regulatory proteins. In contrast, mRNAs that encode globins, albumins, histones and other housekeeping proteins rarely have highly structured, GC-rich 5' UTRs (Kozak (1994) *Biochimie*, 76; 815-21; Kozak (1999) *Gene*, 234:187-208). The fact that genes encoding for regulatory but not for housekeeping proteins frequently produce transcripts with highly structured 5' UTRs indicates that extensive control of the expression of regulatory genes occurs at the level of translation. In other words, low efficiency of translation is a control mechanism which modulates the yield of proteins such as cyclins, mos, c-myc, VEGF, TNF, among others, that could be harmful if overproduced.

Translation initiation is a critical step in the regulation of cell growth because the expression of most oncogenes and cell growth regulatory proteins is translationally regulated. One approach to inhibiting translation initiation has recently been identified using small molecule known as translation initiation inhibitors. Translation initiation inhibitors such as clotrimazole (CLT) inhibit translation initiation by sustained depletion of intracellular $Ca^{2+}$ stores. Depletion of intracellular $Ca^{2+}$ stores activates "interferon-inducible" "double-stranded RNA activated" protein kinase (PKR) which phosphorylates and thereby inhibits the a subunit of eIF2. Since the activity of eIF2 is required for translation initiation, its inhibition by compounds such as CLT reduces the overall rate of protein synthesis. Because most cell regulatory proteins are encoded for by mRNAs containing highly structured 5' UTRs, they are poorly translated and their translation depends heavily on translation initiation factors such as eIF2 and eIF4. Therefore, inhibition of translation initiation preferentially affects the synthesis and expression of growth regulatory proteins such as G1 cyclins. Sequential synthesis and expression of G1 cyclins (D1, E and A) is necessary to drive the cell cycle beyond the restriction point in late G1. Thus, the decreased synthesis and expression of G1 cyclins resulting from CLT-induced inhibition of translation initiation causes cell cycle arrest in G1 and inhibits cancer cell and tumor growth (Aktas et al. (1998) *Proc. Natl. Acad. Sci. USA*, 95:8280-8285, incorporated herein by reference in its entirety for all purposes).

Like CLT, the n-3 polyunsaturated fatty acid eicosapentaenoic acid (EPA) depletes internal calcium stores, and exhibits anti-carcinogenic activity. Unlike CLT, however, EPA is a ligand of peroxisome proliferator-activated receptor gamma (PPARγ), a fatty acid-activated transcription factor. Although EPA and other ligands of PPARγ, such as troglitazone and ciglitazone, inhibit cell proliferation, they do so in a PPARγ-independent manner (Palakurthi et al. (2000) Cancer Research, 60:2919; and Palakurthi et al. (2001) Cancer Research, 61:6213, incorporated herein by reference in their entirety for all purposes).

SUMMARY

Embodiments of the present invention are directed to compounds that inhibit translation initiation, and the use of such compounds or combination of compounds for treating (1) proliferative disorders, (2) non-proliferative, degenerative disorders, (3) viral infections, (4) disorders associated with viral infections, and/or (5) disorders characterized by unwanted protein synthesis or diseases for which reducing protein synthesis is advantageous.

In at least certain examples, the compounds are of substituted diarylureas, more particularly, substituted N,N'-diarylurea compounds. In other examples, the compounds are substituted thioureas, more particularly, substituted N,N'-diarylthiourea compounds. In certain exemplary embodiments, substituted N,N'-diarylurea and/or substituted N,N'-diarylthiourea compounds include compounds comprising Formula I, Formula II, Formula III, Formula IV and/or compounds set forth in Tables 1-6, FIGS. 1-12 and the Appendix.

In certain examples, the substituted N,N'-diarylurea and/or substituted N,N'-diarylthiourea compounds described herein cause phosphorylation of eIF2α. In other examples, substituted N,N'-diarylurea and/or substituted N,N'-diarylthiourea compounds are effective to inhibit translation initiation.

In accordance with a method aspect, a method of treating a proliferative disorder by providing and/or administering a compound of Formula I and/or Formula II and/or Formula III and/or Formula IV to a mammal, e.g., a human or a non-human (e.g., a non-human primate), is provided. In one example, the proliferative disorder is cancer. In accordance with other examples, a method of treating a viral infection by providing and/or administering a compound of Formula I and/or Formula II and/or Formula III and/or Formula IV to a mammal, e.g. a human or a non-human mammal, is provided.

In accordance with an additional aspect, kits are provided for the treatment of (1) proliferative disorders, (2) non-proliferative, degenerative disorders, (3) viral infections, (4) disorders associated with viral infections, and/or (5) disorders characterized by unwanted protein synthesis or diseases for which reducing protein synthesis is advantageous In one aspect, the kits comprise a compound of Formula I and/or Formula II and/or Formula III and/or Formula IV, a pharmaceutically acceptable carrier, and optionally, instructions for use. The pharmaceutical composition can be administered to a human subject or a non-human subject depending on the disorder to be treated.

It will be recognized by the person of ordinary skill in the art that the compounds, compositions, methods and kits disclosed herein provide significant advantages over prior technology. Compounds, compositions, methods and kits can be designed or selected to relieve and/or alleviate symptoms in a patient suffering from one or more disorders. These and other aspects and examples are described below.

BRIEF DESCRIPTION OF THE DRAWINGS

The foregoing and other features and advantages of the present invention will be more fully understood from the following detailed description of illustrative embodiments taken in conjunction with the accompanying drawings.

FIGS. 1A-1D graphically depict ternary complex assays. (A) KLN cells. (B) CRL-2351 cells. (C) Real-time PCR of CHOP. (D) Quantification of CHOP to beta-actin Western blot.

FIGS. 3A-3D graphically depict the ratios of firefly luciferase (F-luc): *renilla* luciferase (R-luc) for compounds 1527 (A), 1780 (B), 1781 (C) and KM94748 (D) in PC-3 cells transfected with ether wild-type (WT) eIF2α or non-phosphorylatable eIF2α-S51A mutant.

FIGS. 4A-4D graphically depict ATF-4 assays using substituted N,N'-diarylureas (numbers of compounds correspond to structures in Table 1) in CRL-2351 cells.

FIGS. 5A-5D graphically depict ATF-4 assays using substituted N,N'-diarylureas (numbers of compounds correspond to structures in Table 1) in KLN cells.

Figure 9:
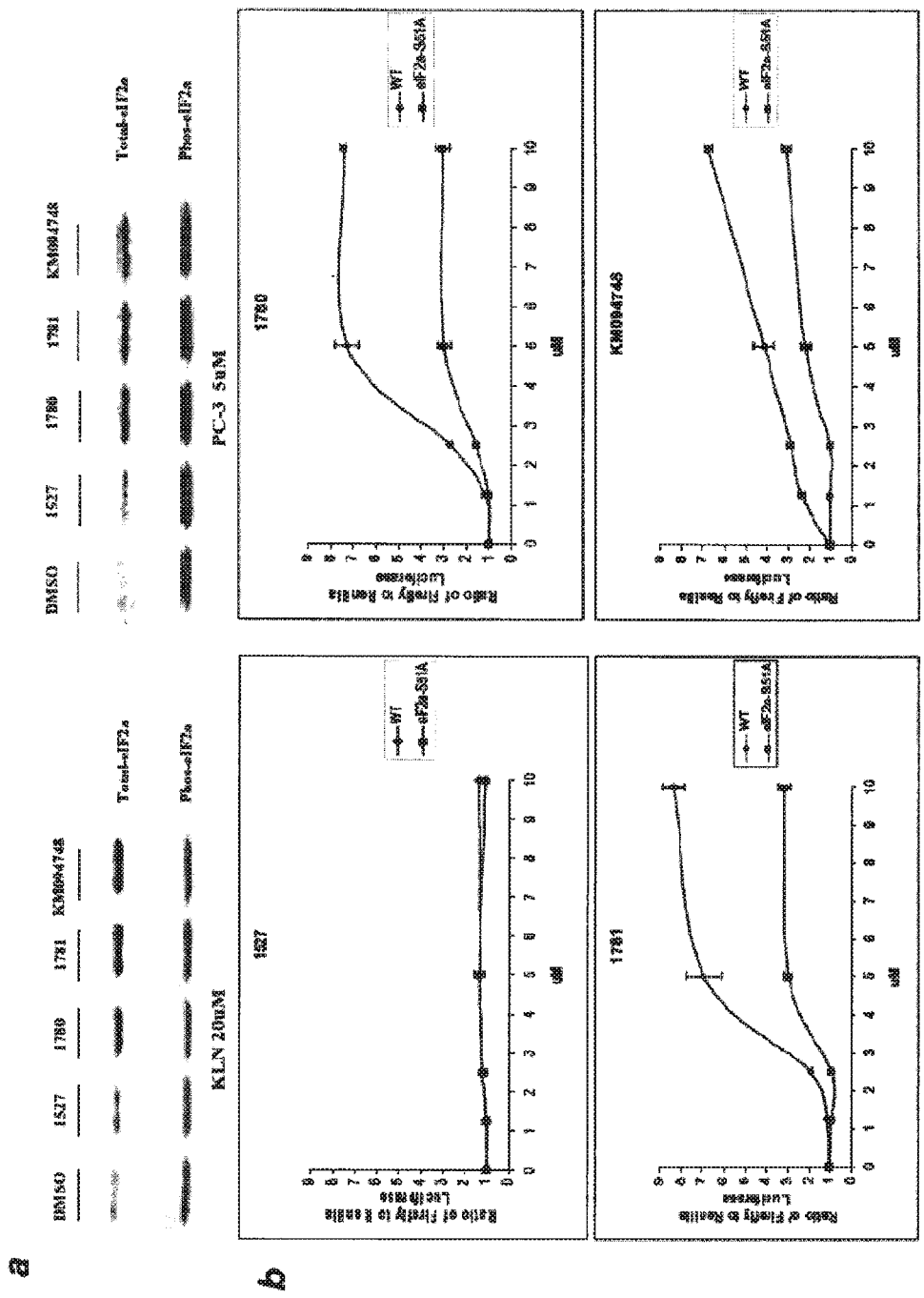

FIGS. 9A-9B depict that N,N'-diarylureas modify the eIF2-GTP-Met-tRNA$_i$ ternary complex by causing the phosphorylation of eIF2α. A) KLN-tTA/pBISA-DL$^{(ATF-4)}$ or PC-3 cell lines were incubated with N,N'-diarylureas, levels of total eIF2α was determined by Western blot analysis with mouse monoclonal antibodies (Biosource International, MA) and the level of phosphorylated eIF2α was determined by Western blot analysis with phosphor-serine 51 (Phos-eIF2α) specific recombinant rabbit monoclonal antibodies (Epitomics Inc, CA). B) The PC-3 cells in which endogenous eIF2α was replaced with recombinant WT or non-phosphorylatable eIF2α-S51A mutant were co-transfected with tTA and pBISA-DL$^{(ATF-4)}$ dual luciferase expression vector and treated with indicated concentrations of N,N'-diarylurea compounds. Firefly/renilla ratio was determined by DLR assay.

Figure 10:
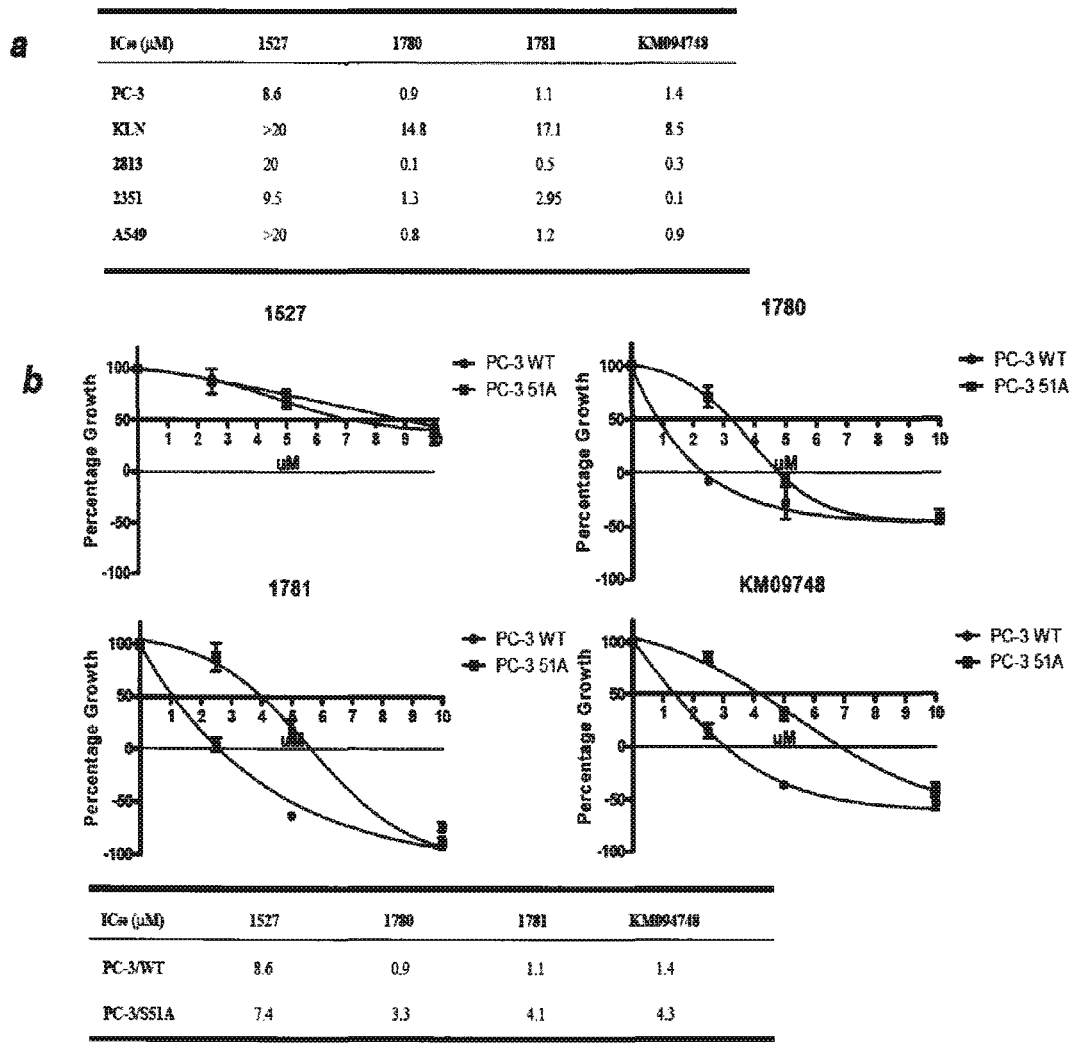

FIGS. 10A-10B depict that reducing availability of the eIF2-GTP-Met-tRNA$_i$ ternary complex inhibits cancer cell proliferation. A) Various human and mouse cancer cell lines were incubated with the indicated concentrations of N,N'-diarylurea compounds, net cell proliferation was determined by SRB assay. B) The PC-3 human prostate cancer cells in which endogenous eIF2α was replaced with recombinant WT eIF2α or non-phosphorylatable eIF2α-S51A mutant were treated with the indicated concentrations of N,N'-diarylurea compounds and cell proliferation was measured by Sulforhodamine B (SRB) assay.

FIGS. 11A-11B depict that reducing availability of the eIF2-GTP-Met-tRNA$_i$ ternary complex modified expression of cell cycle regulatory proteins. A) Mouse KLN cells were incubated with 20 μM and human PC3 cancer cell lines were incubated with 5 μM N,N'-diarylurea compounds and expression of cyclin D1 or β-actin was determined by Western blot analysis. B) KLN and PC-3 cells were treated as in A and expression of cyclin D1 mRNA was determined with real time PCR.

FIGS. 12A-12D depict that the N,N'-Diarylurea compounds specifically activate HRI kinase. A) KLN-tTA/pBISA-DL$^{(ATF-4)}$ cells were transfected with mock siRNA or siRNA targeting PKR, PERK, GCN2, HRI or PKR, PERK, GCN2 simultaneously. Cells were treated with compound #1781 or DMSO and F-luc/R-luc ratio was determined by DLR. B) KLN-tTA/pBISA-DL$^{(ATF-4)}$ cells treated as in A, the expression of CHOP mRNA was determined by real-time PCR. C). KLN-tTA/pBISA-DL$^{(ATF-4)}$ cells were transfected with mock siRNA or siRNA targeting HRI, the cells were treated with N,N'-diarylurea compounds or vehicle and the F-luc/R-luc ratio was determined by DLR. D) Cells were transfected with mock siRNA or siRNA targeting PKR. PERK, GCN2, or HRI and knockdown efficiency for each gene was determined by real-time PCR.

FIGS. 13A-13E depict that the N,N'-diarlyurea compounds specifically activate HRI kinase. A) KLN-tTA/pBISA-DL$^{(ATF-4)}$ cells were transfected with mock siRNA or siRNA targeting PKR, PERK, GCN2, or HRI individually or simultaneously in all combinations (only PKR, PERK, and GCN2 combination is shown). CRL-2813 cells were transfected, in the same manner except that the transfection mixture also contained the tTA plasmid. Cells were treated with compound #1781 or DMSO and the normalized F/R ratio was determined by DLR. B) KLN-tTA/pBISA-DL$^{(ATF-4)}$ or CRL-2813 cells were transfected with siRNAs targeting each eIF2α kinases and treated with compound #1781 or DMSO, expression of CHOP mRNA was determined by real-time PCR. C) CRL-2813 cells were transfected with mock or HRI siRNA, treated with compound #1781 or vehicle, levels of phosphorylated (p-eIF2α) and total eIF2α (eIF2α) were determined by Western blot. Right panel show the quantification of the western blot. D) KLN-tTA/pBISA-DL$^{(ATF-4)}$ cells were transfected with mock or HRI targeting siRNA, treated with four N,N'-diarylurea compounds or vehicle and the normalized F/R ratio was determined by DLR. E) CRL-2813 cells were transfected with mock siRNA or HRI siRNA, treated with compound #1781 or vehicle and phosphorylation of eIF2α was determined by Western blot analysis.

FIGS. 14A and 14B depict that N,N'-diarylurea compounds activate HRI in cell free lysates. A and B) Heme supplemented rabbit reticulocyte (a) or in-house prepared human melanoma cancer cell lysates (b) were incubated with the indicated concentration of compound 1781 for 30 minutes at 37° C. and phosphorylation of eIF2α was determined by Western blot analysis. Left panels shows quantification of data from three different gels.

FIGS. 15A-15D depict that phosphorylation of eIF2α by HRI mediates inhibition of cancer cell proliferation by N,N'-diarylureas. A and B) The PC-3 human prostate cancer cells in which endogenous eIF2α is replaced by recombinant WT or non-phosphorylatable eIF2α-S51A mutant were treated with the indicated concentrations of N,N'-diarylureas and cell proliferation was measured by SRB assay. Panel a shows the growth inhibition curve for one active (compound #1780) and one inactive (compound #1527) N,N'-diarylurea, panel B shows the calculated IC$_{50}$ for all four compounds in these genetically engineered cell lines. C) CRL-2813 human melanoma cancer cells were transfected with HRI or mock siRNA, treated with the indicated concentrations of N,N'-diarylureas and cell proliferation was measured by SRB assay. Panel c shows the growth inhibition curve for one active (compound #1780) and one inactive (compound #1527) N,N'-diarylurea, panel D) shows the calculated IC$_{50}$ for all four compounds in cells transfected with HRI or mock siRNA.

Figure 16:
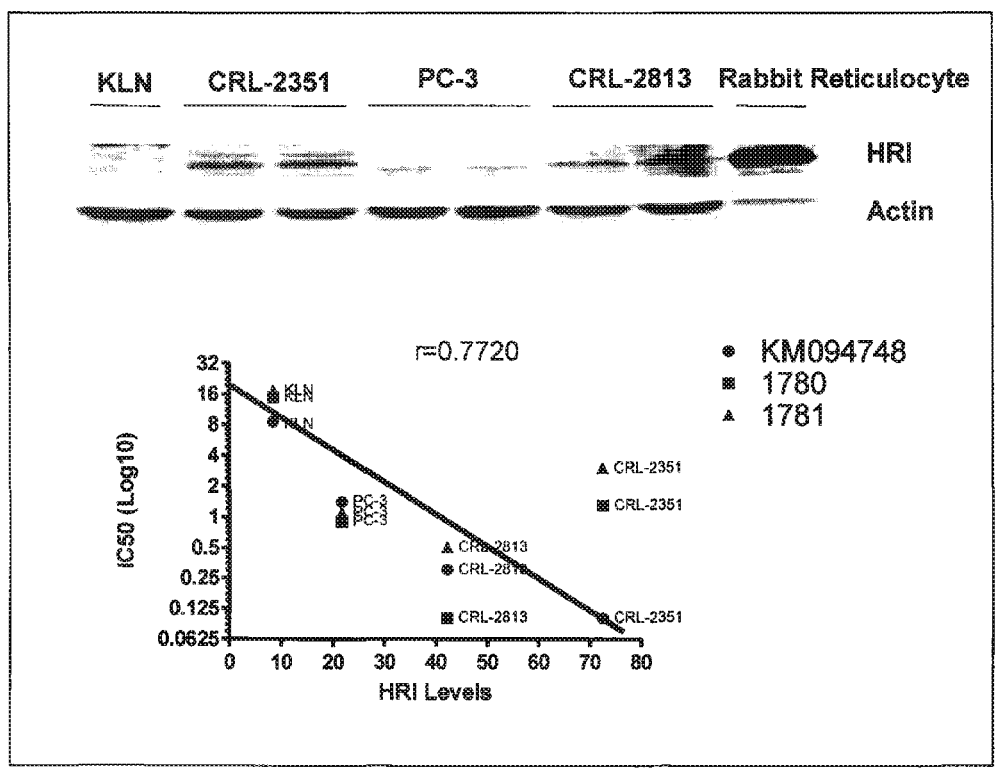

FIG. 16 depicts that expression of HRI in cancer cell lines correlates with anti-proliferative activity of N,N'-diarylureas. Lysates were prepared from mouse KLN squamos cell carcinoma, human CRL-2351 breast, PC-3 prostate, and CRL-2813 melanoma cancer cells, separated by SDS-PAGE and probed with antibodies specific to HRI or β-actin (top panel). The IC$_{50}$ of three active N,N'-diarylureas were plotted against the levels of HRI (corrected for β-actin) in cancer cell lines (lower panel).

Figure 17:
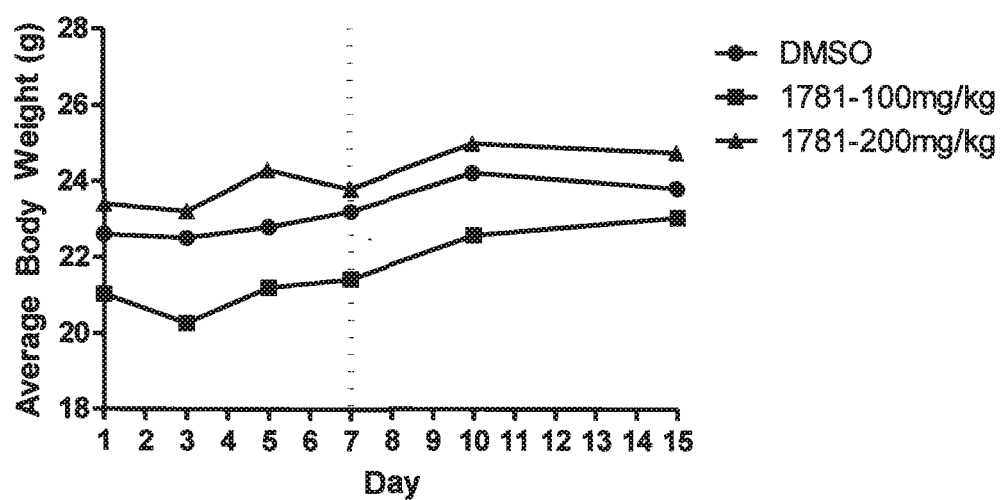

FIG. 17 depicts that active N,N'-diarylurea 1781 displays no apparent in vivo toxicity. Five female nude mice each were treated with 200 mg/kg, 100 mg/kg #1781 in 15 μl DMSO or 15 μl DMSO daily for seven days. Mice were observed daily for signs of toxicity and weighed every other day for total of 15 days and then necropsy was performed. The average body of each group is plotted against the time.

It will be recognized that the results and examples in the figures are only illustrative and other examples and illustrations will be readily recognized by the person of ordinary skill in the art, given the benefit of this disclosure.

DETAILED DESCRIPTION

In accordance with certain examples, compounds of Formula I and/or Formula II and/or Formula III and/or Formula IV inhibit translation (e.g., translation initiation). Such compounds are useful for the treatment of (1) proliferative disorders, (2) non-proliferative, degenerative disorders, (3) viral infections, and/or (4) disorders associated with viral infections. Certain examples are described below with reference to various chemical formulae. The chemical formulae referred to herein can exhibit the phenomena of tautomerism, conformational isomerism, stereo isomerism or geometric isomerism. As the formulae drawings within this specification can represent only one of the possible tautomeric, conformational isomeric, enantiomeric or geometric isomeric forms, it should be understood that the invention encompasses any tautomeric, conformational isomeric, enantiomeric or geometric isomeric forms which exhibit biological or pharmacological activity as described herein.

The compounds and compositions provided below are effective to inhibit translation (e.g., translation initiation) at least to the extent necessary for effective treatment of one or more disorders described herein. While in certain examples translation may be substantially inhibited such that little or no activity results, in other examples the inhibition is at least sufficient to relieve and or alleviate the symptoms from a selected disorder to be treated.

In accordance with certain embodiments, compounds of the invention are represented by the generic formula set forth below.

Formula I

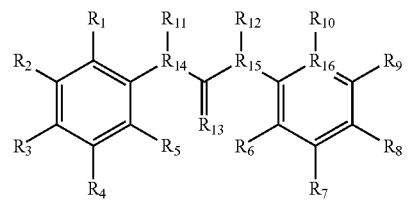

Formula II

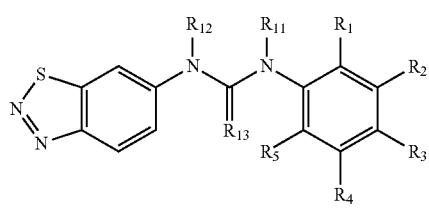

Formula III

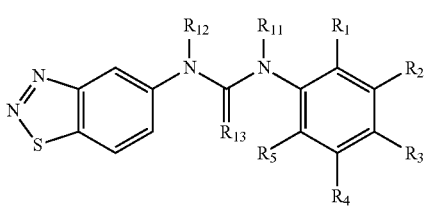

In certain exemplary embodiments with respect to Formula I, II or III, $R_1$ is H, Cl, $CH_3$, $OCH_3$, $NO_2$, OH, F, $CF_3$, $OCF_3$, Br, $CH_3S$, AcHN, $(CH_3)_2N$, $CO-NH-NH_2$, $SO_2NH_2$, $C(CH_3)_3$, $COOCH_2CH_3$, $COCH_3$, $O(CH_2)_2CH_3$, CHO, $CO_2H$, $OCONH_2$, CN, C≡CH, N-methylacetamido, 1-[1,2,3]triazolyl, 4-[1,2,3]triazolyl, 5-[1,2,3,4]tetrazolyl, guanidine, $C_{1-6}$-alkyl, $C_{1-6}$-alkyl amino substituted with: hydroxyl, $C_{1-6}$-alkoxy, amino, mono- and di-($C_{1-6}$-alkyl) amino, carboxy, $C_{1-6}$-alkylcarbonylamino, $C_{1-6}$-alkylaminocarbonyl, aminosulfonyl, mono- and di-($C_{1-6}$-alkyl)aminosulfonyl, carbamido, mono- and di-($C_{1-6}$-alkyl) aminocarbonylamino, halogen(s), aryl, arylheterocycle, heterocycle, and heteroaryl. $C_{2-6}$-alkenyl, $C_{1-6}$-alkoxy, $C_{2-6}$-alkenyloxy, $C_{1-6}$-alkoxycarbonyl, $C_{1-6}$-alkylcarbonyl, $C_{1-6}$-alkylcarbonyloxy, N,N-dimethylamino, N,N-di($C_{1-6}$-alkyl)amino, mono- and di-($C_{1-6}$-alkyl)aminocarbonyl, $C_{1-6}$-alkylcarbonylamino, $C_{1-6}$-alkylsulfonylamino, $C_{1-6}$-alkylthio, $C_{1-6}$-alkylsulphinyl, aryl, aryloxy, arylcarbonyl, arylamino, aryl sulfonylamino, hetrocyclyl, hetrocyclyloxy, heterocyclylamino, heterocyclylcarbonyl, heteroaryl, heteroaryloxy, heteroarylamino, heteroarylcarbonyl, heteroaryl sulfonylamino, $O-(CH_2)_{2-4}$-morpholino, $O-(CH_2)_{2-4}$-(piperazin-1-yl), $O-(CH_2)_{2-4}$-(4-methylpiperazin-1-yl), $O-(CH_2)_{2-4}$-mono- and di-($C_{1-6}$-alkyl)amino, $O-(CH_2)_{2-4}$-1H-[1,2,3]triazol-1-yl), $O-(CH_2)_{2-4}$-4(1H-[1,2,3]triazol-1-yl), $O-(CH_2)_{2-4}$-(4-($C_{1-6}$-alkyl)-1H-[1,2,3] triazol-1-yl), $O-(CH_2)_{2-4}$-4-(1-($C_{1-6}$-alkyl)-1H-[1,2,3]triazol-1-yl),

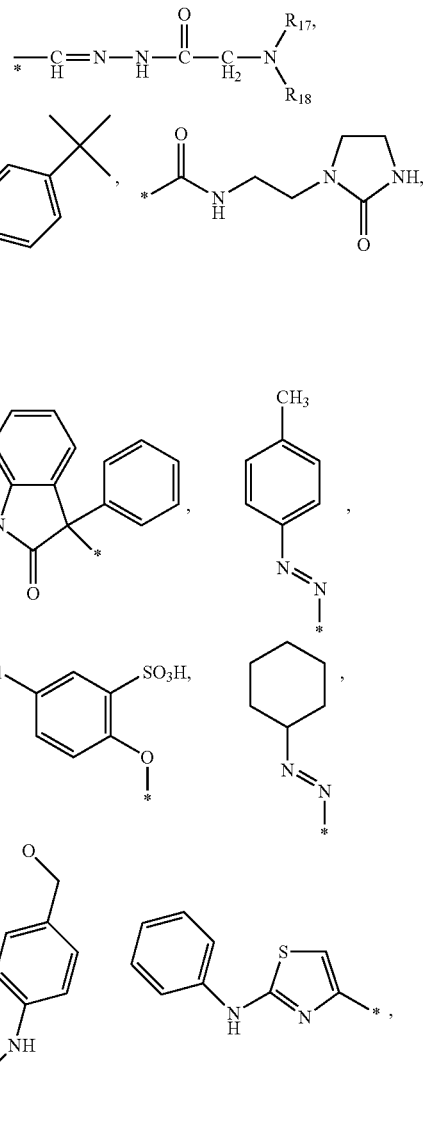

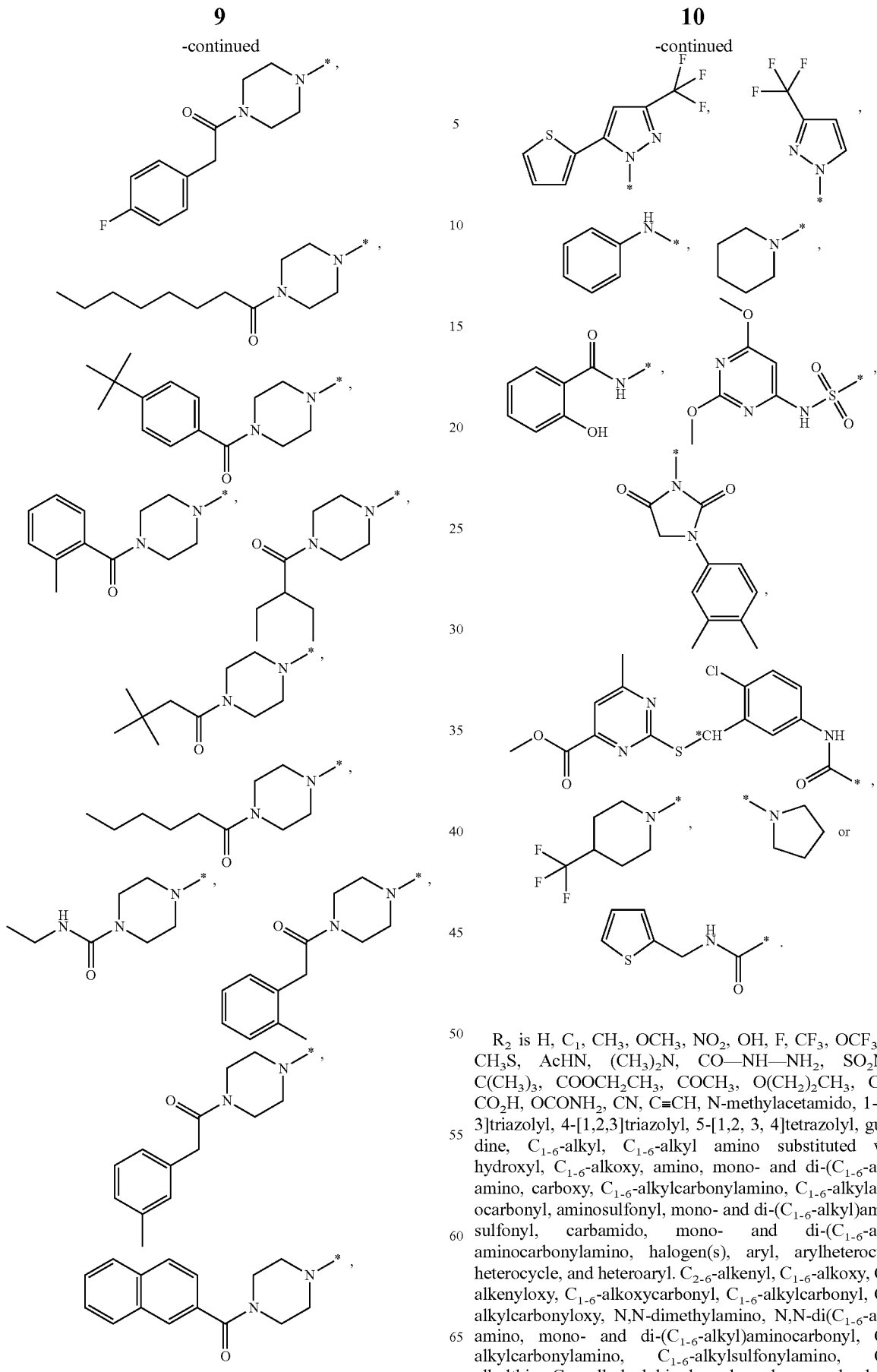

$R_2$ is H, $C_1$, $CH_3$, $OCH_3$, $NO_2$, OH, F, $CF_3$, $OCF_3$, Br, $CH_3S$, AcHN, $(CH_3)_2N$, CO—NH—$NH_2$, $SO_2NH_2$, $C(CH_3)_3$, $COOCH_2CH_3$, $COCH_3$, $O(CH_2)_2CH_3$, CHO, $CO_2H$, $OCONH_2$, CN, C≡CH, N-methylacetamido, 1-[1,2,3]triazolyl, 4-[1,2,3]triazolyl, 5-[1,2,3,4]tetrazolyl, guanidine, $C_{1-6}$-alkyl, $C_{1-6}$-alkyl amino substituted with: hydroxyl, $C_{1-6}$-alkoxy, amino, mono- and di-($C_{1-6}$-alkyl)amino, carboxy, $C_{1-6}$-alkylcarbonylamino, $C_{1-6}$-alkylaminocarbonyl, aminosulfonyl, mono- and di-($C_{1-6}$-alkyl)aminosulfonyl, carbamido, mono- and di-($C_{1-6}$-alkyl)aminocarbonylamino, halogen(s), aryl, arylheterocycle, heterocycle, and heteroaryl. $C_{2-6}$-alkenyl, $C_{1-6}$-alkoxy, $C_{2-6}$-alkenyloxy, $C_{1-6}$-alkoxycarbonyl, $C_{1-6}$-alkylcarbonyl, $C_{1-6}$-alkylcarbonyloxy, N,N-dimethylamino, N,N-di($C_{1-6}$-alkyl)amino, mono- and di-($C_{1-6}$-alkyl)aminocarbonyl, $C_{1-6}$-alkylcarbonylamino, $C_{1-6}$-alkylsulfonylamino, $C_{1-6}$-alkylthio, $C_{1-6}$-alkylsulphinyl, aryl, aryloxy, arylcarbonyl, arylamino, aryl sulfonylamino, hetrocyclyl, hetrocyclyloxy, heterocyclylamino, heterocyclylcarbonyl, heteroaryl, heteroaryloxy, heteroarylamino, heteroarylcarbonyl, heteroaryl sulfonylamino, O—$(CH_2)_{2-4}$-morpholino, O—$(CH_2)_{2-4}$-(piperazin-1-yl), O—$(CH_2)_{2-4}$-(4-methylpiperazin-1-yl), O—$(CH_2)_{2-4}$-mono- and di-($C_{1-6}$-alkyl)amino, O—$(CH_2)_{2-4}$-1H-[1,2,3]triazol-1-yl), O—$(CH_2)_{2-4}$-4(1H-[1,2,3]triazol-1-yl), O—$(CH_2)_{2-4}$-(4-($C_{1-6}$-alkyl)-1H-[1,2,3]triazol-1-yl), O—$(CH_2)_{2-4}$-4-(1-($C_{1-6}$-alkyl)-1H-[1,2,3]triazol-1-yl),

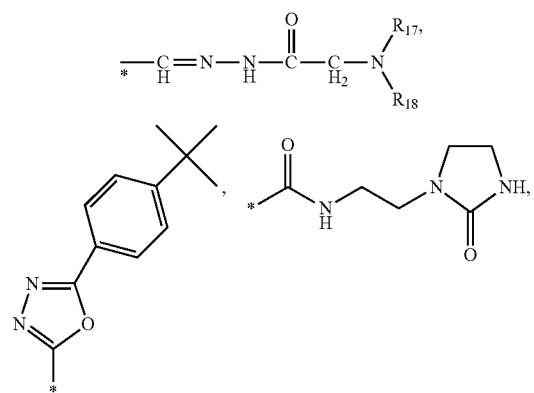

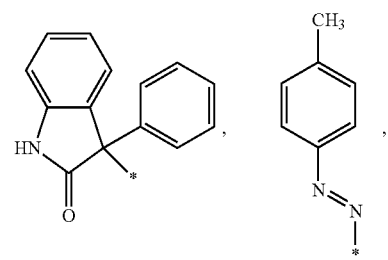

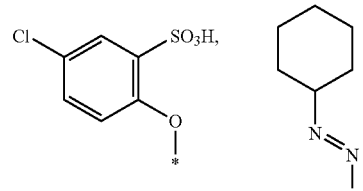

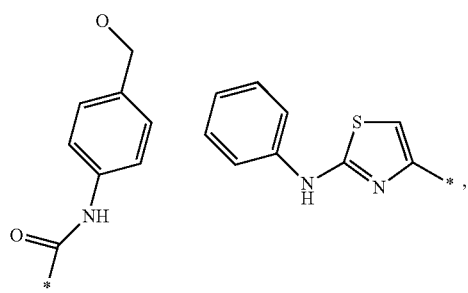

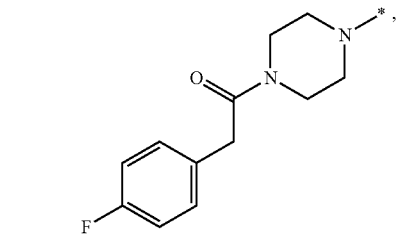

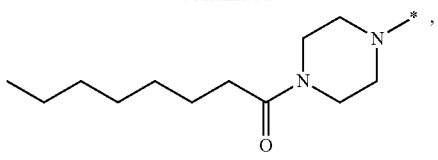

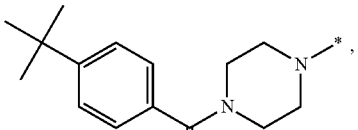

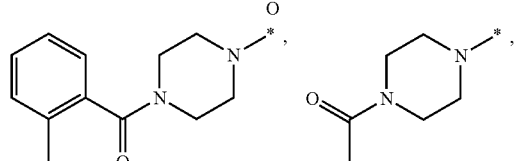

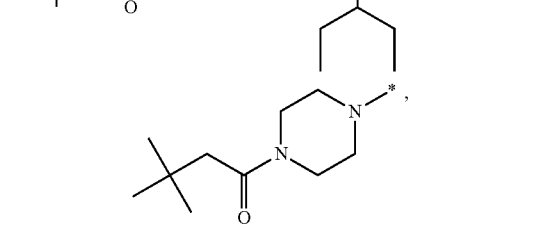

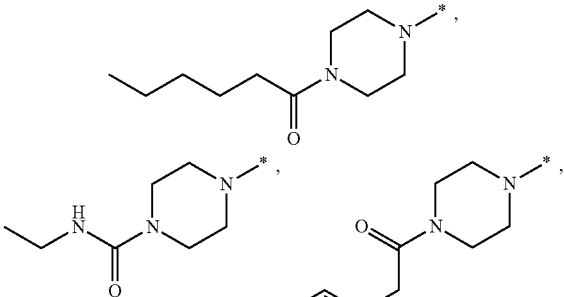

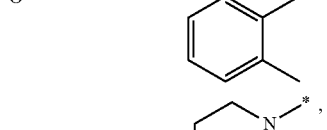

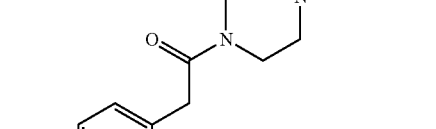

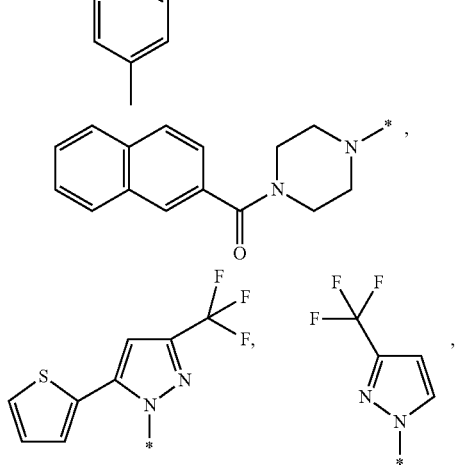

-continued

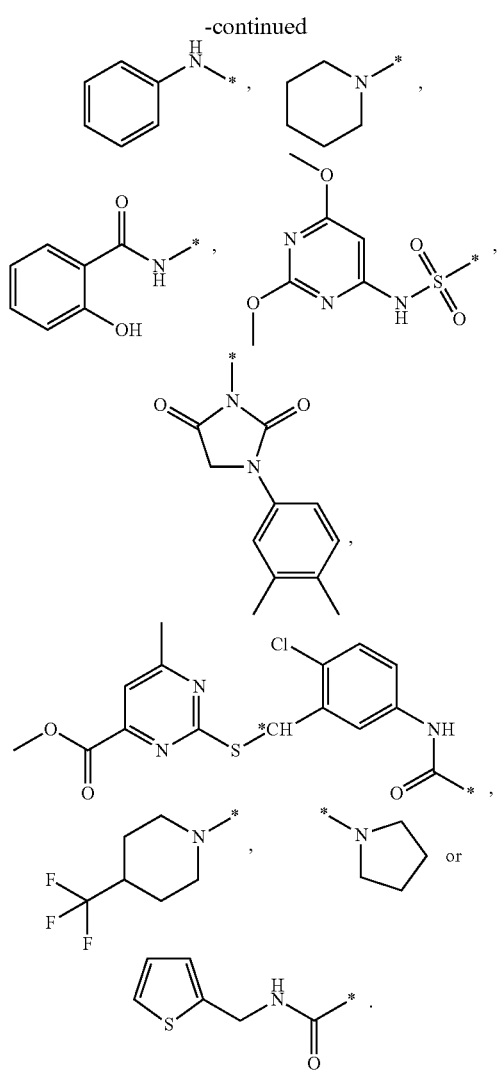

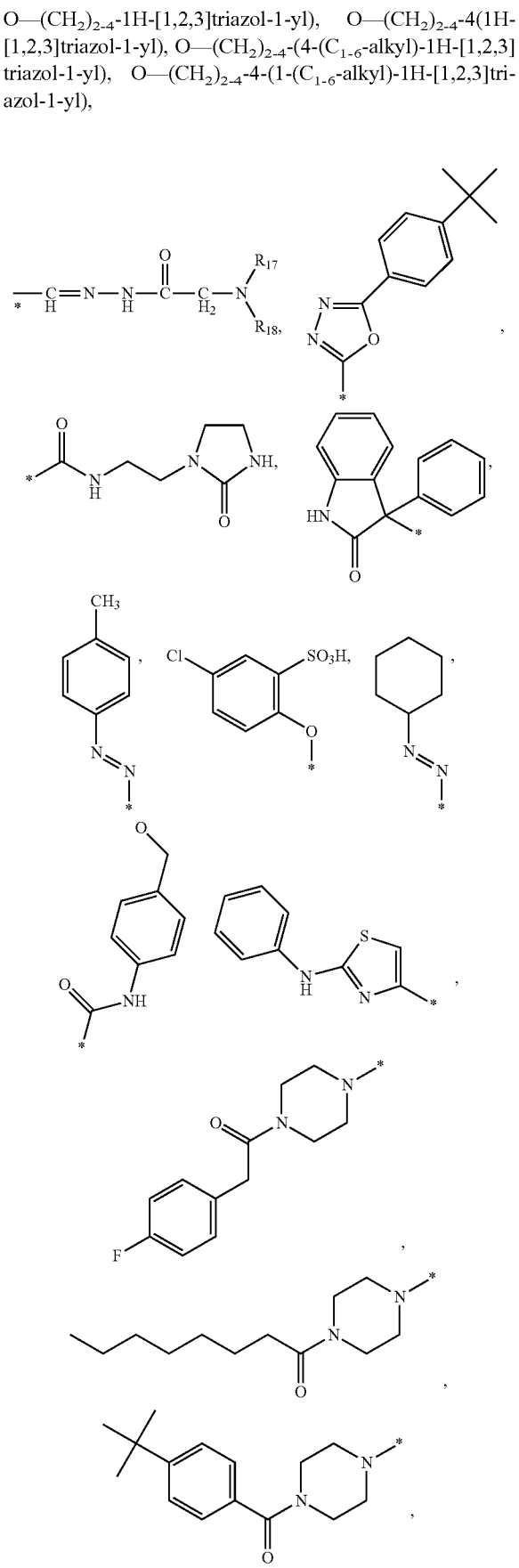

O—(CH$_2$)$_{2-4}$-1H-[1,2,3]triazol-1-yl), O—(CH$_2$)$_{2-4}$-4(1H-[1,2,3]triazol-1-yl), O—(CH$_2$)$_{2-4}$-(4-(C$_{1-6}$-alkyl)-1H-[1,2,3]triazol-1-yl), O—(CH$_2$)$_{2-4}$-4-(1-(C$_{1-6}$-alkyl)-1H-[1,2,3]triazol-1-yl), R$_3$ is H, Cl, CH$_3$, OCH$_3$, NO$_2$, OH, F, CF$_3$, OCF$_3$, Br, CH$_3$S, AcHN, (CH$_3$)$_2$N, CO—NH—NH$_2$, SO$_2$NH$_2$, C(CH$_3$)$_3$, COOCH$_2$CH$_3$, COCH$_3$, O(CH$_2$)$_2$CH$_3$, CHO, CO$_2$H, OCONH$_2$, CN, C≡CH, N-methylacetamido, 1-[1,2,3]triazolyl, 4-[1,2,3]triazolyl, 5-[1,2,3,4]tetrazolyl, guanidine, C$_{1-6}$-alkyl, C$_{1-6}$-alkyl amino substituted with: hydroxyl, C$_{1-6}$-alkoxy, amino, mono- and di-(C$_{1-6}$-alkyl) amino, carboxy, C$_{1-6}$-alkylcarbonylamino, C$_{1-6}$-alkylaminocarbonyl, aminosulfonyl, mono- and di-(C$_{1-6}$-alkyl)aminosulfonyl, carbamido, mono- and di-(C$_{1-6}$-alkyl)aminocarbonylamino, halogen(s), aryl, arylheterocycle, heterocycle, and heteroaryl. C$_{2-6}$-alkenyl, C$_{1-6}$-alkoxy, C$_{2-6}$-alkenyloxy, C$_{1-6}$-alkoxycarbonyl, C$_{1-6}$-alkylcarbonyl, C$_{1-6}$-alkylcarbonyloxy, N,N-dimethylamino, N,N-di((C$_{1-6}$-alkyl) amino, mono- and di-(C$_{1-6}$-alkyl)aminocarbonyl, C$_{1-6}$-alkylcarbonylamino, C$_{1-6}$-alkylsulfonylamino, C$_{1-6}$-alkylthio, C$_{1-6}$-alkylsulphinyl, aryl, aryloxy, arylcarbonyl, arylamino, arylsulfonylamino, hetrocyclyl, hetrocyclyloxy, heterocyclylamino, heterocyclylcarbonyl, heteroaryl, heteroaryloxy, heteroarylamino, heteroarylcarbonyl, heteroarylsulfonylamino, O—(CH$_2$)$_{2-4}$-morpholino, O—(CH$_2$)$_{2-4}$-(piperazin-1-yl), O—(CH$_2$)$_{2-4}$-(4-methylpiperazin-1-yl), O—(CH$_2$)$_{2-4}$-mono- and di-(C$_{1-6}$-alkyl)amino,

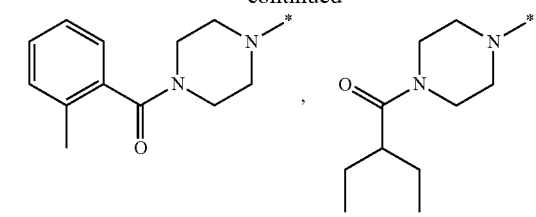

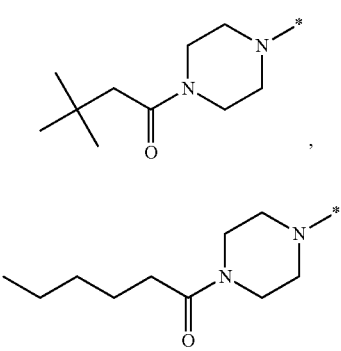

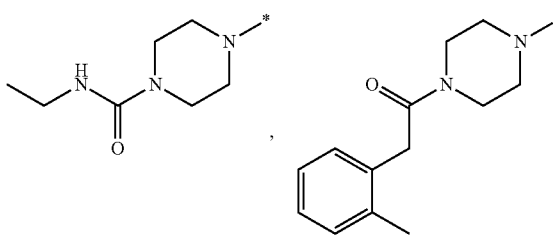

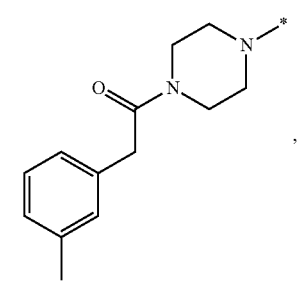

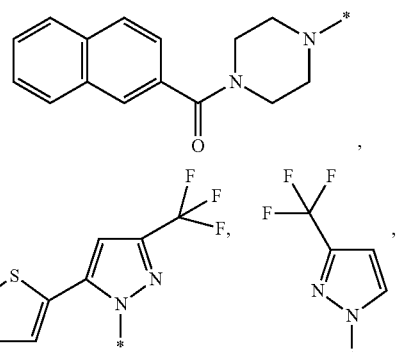

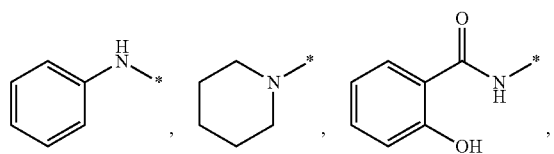

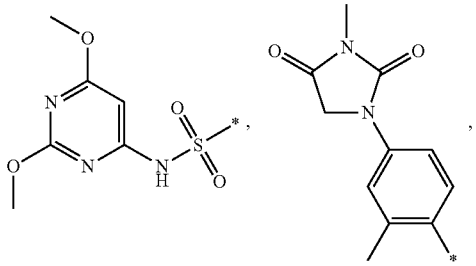

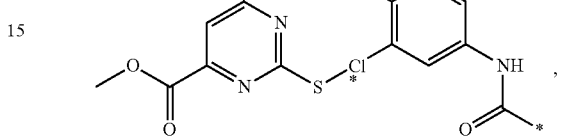

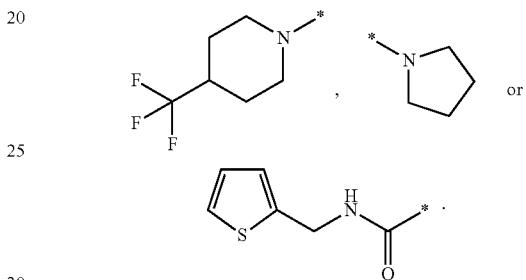

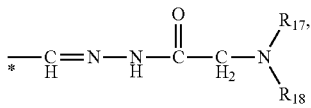

$R_4$ is H, Cl, $CH_3$, $OCH_3$, $NO_2$, OH, F, $CF_3$, $OCF_3$, Br, $CH_3S$, AcHN, $(CH_3)_2N$, CO—NH—$NH_2$, $SO_2NH_2$, $C(CH_3)_3$, $COOCH_2CH_3$, $COCH_3$, $O(CH_2)_2CH_3$, CHO, $CO_2H$, $OCONH_2$, CN, C≡CH, N-methylacetamido, 1-[1,2,3]triazolyl, 4-[1,2,3]triazolyl, 5-[1,2,3,4]tetrazolyl, guanidine, $C_{1-6}$-alkyl, $C_{1-6}$-alkyl amino substituted with: hydroxyl, $C_{1-6}$-alkoxy, amino, mono- and di-($C_{1-6}$-alkyl) amino, carboxy, $C_{1-6}$-alkylcarbonylamino, $C_{1-6}$-alkylaminocarbonyl, aminosulfonyl, mono- and di-($C_{1-6}$-alkyl)aminosulfonyl, carbamido, mono- and di-($C_{1-6}$-alkyl) aminocarbonylamino, halogen(s), aryl, arylheterocycle, heterocycle, and heteroaryl. $C_{2-6}$-alkenyl, $C_{1-6}$-alkoxy, $C_{2-6}$-alkenyloxy, $C_{1-6}$-alkoxycarbonyl, $C_{1-6}$-alkylcarbonyl, $C_{1-6}$-alkylcarbonyloxy, N,N-dimethylamino, N,N-di($C_{1-6}$-alkyl) amino, mono- and di-($C_{1-6}$-alkyl)aminocarbonyl, $C_{1-6}$-alkylcarbonylamino, $C_{1-6}$-alkylsulfonylamino, $C_{1-6}$-alkylthio, $C_{1-6}$-alkylsulphinyl, aryl, aryloxy, arylcarbonyl, arylamino, aryl sulfonylamino, hetrocyclyl, hetrocyclyloxy, heterocyclylamino, heterocyclylcarbonyl, heteroaryl, heteroaryloxy, heteroarylamino, heteroarylcarbonyl, heteroaryl sulfonylamino, O—$(CH_2)_{2-4}$-morpholino, O—$(CH_2)_{2-4}$-(piperazin-1-yl), O—$(CH_2)_{2-4}$-(4-methylpiperazin-1-yl), O—$(CH_2)_{2-4}$-mono- and di-($C_{1-6}$-alkyl)amino, O—$(CH_2)_{2-4}$-1H-[1,2,3]triazol-1-yl), O—$(CH_2)_{2-4}$-4(1H-[1,2,3]triazol-1-yl), O—$(CH_2)_{2-4}$-(4-($C_{1-6}$-alkyl)-1H-[1,2,3]triazol-1-yl), O—$(CH_2)_{2-4}$-4-(1-(($C_{1-6}$-alkyl)-1H-[1,2,3]triazol-1-yl), -continued

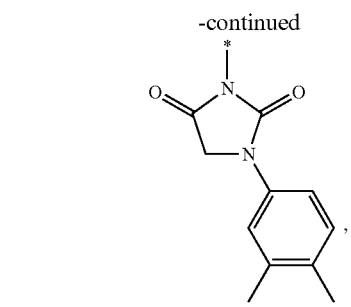

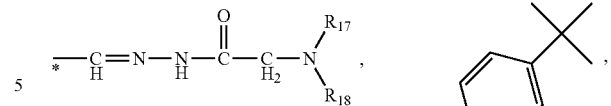

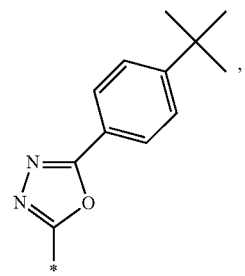

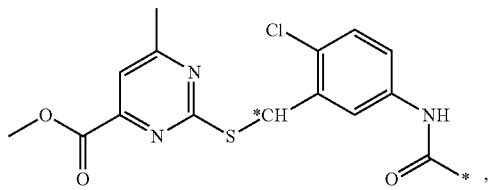

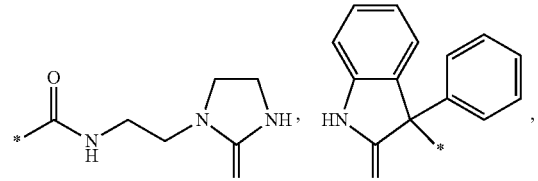

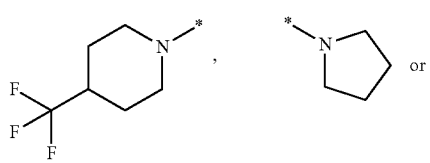

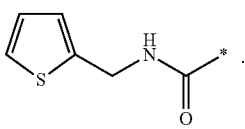

or

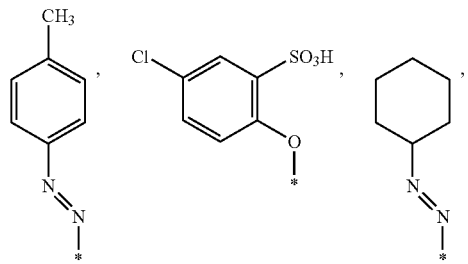

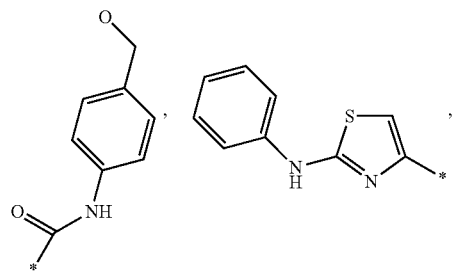

$R_5$ is H, Cl, $CH_3$, $OCH_3$, $NO_2$, OH, F, $CF_3$, $OCF_3$, Br, $CH_3S$, AcHN, $(CH_3)_2N$, CO—NH—$NH_2$, $SO_2NH_2$, $C(CH_3)_3$, $COOCH_2CH_3$, $COCH_3$, $O(CH_2)_2CH_3$, CHO, $CO_2H$, $OCONH_2$, CN, C≡CH, N-methylacetamido, 1-[1,2,3]triazolyl, 4-[1,2,3]triazolyl, 5-[1,2,3,4]tetrazolyl, guanidine, $C_{1-6}$-alkyl, $C_{1-6}$-alkyl amino substituted with: hydroxyl, $C_{1-6}$-alkoxy, amino, mono- and di-($C_{1-6}$-alkyl) amino, carboxy, $C_{1-6}$-alkylcarbonylamino, $C_{1-6}$-alkylaminocarbonyl, aminosulfonyl, mono- and di-($C_{1-6}$-alkyl)aminosulfonyl, carbamido, mono- and di-($C_{1-6}$-alkyl) aminocarbonylamino, halogen(s), aryl, arylheterocycle, heterocycle, and heteroaryl. $C_{2-6}$-alkenyl, $C_{1-6}$-alkoxy, $C_{2-6}$-alkenyloxy, $C_{1-6}$-alkoxycarbonyl, $C_{1-6}$-alkylcarbonyl, $C_{1-6}$-alkylcarbonyloxy, N,N-dimethylamino, N,N-di($C_{1-6}$-alkyl) amino, mono- and di-($C_{1-6}$-alkyl)aminocarbonyl, $C_{1-6}$-alkylcarbonylamino, $C_{1-6}$-alkylsulfonylamino, $C_{1-6}$-alkylthio, $C_{1-6}$-alkylsulphinyl, aryl, aryloxy, arylcarbonyl, arylamino, arylsulfonylamino, hetrocyclyl, hetrocyclyloxy, heterocyclylamino, heterocyclylcarbonyl, heteroaryl, heteroaryloxy, heteroarylamino, heteroarylcarbonyl, heteroarylsulfonylamino, O—$(CH_2)_{2-4}$-morpholino, O—$(CH_2)_{2-4}$-(piperazin-1-yl), O—$(CH_2)_{2-4}$-(4-methylpiperazin-1-yl), O—$(CH_2)_{2-4}$-mono- and di-($C_{1-6}$-alkyl)amino, O—$(CH_2)_{2-4}$-1H-[1,2,3]triazol-1-yl), O—$(CH_2)_{2-4}$-4(1H-[1,2,3]triazol-1-yl), O—$(CH_2)_{2-4}$-(4-($C_{1-6}$-alkyl)-1H-[1,2,3]triazol-1-yl), O—$(CH_2)_{2-4}$-4-(1-($C_{1-6}$-alkyl)-1H-[1,2,3]triazol-1-yl),

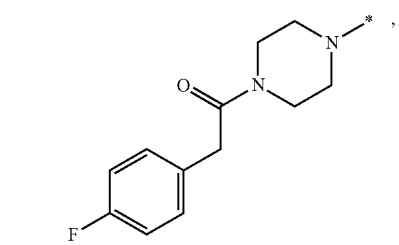

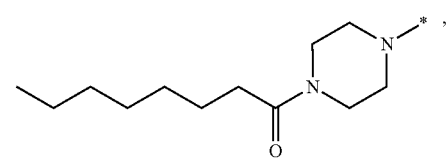

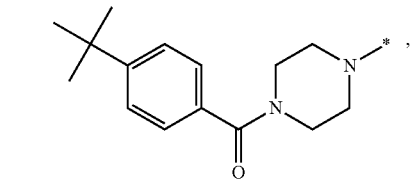

-continued

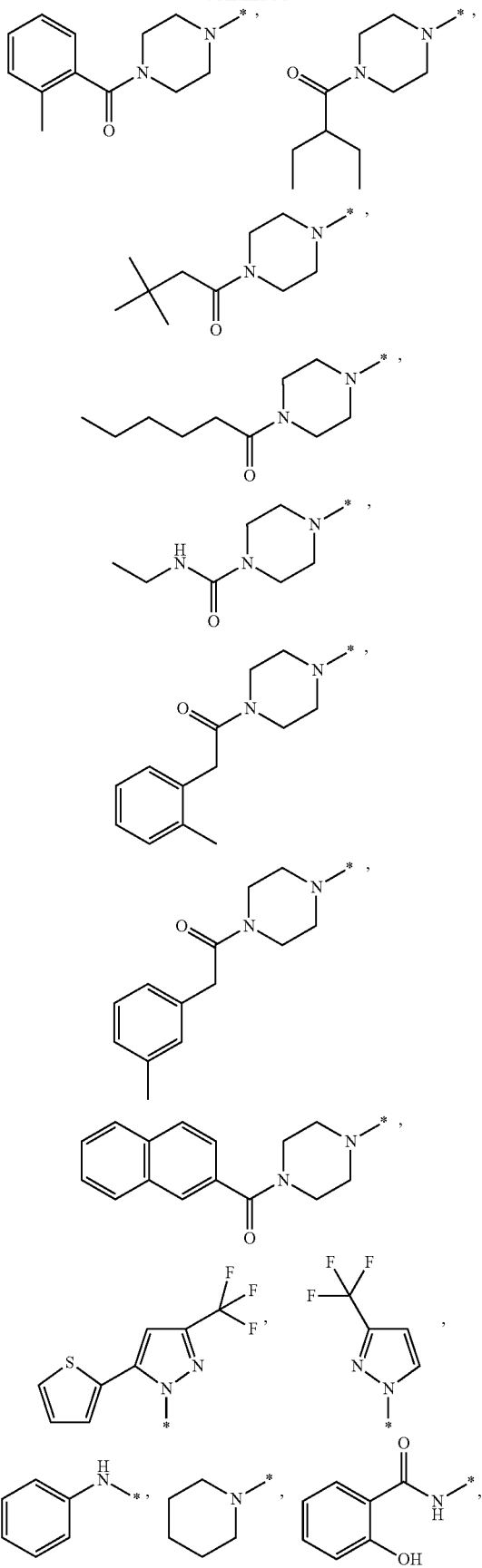

-continued

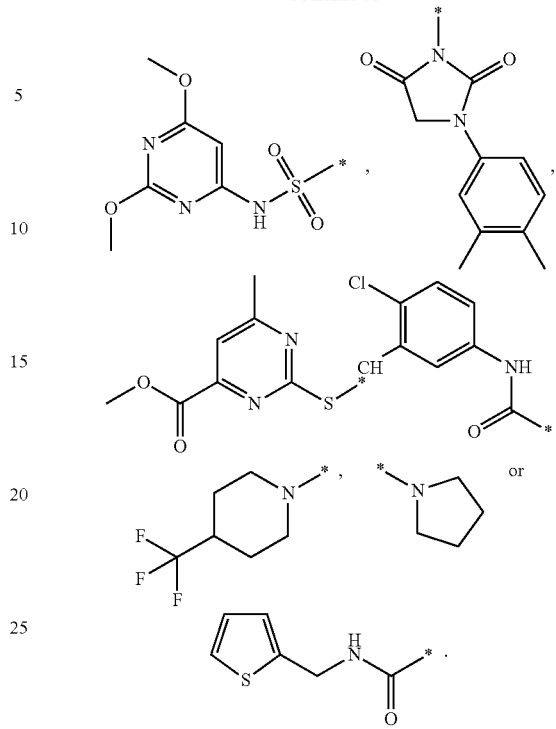

$R_6$ is H, Cl, $CH_3$, $OCH_3$, $NO_2$, OH, F, $CF_3$, $OCF_3$, Br, $CH_3S$, AcHN, $(CH_3)_2N$, CO—NH—$NH_2$, $SO_2NH_2$, $C(CH_3)_3$, $COOCH_2CH_3$, $COCH_3$, $O(CH_2)_2CH_3$, CHO, $CO_2H$, $OCONH_2$, CN, C≡CH, N-methylacetamido, 1-[1,2,3]triazolyl, 4-[1,2,3]triazolyl, 5-[1,2,3,4]tetrazolyl, guanidine, $C_{1-6}$-alkyl, $C_{1-6}$-alkyl amino substituted with: hydroxyl, $C_{1-6}$-alkoxy, amino, mono- and di-($C_{1-6}$-alkyl) amino, carboxy, $C_{1-6}$-alkylcarbonylamino, $C_{1-6}$-alkylaminocarbonyl, aminosulfonyl, mono- and di-($C_{1-6}$-alkyl)aminosulfonyl, carbamido, mono- and di-($C_{1-6}$-alkyl)aminocarbonylamino, halogen(s), aryl, arylheterocycle, heterocycle, and heteroaryl. $C_{2-6}$-alkenyl, $C_{1-6}$-alkoxy, $C_{2-6}$-alkenyloxy, $C_{1-6}$-alkoxycarbonyl, $C_{1-6}$-alkylcarbonyl, $C_{1-6}$-alkylcarbonyloxy, N,N-dimethylamino, N,N-di($C_{1-6}$-alkyl) amino, mono- and di-($C_{1-6}$-alkyl)aminocarbonyl, $C_{1-6}$-alkylcarbonylamino, $C_{1-6}$-alkylsulfonylamino, $C_{1-6}$-alkylthio, $C_{1-6}$-alkylsulphinyl, aryl, aryloxy, arylcarbonyl, arylamino, aryl sulfonylamino, hetrocyclyl, hetrocyclyloxy, heterocyclylamino, heterocyclylcarbonyl, heteroaryl, heteroaryloxy, heteroarylamino, heteroarylcarbonyl, heteroaryl sulfonylamino, O—$(CH_2)_{2-4}$-morpholino, O—$(CH_2)_{2-4}$-(piperazin-1-yl), O—$(CH_2)_{2-4}$-(4-methylpiperazin-1-yl), O—$(CH_2)_{2-4}$-mono- and di-($C_{1-6}$-alkyl)amino, O—$(CH_2)_{2-4}$-1H-[1,2,3]triazol-1-yl), O—$(CH_2)_{2-4}$-4(1H-[1,2,3]triazol-1-yl), O—$(CH_2)_{2-4}$-(4-($C_{1-6}$-alkyl)-1H-[1,2,3] triazol-1-yl), O—$(CH_2)_{2-4}$-4-(1-($C_{1-6}$-alkyl)-1H-[1,2,3]triazol-1-yl),

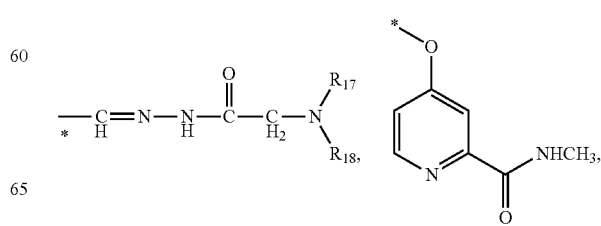

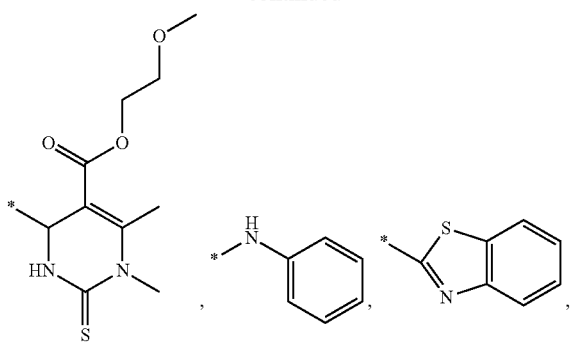

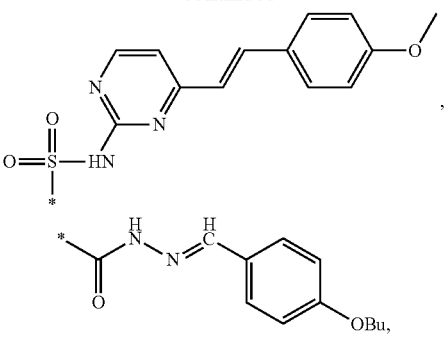

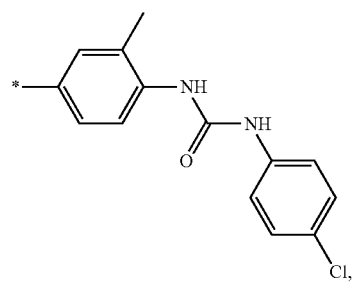

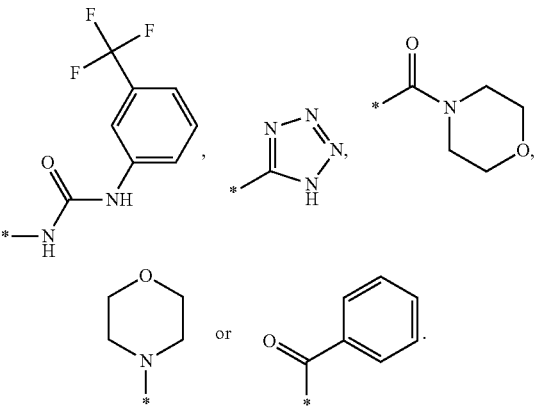

R$_7$ is H, Cl, CH$_3$, OCH$_3$, NO$_2$, OH, F, CF$_3$, OCF$_3$, Br, CH$_3$S, AcHN, (CH$_3$)$_2$N, CO—NH—NH$_2$, SO$_2$NH$_2$, C(CH$_3$)$_3$, COOCH$_2$CH$_3$, COCH$_3$, O(CH$_2$)$_2$CH$_3$, CHO, CO$_2$H, OCONH$_2$, CN, C≡CH, N-methylacetamido, 1-[1,2,3]triazolyl, 4-[1,2,3]triazolyl, 5-[1,2,3,4]tetrazolyl, guanidine, C$_{1-6}$-alkyl, C$_{1-6}$-alkyl amino substituted with: hydroxyl, C$_{1-6}$-alkoxy, amino, mono- and di-(C$_{1-6}$-alkyl)amino, carboxy, C$_{1-6}$-alkylcarbonylamino, C$_{1-6}$-alkylaminocarbonyl, aminosulfonyl, mono- and di-(C$_{1-6}$-alkyl)aminosulfonyl, carbamido, mono- and di-(C$_{1-6}$-alkyl)aminocarbonylamino, halogen(s), aryl, arylheterocycle, heterocycle, and heteroaryl. C$_{2-6}$-alkenyl, C$_{1-6}$-alkoxy, C$_{2-6}$-alkenyloxy, C$_{1-6}$-alkoxycarbonyl, C$_{1-6}$-alkylcarbonyl, C$_{1-6}$-alkylcarbonyloxy, N,N-dimethylamino, N,N-di(C$_{1-6}$-alkyl)amino, mono- and di-(C$_{1-6}$-alkyl)aminocarbonyl, C$_{1-6}$-alkylcarbonylamino, C$_{1-6}$-alkylsulfonylamino, C$_{1-6}$-alkylthio, C$_{1-6}$-alkylsulphinyl, aryl, aryloxy, arylcarbonyl, arylamino, aryl sulfonylamino, hetrocyclyl, hetrocyclyloxy, heterocyclylamino, heterocyclylcarbonyl, heteroaryl, heteroaryloxy, heteroarylamino, heteroarylcarbonyl, heteroaryl sulfonylamino, O—(CH$_2$)$_{2-4}$-morpholino, O—(CH$_2$)$_{2-4}$-(piperazin-1-yl), O—(CH$_2$)$_{2-4}$-(4-methylpiperazin-1-yl), O—(CH$_2$)$_{2-4}$-mono- and di-(C$_{1-6}$-alkyl)amino, O—(CH$_2$)$_{2-4}$-1H-[1,2,3]triazol-1-yl), O—(CH$_2$)$_{2-4}$-4(1H-[1,2,3]triazol-1-yl), O—(CH$_2$)$_{2-4}$-(4-(C$_{1-6}$-alkyl)-1H-[1,2,3]triazol-1-yl), O—(CH$_2$)$_{2-4}$-4-(1-(C$_{1-6}$-alkyl)-1H-[1,2,3]triazol-1-yl),

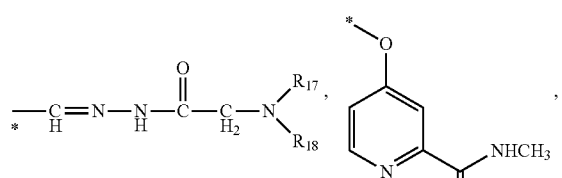
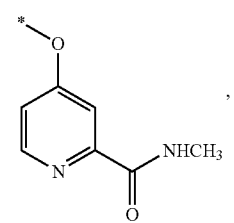
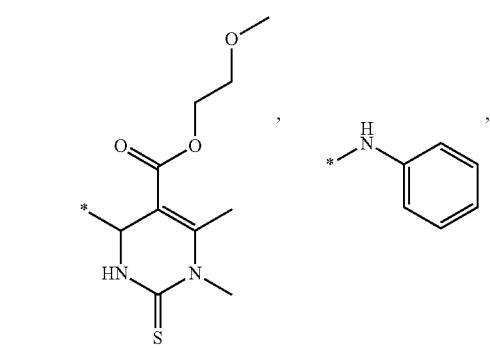
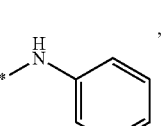
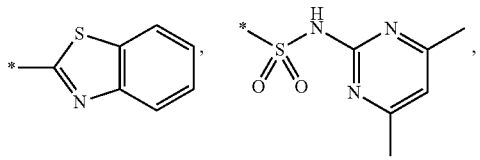
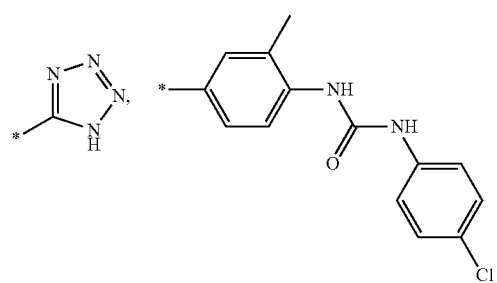
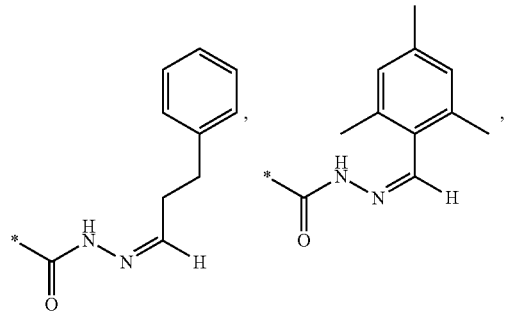
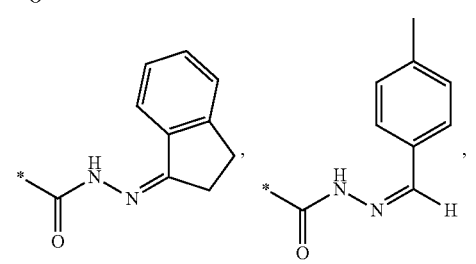

-continued

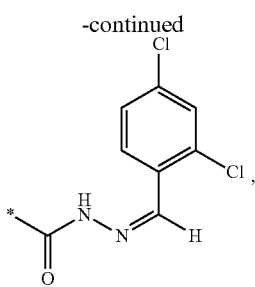
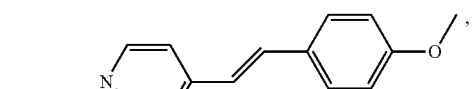
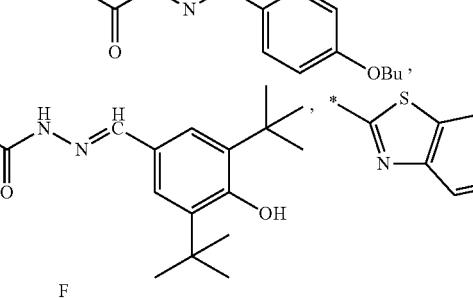

$R_8$ is H, Cl, $CH_3$, $OCH_3$, $NO_2$, OH, F, $CF_3$, $OCF_3$, Br, $CH_3S$, AcHN, $(CH_3)_2N$, CO—NH—$NH_2$, $SO_2NH_2$, $C(CH_3)_3$, $COOCH_2CH_3$, $COCH_3$, $O(CH_2)_2CH_3$, CHO, $CO_2H$, $OCONH_2$, CN, C≡CH, N-methylacetamido, 1-[1,2,3]triazolyl, 4-[1,2,3]triazolyl, 5-[1,2,3,4]tetrazolyl, guanidine, $C_{1-6}$-alkyl, $C_{1-6}$-alkyl amino substituted with: hydroxyl, $C_{1-6}$-alkoxy, amino, mono- and di-($C_{1-6}$-alkyl) amino, carboxy, $C_{1-6}$-alkylcarbonylamino, $C_{1-6}$-alkylaminocarbonyl, aminosulfonyl, mono- and di-($C_{1-6}$-alkyl)aminosulfonyl, carbamido, mono- and di-($C_{1-6}$-alkyl) aminocarbonylamino, halogen(s), aryl, arylheterocycle, heterocycle, and heteroaryl. $C_{2-6}$-alkenyl, $C_{1-6}$-alkoxy, $C_{2-6}$-alkenyloxy, $C_{1-6}$-alkoxycarbonyl, $C_{1-6}$-alkylcarbonyl, $C_{1-6}$-alkylcarbonyloxy, N,N-dimethylamino, N,N-di($C_{1-6}$-alkyl) amino, mono- and di-($C_{1-6}$-alkyl)aminocarbonyl, $C_{1-6}$-alkylcarbonylamino, $C_{1-6}$-alkylsulfonylamino, $C_{1-6}$-alkylthio, $C_{1-6}$-alkylsulphinyl, aryl, aryloxy, arylcarbonyl, arylamino, arylsulfonylamino, hetrocyclyl, hetrocyclyloxy, heterocyclylamino, heterocyclylcarbonyl, heteroaryl, heteroaryloxy, heteroarylamino, heteroarylcarbonyl, heteroar ylsulfonyl amino, O—(CH$_2$)$_{2-4}$-morpholino, O—(CH$_2$)$_{2-4}$-(piperazin-1-yl), O—(CH$_2$)$_{2-4}$-(4-methylpiperazin-1-yl), O—(CH$_2$)$_{2-4}$-mono- and di-(C$_{1-6}$-alkyl)amino, O—(CH$_2$)$_{2-4}$-1H-[1,2,3]triazol-1-yl), O—(CH$_2$)$_{2-4}$-4(1H-[1,2,3]triazol-1-yl), O—(CH$_2$)$_{2-4}$-(4-(C$_{1-6}$-alkyl)-1H-[1,2,3]triazol-1-yl), O—(CH$_2$)$_{2-4}$-4-(1-(C$_{1-6}$-alkyl)-1H-[1,2,3]triazol-1-yl),

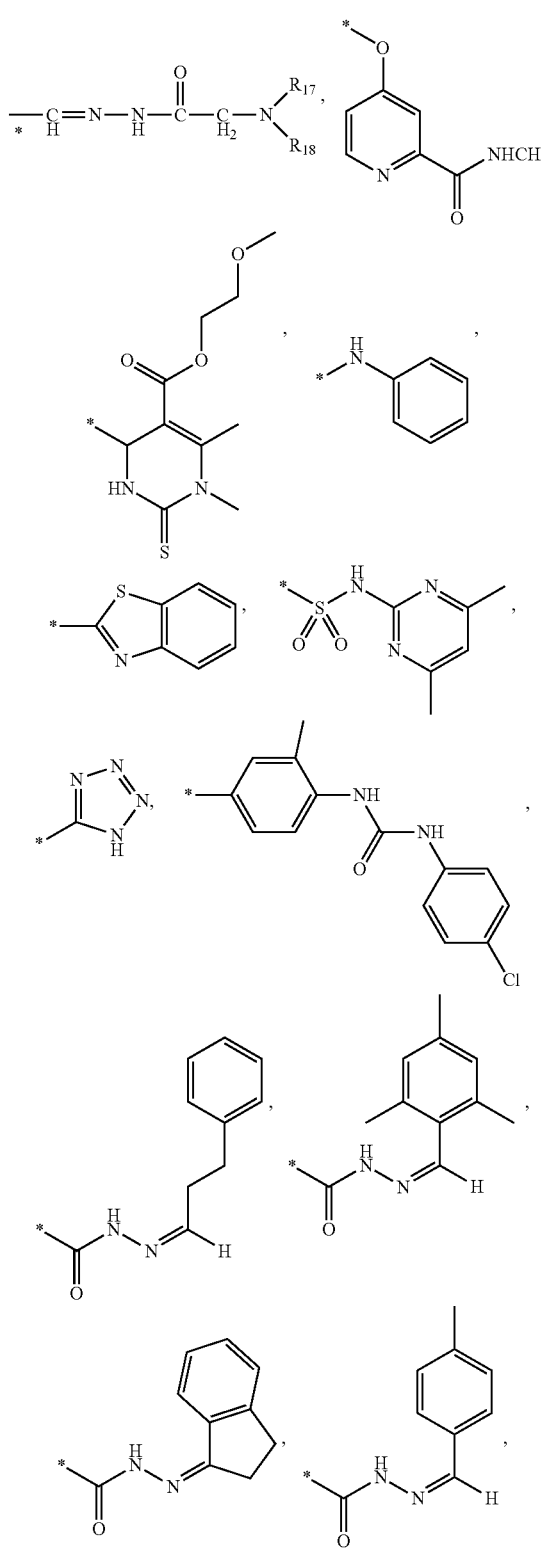

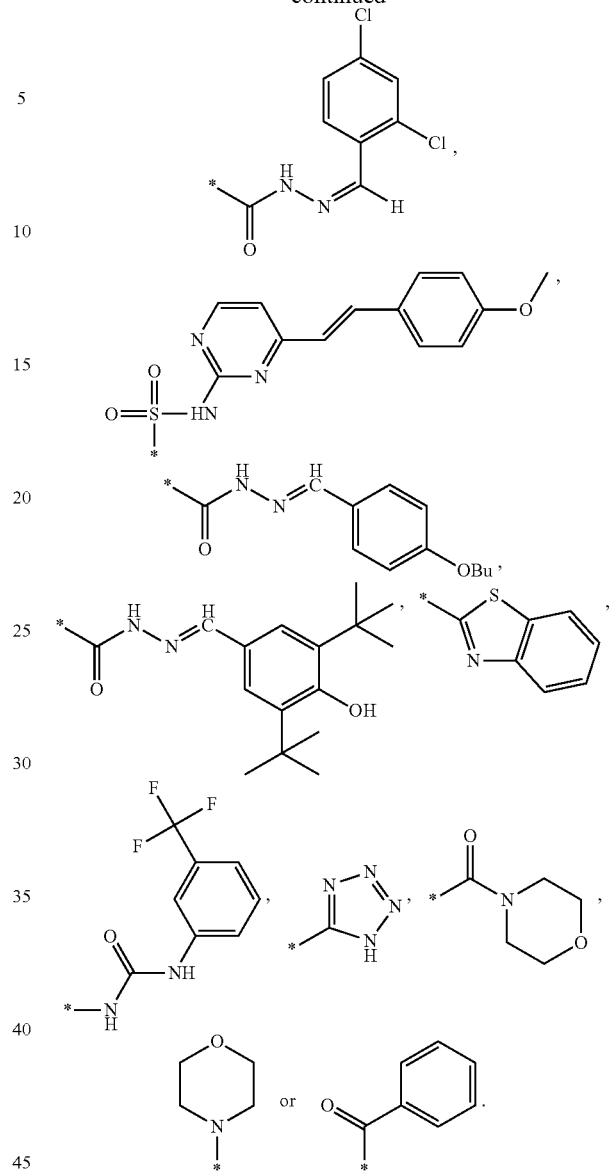

R$_9$ is H, C$_1$, CH$_3$, OCH$_3$, NO$_2$, OH, F, CF$_3$, OCF$_3$, Br, CH$_3$S, AcHN, (CH$_3$)$_2$N, CO—NH—NH$_2$, SO$_2$NH$_2$, C(CH$_3$)$_3$, COOCH$_2$CH$_3$, COCH$_3$, O(CH$_2$)$_2$CH$_3$, CHO, CO$_2$H, OCONH$_2$, CN, C≡CH, N-methylacetamido, 1-[1,2,3]triazolyl, 4-[1,2,3]triazolyl, 5-[1,2,3,4]tetrazolyl, guanidine, C$_{1-6}$-alkyl, C$_{1-6}$-alkyl amino substituted with: hydroxyl, C$_{1-6}$-alkoxy, amino, mono- and di-(C$_{1-6}$-alkyl) amino, carboxy, C$_{1-6}$-alkylcarbonylamino, C$_{1-6}$-alkylaminocarbonyl, aminosulfonyl, mono- and di-(C$_{1-6}$-alkyl)aminosulfonyl, carbamido, mono- and di-(C$_{1-6}$-alkyl) aminocarbonylamino, halogen(s), aryl, arylheterocycle, heterocycle, and heteroaryl. C$_{2-6}$-alkenyl, C$_{1-6}$-alkoxy, C$_{2-6}$-alkenyloxy, C$_{1-6}$-alkoxycarbonyl, C$_{1-6}$-alkylcarbonyl, C$_{1-6}$-alkylcarbonyloxy, N,N-dimethylamino, N,N-di(C$_{1-6}$-alkyl) amino, mono- and di-(C$_{1-6}$-alkyl)aminocarbonyl, C$_{1-6}$-alkylcarbonylamino, C$_{1-6}$-alkylsulfonylamino, C$_{1-6}$-alkylthio, C$_{1-6}$-alkylsulphinyl, aryl, aryloxy, arylcarbonyl, arylamino, arylsulfonylamino, hetrocyclyl, hetrocyclyloxy, heterocyclylamino, heterocyclylcarbonyl, heteroaryl, heteroaryloxy, heteroarylamino, heteroarylcarbonyl, heteroar ylsulfonylamino, O—(CH₂)₂₋₄-morpholino, O—(CH₂)₂₋₄-(piperazin-1-yl), O—(CH₂)₂₋₄-(4-methylpiperazin-1-yl), O—(CH₂)₂₋₄-mono- and di-(C₁₋₆-alkyl)amino, O—(CH₂)₂₋₄-1H-[1,2,3]triazol-1-yl), O—(CH₂)₂₋₄-4(1H-[1,2,3]triazol-1-yl), O—(CH₂)₂₋₄-(4-(C₁₋₆-alkyl)-1H-[1,2,3]triazol-1-yl), O—(CH₂)₂₋₄-4-(1-(C₁₋₆-alkyl)-1H-[1,2,3]triazol-1-yl),

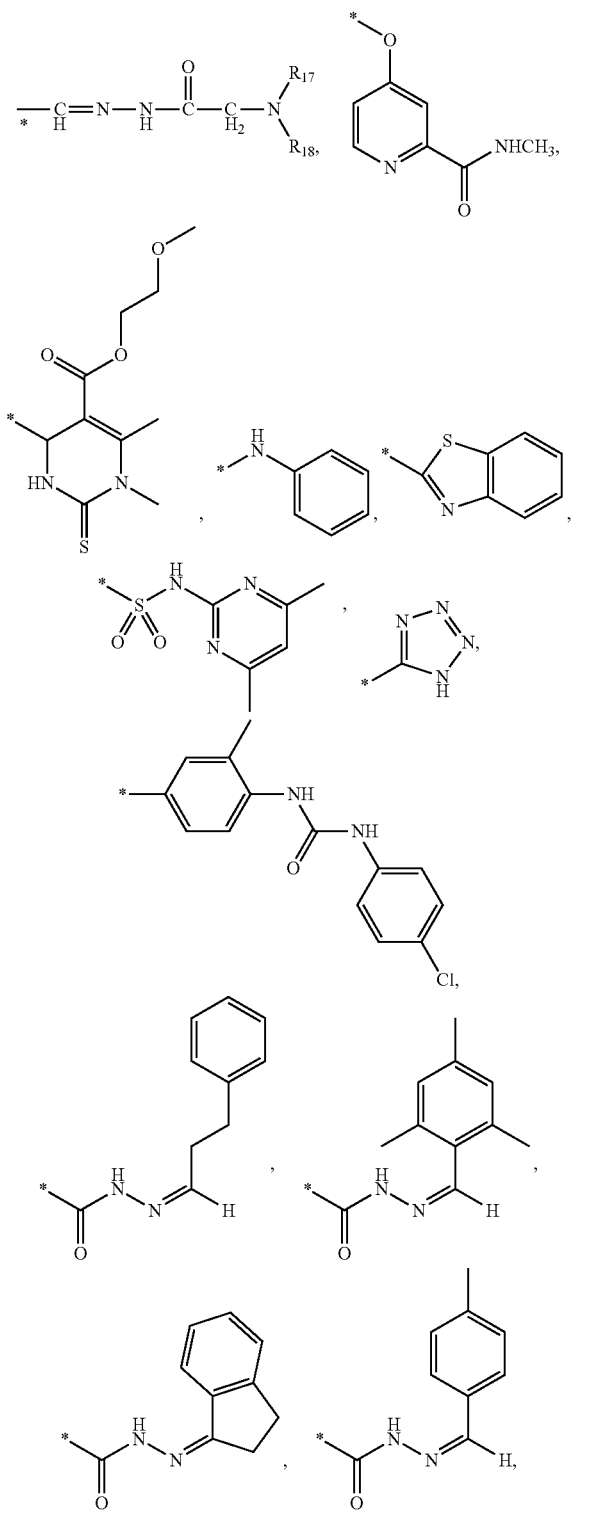

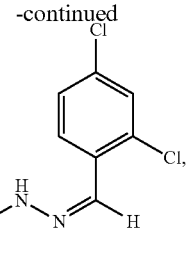

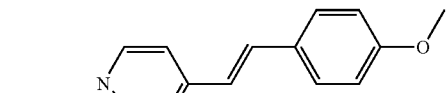

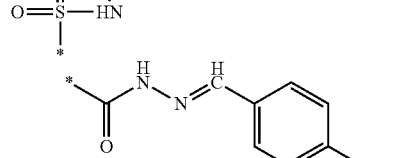

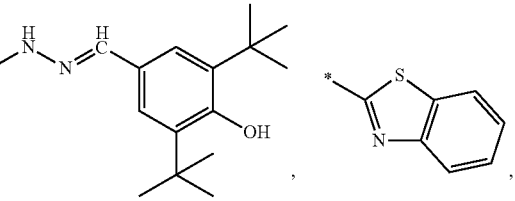

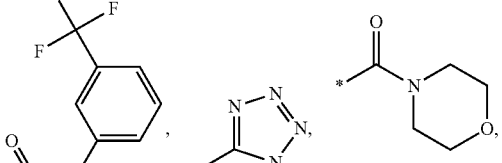

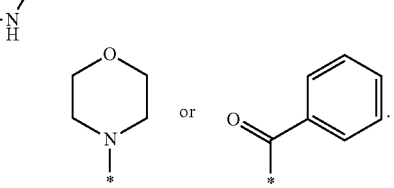

$R_{10}$ is H, Cl, CH₃, OCH₃, NO₂, OH, F, CF₃, OCF₃, Br, CH₃S, AcHN, (CH₃)₂N, CO—NH—NH₂, SO₂NH₂, C(CH₃)₃, COOCH₂CH₃, COCH₃, O(CH₂)₂CH₃, CHO, CO₂H, OCONH₂, CN, C≡CH, N-methylacetamido, 1-[1,2,3]triazolyl, 4-[1,2,3]triazolyl, 5-[1,2,3,4]tetrazolyl, guanidine, C₁₋₆-alkyl, C₁₋₆-alkyl amino substituted with: hydroxyl, C₁₋₆-alkoxy, amino, mono- and di-(C₁₋₆-alkyl) amino, carboxy, C₁₋₆-alkylcarbonylamino, C₁₋₆-alkylaminocarbonyl, aminosulfonyl, mono- and di-(C₁₋₆-alkyl)aminosulfonyl, carbamido, mono- and di-(C₁₋₆-alkyl) aminocarbonylamino, halogen(s), aryl, arylheterocycle, heterocycle, and heteroaryl. C₂₋₆-alkenyl, C₁₋₆-alkoxy, C₂₋₆-alkenyloxy, C₁₋₆-alkoxycarbonyl, C₁₋₆-alkylcarbonyl, C₁₋₆-alkylcarbonyloxy, N,N-dimethylamino, N,N-di(C₁₋₆-alkyl) amino, mono- and di-(C₁₋₆-alkyl)aminocarbonyl, C₁₋₆-alkylcarbonylamino, C₁₋₆-alkylsulfonylamino, C₁₋₆-alkylthio, C₁₋₆-alkylsulphinyl, aryl, aryloxy, arylcarbonyl, arylamino, aryl sulfonylamino, hetrocyclyl, hetrocyclyloxy, heterocyclylamino, heterocyclylcarbonyl, heteroaryl, heteroaryloxy, heteroarylamino, heteroarylcarbonyl, heteroaryl sulfonylamino, O—(CH$_2$)$_{2-4}$-morpholino, O—(CH$_2$)$_{2-4}$-(piperazin-1-yl), O—(CH$_2$)$_{2-4}$-(4-methylpiperazin-1-yl), O—(CH$_2$)$_{2-4}$-mono- and di-(C$_{1-6}$-alkyl)amino, O—(CH$_2$)$_{2-4}$-1H-[1,2,3]triazol-1-yl), O—(CH$_2$)$_{2-4}$-4(1H-[1,2,3]triazol-1-yl), O—(CH$_2$)$_{2-4}$-(4-(C$_{1-6}$-alkyl)-1H-[1,2,3]triazol-1-yl), O—(CH$_2$)$_{2-4}$-4-(1-(C$_{1-6}$-alkyl)-1H-[1,2,3]triazol-1-yl),
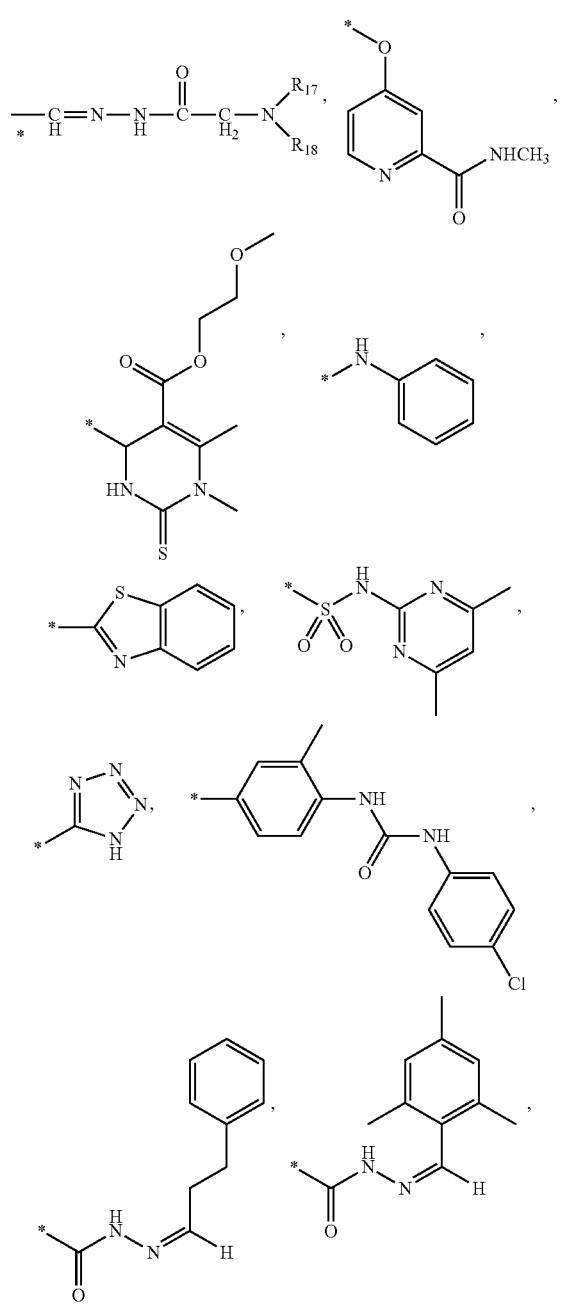
-continued
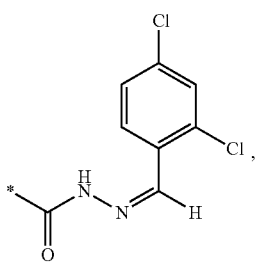
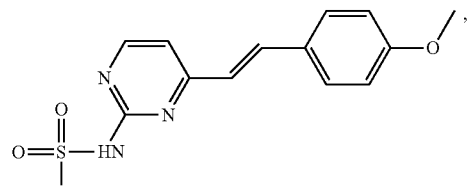
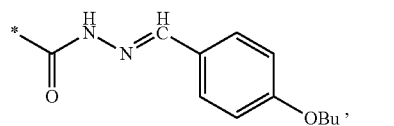
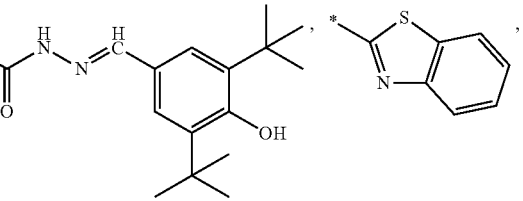
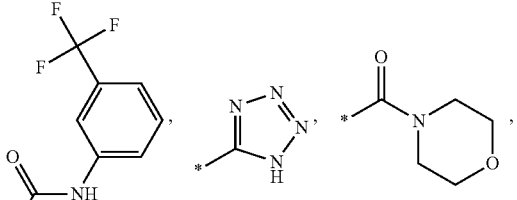
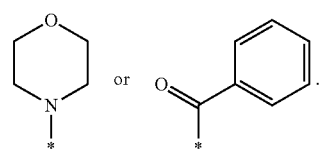
R$_{11}$ is H, CH$_3$
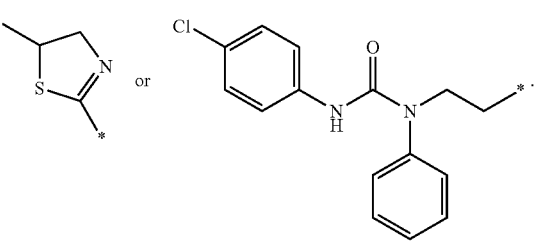

$R_{12}$ is H, $CH_3$,

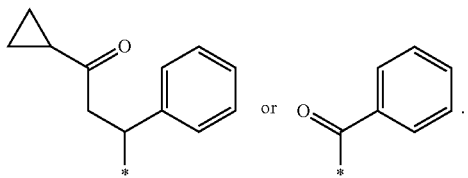 [SMILES: *C(CC(=O)C1CC1)c1ccccc1 ; *C(=O)c1ccccc1]

$R_{13}$ is O, S, NH or $NR_{19}$. For compounds of Formulae II and III, $R_{13}$ is preferably S, NH or $NR_{19}$.

$R_{14}$ is NH, S or

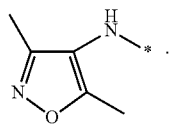 [SMILES: *Nc1c(C)noc1C]

$R_{15}$ is NH, S or NHNCH.

$R_{16}$ is C.

$R_{17}$ is H, $CH_3$, $—[(CH_2)_2—O]_{1-3}H$, $—[(CH_2)_2—O]_{1-3}CH_3$, $—(CH_2)_2—NH_2$, $—(CH_2)—NHCH_3$, $—(CH_2)_2—N(CH_3)_2$, $—[(CH_2)_2—O]_{1-2}(CH_2)_2—NHCH_3$, $—[(CH_2)_2—O]_{1-2}(CH_2)_2—N(CH_3)_2$,

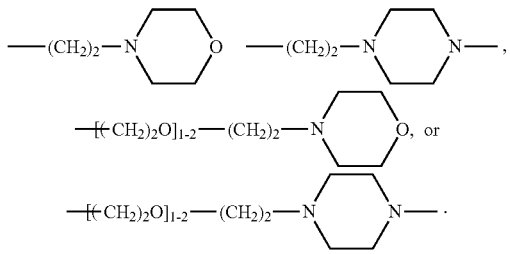

$R_{18}$ is H, $CH_3$, $—[(CH_2)_2—O]_{1-3}H$, $—[(CH_2)_2—O]_{1-3}CH_3$, $—(CH_2)_2—NH_2$, $—(CH_2)—NHCH_3$, $—(CH_2)_2—N(CH_3)_2$, $—[(CH_2)_2—O]_{1-2}(CH_2)_2—NHCH_3$, $—[(CH_2)_2—O]_{1-2}(CH_2)_2—N(CH_3)_2$,

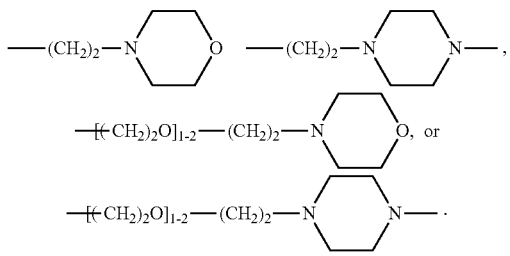

$R_{19}$ is $CH_3$, $C(CH_3)_3$, $C_{1-6}$-alkyl, $C_{1-6}$-alkyl substituted with: hydroxyl, $C_{1-6}$-alkoxy, amino, mono- and di-($C_{1-6}$-alkyl)amino, carboxy, $C_{1-6}$-alkylcarbonylamino, $C_{1-6}$-alkylaminocarbonyl, aminosulfonyl, mono- and di-($C_{1-6}$-alkyl)aminosulfonyl, carbamido, mono- and di-($C_{1-6}$-alkyl)aminocarbonylamino, halogen(s), aryl, arylheterocycle, heterocycle, and heteroaryl. $C_{2-6}$-alkenyl, $—(CH_2)_{2-4}$-morpholino, $—(CH_2)_{2-4}$-(piperazin-1-yl), $—(CH_2)_{2-4}$-(4-methylpiperazin-1-yl), $—(CH_2)_{2-4}$-mono- and di-($C_{1-6}$-alkyl)amino, $—(CH_2)_{2-4}$-1H-[1,2,3]triazol-1-yl, $—(CH_2)_{2-4}$-1H-[1,2,3]triazol-4-yl, $—(CH_2)_{2-4}$-(4-($C_{1-6}$-alkyl)-1H-[1,2,3]triazol-1-yl), or $—(CH_2)_{2-4}$-(1-($C_{1-6}$-alkyl)-1H-[1,2,3]triazol-4-yl).

According to one particular embodiment of Formula I, II or III, $R_{11}$ and $R_{12}$ are absent and a covalent linkage is present between the nitrogenes that is

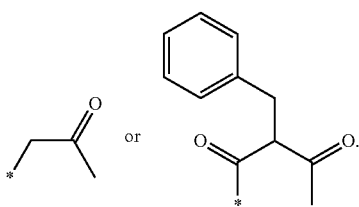

According to another particular embodiment $R_{17}$ and $R_{18}$ are absent and replaced by either

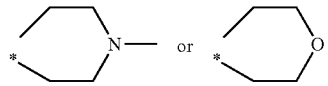

covalently linked to the nitrogen atom.

In certain exemplary embodiments, compounds within the scope of Formula I, II or III are those where, optionally, at least one atom is covalently linked between two R groups. In certain exemplary embodiments, a covalent linkage is present between $R_1$ and $R_{15}$ that is

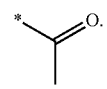

In certain exemplary embodiments, a covalent linkage is present between $R_2$ and $R_3$ that is

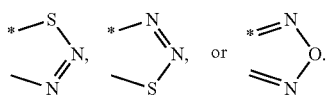

In other embodiments, a covalent linkage is present between $R_7$ and $R_8$ that is

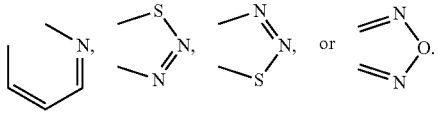

In certain exemplary embodiments, a covalent linkage is present between $R_1$ and $R_2$ that is

In certain exemplary embodiments, a covalent linkage is present between $R_6$ and $R_7$ that is

In other embodiments, a covalent linkage is present between $R_8$ and $R_9$ that is

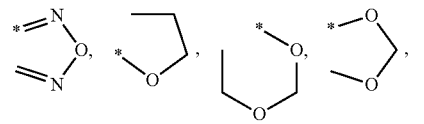

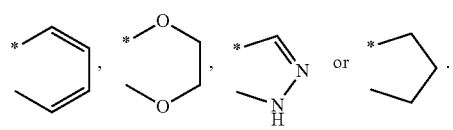

In other embodiments, a covalent linkage is present between $R_9$ and $R_{10}$ that is

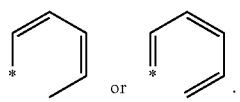

In other embodiments, a covalent linkage is present between $R_{10}$ and $R_{12}$ that is

In other embodiments, a covalent linkage is present between $R_{14}$ and $R_{15}$ that is

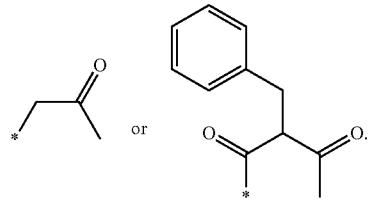

In other embodiments, a covalent linkage is present between $R_{15}$ and $R_{16}$ that is

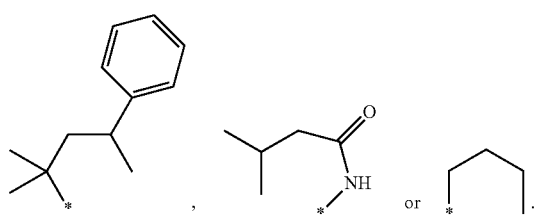

With respect to the substituents identified above, it is to be understood that the substituents are to be covalently linked to an atom or atoms and so one of skill in the art would understand that the terminal lines in the moieties for the various R groups in this application may indicate linkage points to an atom and not the presence of an atom itself.

In accordance with certain embodiments, compounds of the invention are represented by the generic formula set forth below.

Formula IV

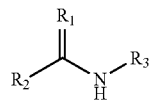

In certain exemplary embodiments with respect to Formula IV above, $R_1$ is S or O.

$R_2$ is $NH_2$, $CH_3$,

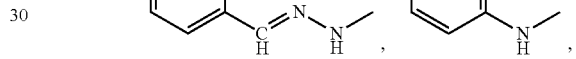

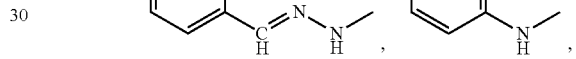

and $R_3$ is OH, $NH_2$, $CH_3$,

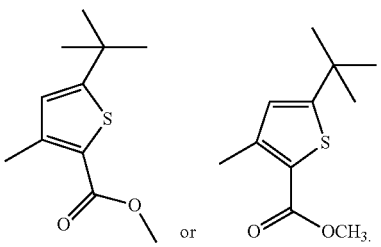

Specific compounds within the scope of the present invention include the following/those set forth in Table 1, below.

TABLE 1

Compounds according to certain exemplary embodiments.

| Compound Number | Structure |
|---|---|
| 1439 | 1,3-bis(4-nitrophenyl)urea |
| 1440 | 1,3-bis(2-methoxyphenyl)urea |
| 1441 | 1-(4-bromophenyl)-3-(4-acetamidophenyl)urea |
| 1442 | 1-(4-chlorophenyl)-3-(4-methoxyphenyl)urea |
| 1443 | 1-(2-chlorophenyl)-3-(3-fluorophenyl)urea |
| 1444 | 1-(4-methylthiophenyl)-3-(4-acetamidophenyl)urea |
| 1445 | 1-(2,4-dimethoxy-5-chlorophenyl)-3-(1H-indazol-5-yl)urea |
| 1446 | 1-(4-acetamidophenyl)-3-(2-trifluoromethylphenyl)urea |
| 1447 | 1-(4-dimethylaminophenyl)-3-(2,4-dimethoxy-5-chlorophenyl)urea |

TABLE 1-continued

Compounds according to certain exemplary embodiments.

| Compound Number | Structure |
| --- | --- |
| 1448 | 4,4'-(carbonylbis(azanediyl))bis(benzimidamide) |
| 1449 | 3-(3-(3-nitrophenyl)ureido)benzenesulfonyl fluoride |
| 1450 | 1,3-di(quinolin-6-yl)urea |
| 1451 | 1-(5-hydroxynaphthalen-1-yl)-3-phenylurea |
| 1452 | 1-(4-fluoro-3-nitrophenyl)-3-(5-hydroxynaphthalen-1-yl)urea |
| 1453 | 1-phenyl-3-(4-(trifluoromethyl)phenyl)urea |
| 1454 | 4-(3-(3-chlorophenyl)ureido)benzohydrazide |
| 1474 | 1-(4-acetamidophenyl)-3-(5-chloro-2,4-dimethoxyphenyl)urea |

TABLE 1-continued

Compounds according to certain exemplary embodiments.

| Compound Number | Structure |
|---|---|
| 1475 | 3-(methylthio)phenyl / 5-chloro-2,4-dimethoxyphenyl urea |
| 1476 | 4-sulfamoylphenyl / 5-chloro-2,4-dimethoxyphenyl urea |
| 1477 | 4-methoxyphenyl / 5-chloro-2,4-dimethoxyphenyl urea |
| 1478 | 4-(N-methyl-N-acetylamino)phenyl / 5-chloro-2,4-dimethoxyphenyl urea |
| 1479 | 3-fluorophenyl / 3-(CF$_2$)phenyl urea |
| 1480 | 3-chlorophenyl / 3-(2-cyanoethyl)phenyl urea |
| 1481 | 3-fluorophenyl / 2-carboxyphenyl urea |
| 1482 | 3-fluorophenyl / 4-(butoxycarbonyl)phenyl urea |

TABLE 1-continued

Compounds according to certain exemplary embodiments.

| Compound Number | Structure |
|---|---|
| 1483 | 3-F-C6H4-NH-C(O)-NH-C6H4-4-NH-Ph |
| 1484 | 3-F-C6H4-NH-C(O)-NH-C6H4-3-NO2 |
| 1485 | 3-Cl-C6H4-NH-C(O)-NH-C6H4-2-CN |
| 1486 | 3-F-C6H4-NH-C(O)-NH-C6H4-4-SO2NH2 |
| 1487 | 3-F-C6H4-NH-C(O)-NH-C6H4-4-Ac |
| 1496 | 2-[(4-methylphenyl)azo]-5-methylphenyl-NH-C(O)-NH-(5-chloro-2-methylphenyl) |
| 1497 | 2-(4-chloro-2-sulfophenoxy)-5-chlorophenyl-NH-C(O)-NH-(4-chloro-3-trifluoromethylphenyl) |

TABLE 1-continued
Compounds according to certain exemplary embodiments.
| Compound Number | Structure |
|---|---|
| 1498 | 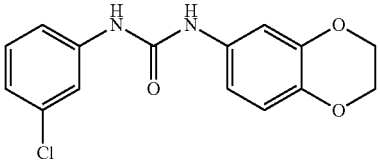 [SMILES: O=C(Nc1cccc(Cl)c1)Nc1ccc2c(c1)OCCO2] |
| 1499 | 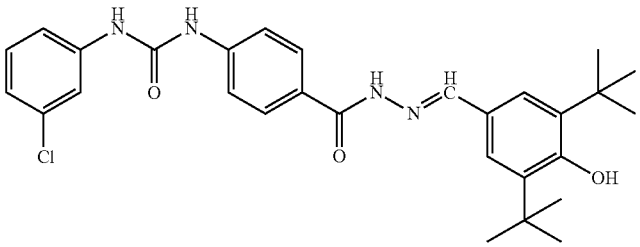 [SMILES: CC(C)(C)c1cc(/C=N/NC(=O)c2ccc(NC(=O)Nc3cccc(Cl)c3)cc2)cc(C(C)(C)C)c1O] |
| 1500 | 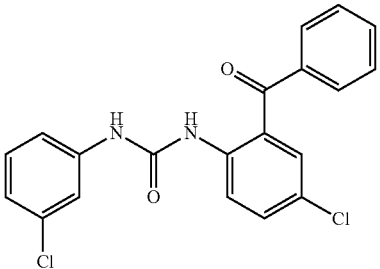 [SMILES: O=C(Nc1cccc(Cl)c1)Nc1ccc(Cl)cc1C(=O)c1ccccc1] |
| 1501 | 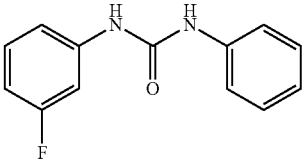 [SMILES: O=C(Nc1ccccc1)Nc1cccc(F)c1] |
| 1502 | 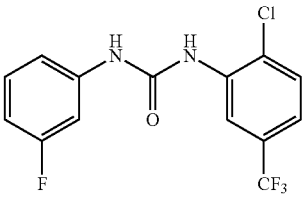 [SMILES: O=C(Nc1cccc(F)c1)Nc1cc(C(F)(F)F)ccc1Cl] |
| 1503 | 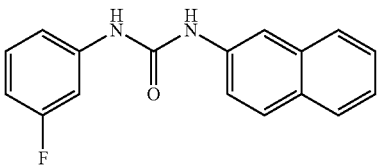 [SMILES: O=C(Nc1cccc(F)c1)Nc1ccc2ccccc2c1] |

TABLE 1-continued

Compounds according to certain exemplary embodiments.

| Compound Number | Structure |
|---|---|
| 1504 | 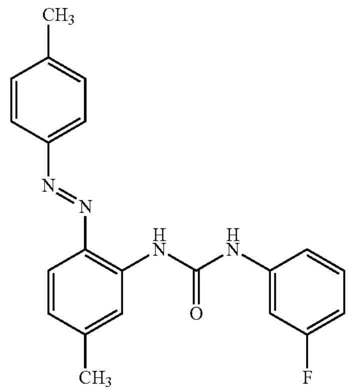 [SMILES: Cc1ccc(/N=N/c2ccc(C)cc2NC(=O)Nc2cccc(F)c2)cc1] |
| 1505 | 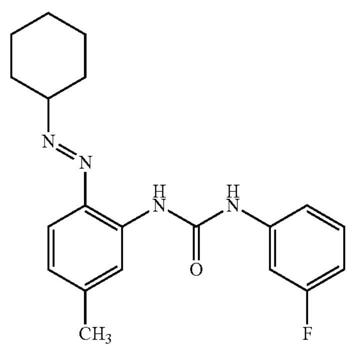 [SMILES: Cc1ccc(/N=N/C2CCCCC2)c(NC(=O)Nc2cccc(F)c2)c1] |
| 1506 | 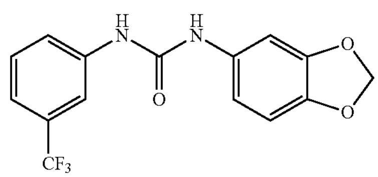 [SMILES: O=C(Nc1cccc(C(F)(F)F)c1)Nc1ccc2c(c1)OCO2] |
| 1507 | 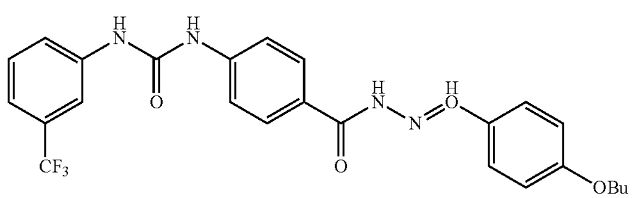 |
| 1508 | 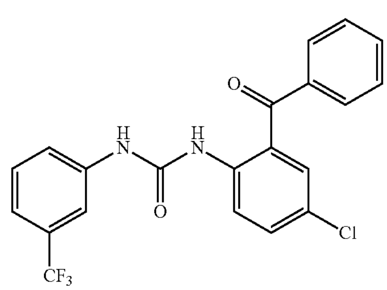 [SMILES: O=C(Nc1cccc(C(F)(F)F)c1)Nc1ccc(Cl)cc1C(=O)c1ccccc1] |

TABLE 1-continued
Compounds according to certain exemplary embodiments.
| Compound Number | Structure |
|---|---|
| 1509 | 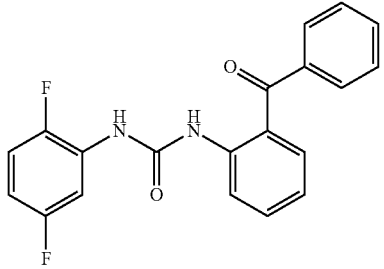 [SMILES: O=C(Nc1cc(F)ccc1F)Nc1ccccc1C(=O)c1ccccc1] |
| 1510 | 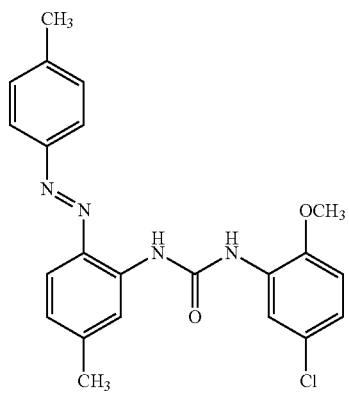 [SMILES: COc1ccc(Cl)cc1NC(=O)Nc1cc(C)ccc1/N=N/c1ccc(C)cc1] |
| 1511 | 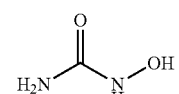 |
| 1518 | 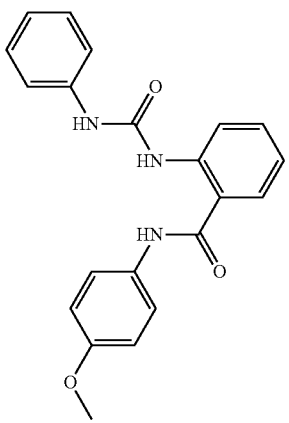 [SMILES: COc1ccc(NC(=O)c2ccccc2NC(=O)Nc2ccccc2)cc1] |

TABLE 1-continued

Compounds according to certain exemplary embodiments.

| Compound Number | Structure |
|---|---|
| 1519 | 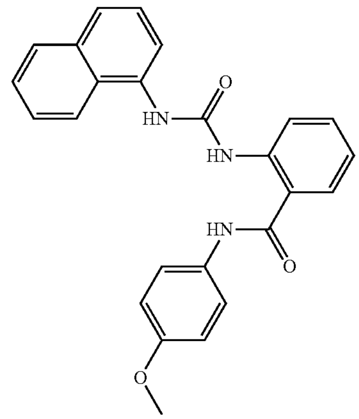 [SMILES: COc1ccc(NC(=O)c2ccccc2NC(=O)Nc2cccc3ccccc23)cc1] |
| 1520 | 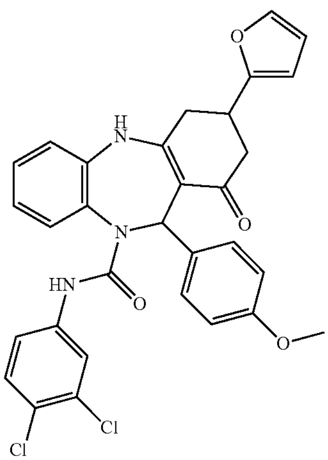 [SMILES: COc1ccc(C2C3=C(CC(c4ccco4)CC3=O)Nc3ccccc3N2C(=O)Nc2ccc(Cl)c(Cl)c2)cc1] |
| 1521 | 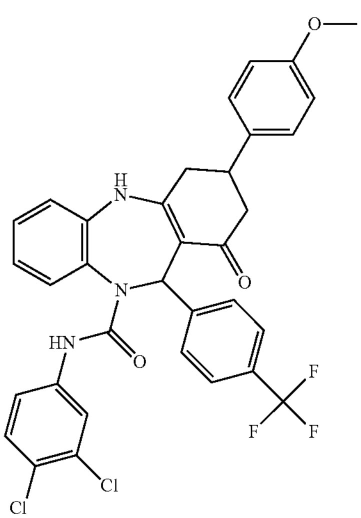 [SMILES: COc1ccc(C2CC(=O)C3=C(C2)Nc2ccccc2N(C(=O)Nc2ccc(Cl)c(Cl)c2)C3c2ccc(C(F)(F)F)cc2)cc1] |
| 1522 | 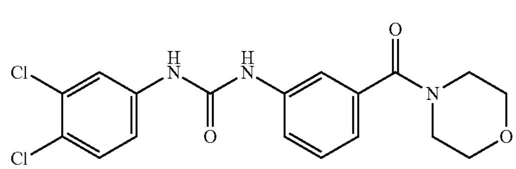 [SMILES: O=C(Nc1cccc(C(=O)N2CCOCC2)c1)Nc1ccc(Cl)c(Cl)c1] |

TABLE 1-continued

Compounds according to certain exemplary embodiments.

| Compound Number | Structure |
|---|---|
| 1523 | 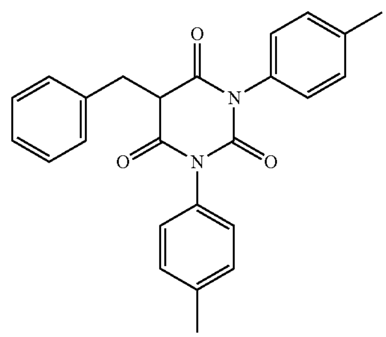 [SMILES: Cc1ccc(N2C(=O)C(Cc3ccccc3)C(=O)N(c3ccc(C)cc3)C2=O)cc1] |
| 1524 | 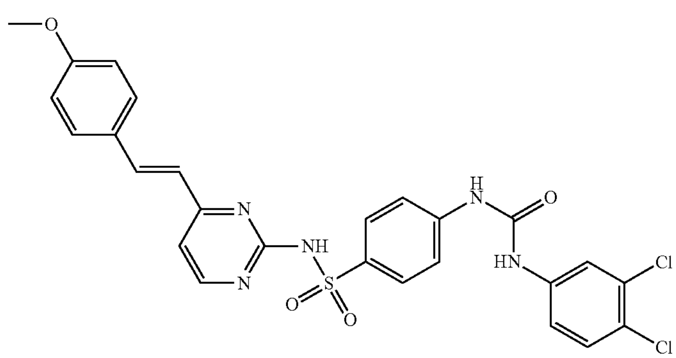 [SMILES: COc1ccc(/C=C/c2ccnc(NS(=O)(=O)c3ccc(NC(=O)Nc4ccc(Cl)c(Cl)c4)cc3)n2)cc1] |
| 1525 | 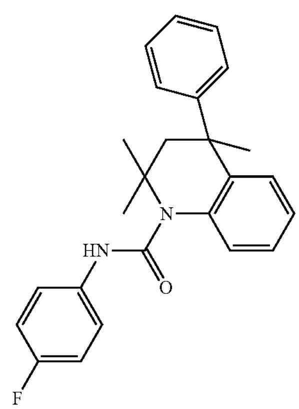 [SMILES: CC1(c2ccccc2)CC(C)(C)N(C(=O)Nc2ccc(F)cc2)c2ccccc21] |
| 1526 | 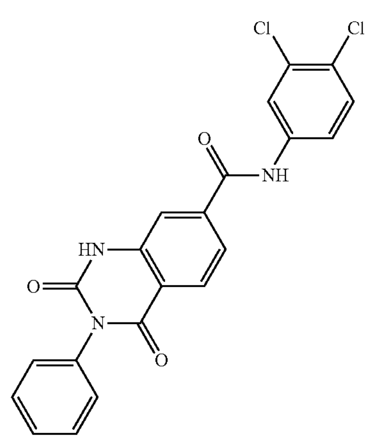 [SMILES: O=C(Nc1ccc(Cl)c(Cl)c1)c1ccc2c(=O)n(-c3ccccc3)c(=O)[nH]c2c1] |

TABLE 1-continued

Compounds according to certain exemplary embodiments.

| Compound Number | Structure |
|---|---|
| 1527 | 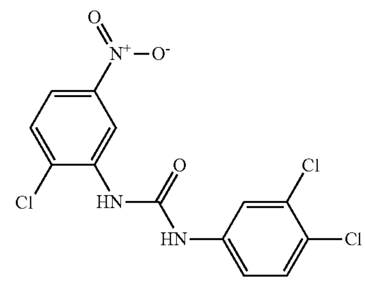 [SMILES: O=C(Nc1ccc(Cl)c(Cl)c1)Nc1cc([N+](=O)[O-])ccc1Cl] |
| 1528 | 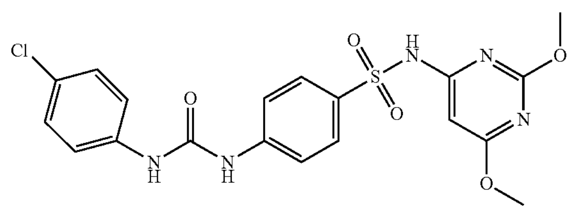 [SMILES: COc1cc(NS(=O)(=O)c2ccc(NC(=O)Nc3ccc(Cl)cc3)cc2)nc(OC)n1] |
| 1529 | 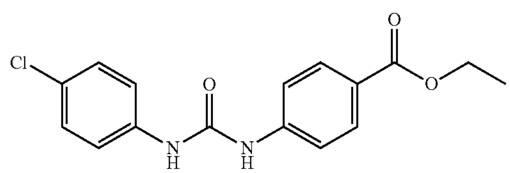 [SMILES: CCOC(=O)c1ccc(NC(=O)Nc2ccc(Cl)cc2)cc1] |
| 1530 | 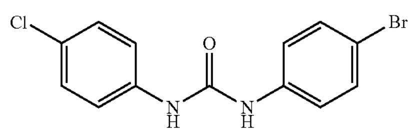 [SMILES: O=C(Nc1ccc(Cl)cc1)Nc1ccc(Br)cc1] |
| 1531 | 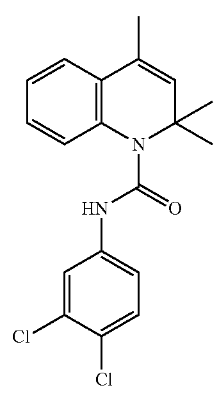 [SMILES: CC1=CC(C)(C)N(C(=O)Nc2ccc(Cl)c(Cl)c2)c2ccccc21] |
| 1532 | 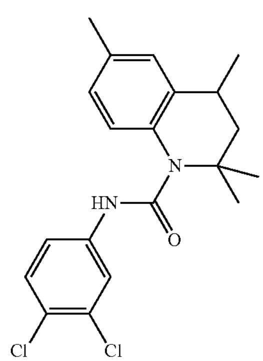 [SMILES: Cc1ccc2c(c1)C(C)CC(C)(C)N2C(=O)Nc1ccc(Cl)c(Cl)c1] |

TABLE 1-continued

Compounds according to certain exemplary embodiments.

| Compound Number | Structure |
| --- | --- |
| 1533 | 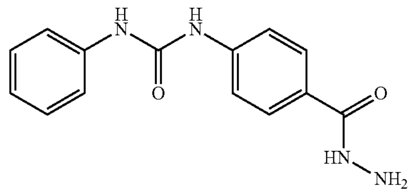 [SMILES: NNC(=O)c1ccc(NC(=O)Nc2ccccc2)cc1] |
| 1534 | 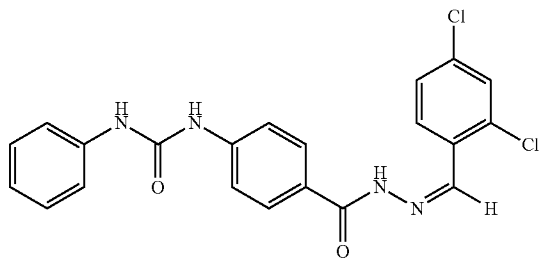 [SMILES: O=C(Nc1ccccc1)Nc1ccc(C(=O)N/N=C\c2ccc(Cl)cc2Cl)cc1] |
| 1535 | 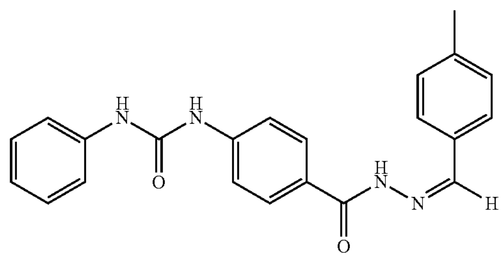 [SMILES: Cc1ccc(/C=N\NC(=O)c2ccc(NC(=O)Nc3ccccc3)cc2)cc1] |
| 1536 | 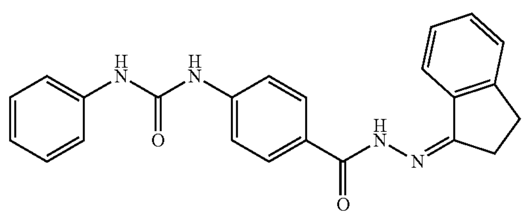 [SMILES: O=C(Nc1ccccc1)Nc1ccc(C(=O)N/N=C2/CCc3ccccc32)cc1] |
| 1537 | 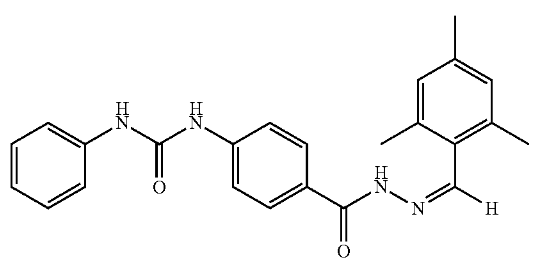 [SMILES: Cc1cc(C)c(/C=N\NC(=O)c2ccc(NC(=O)Nc3ccccc3)cc2)c(C)c1] |
| 1538 | 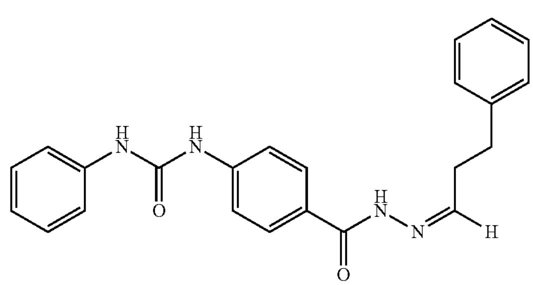 [SMILES: O=C(Nc1ccccc1)Nc1ccc(C(=O)N/N=C\CCc2ccccc2)cc1] |

TABLE 1-continued

Compounds according to certain exemplary embodiments.

| Compound Number | Structure |
|---|---|
| 1539 | 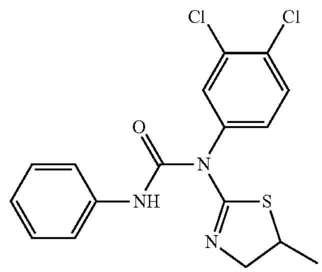 [SMILES: CC1CN=C(N(C(=O)Nc2ccccc2)c2ccc(Cl)c(Cl)c2)S1] |
| 1540 | 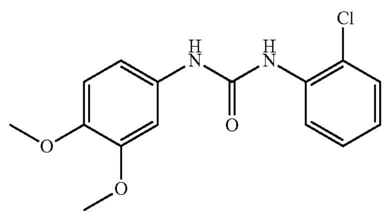 [SMILES: COc1ccc(NC(=O)Nc2ccccc2Cl)cc1OC] |
| 1541 | 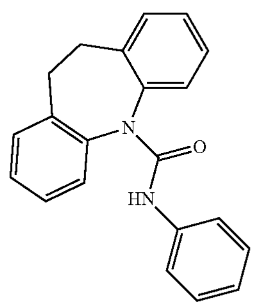 [SMILES: O=C(Nc1ccccc1)N1c2ccccc2CCc2ccccc21] |
| 1542 | 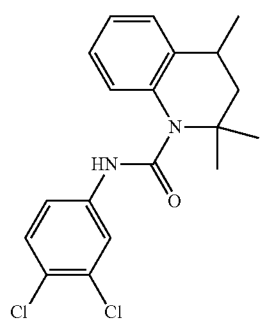 [SMILES: CC1CC(C)(C)N(C(=O)Nc2ccc(Cl)c(Cl)c2)c2ccccc21] |
| 1543 | 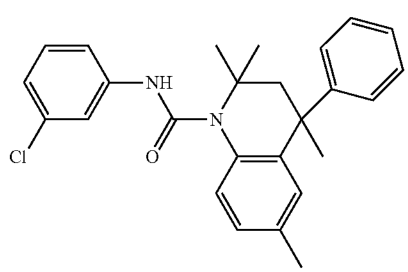 [SMILES: Cc1ccc2c(c1)C(C)(c1ccccc1)CC(C)(C)N2C(=O)Nc1cccc(Cl)c1] |

TABLE 1-continued

Compounds according to certain exemplary embodiments.

| Compound Number | Structure |
|---|---|
| 1544 | 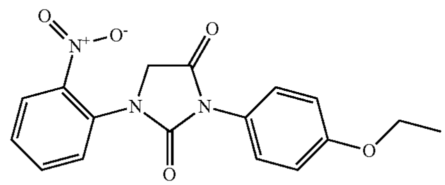 [SMILES: CCOc1ccc(N2C(=O)CN(c3ccccc3[N+](=O)[O-])C2=O)cc1] |
| 1545 | 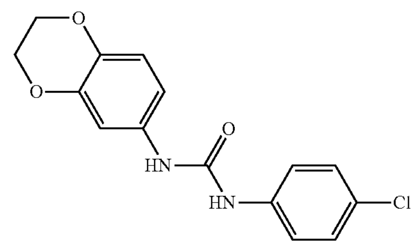 [SMILES: O=C(Nc1ccc(Cl)cc1)Nc1ccc2c(c1)OCCO2] |
| 1546 | 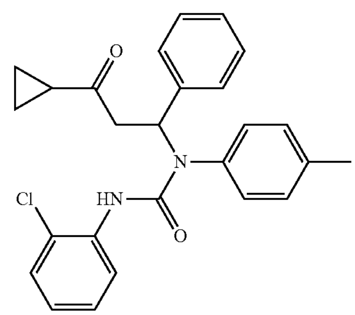 [SMILES: Cc1ccc(N(C(=O)Nc2ccccc2Cl)C(CC(=O)C2CC2)c2ccccc2)cc1] |
| 1547 | 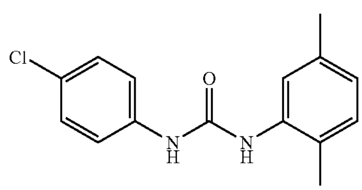 [SMILES: Cc1ccc(C)c(NC(=O)Nc2ccc(Cl)cc2)c1] |
| 1548 | 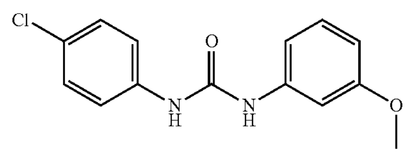 [SMILES: COc1cccc(NC(=O)Nc2ccc(Cl)cc2)c1] |
| 1549 | 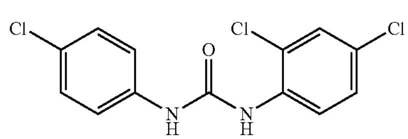 [SMILES: O=C(Nc1ccc(Cl)cc1)Nc1ccc(Cl)cc1Cl] |
| 1550 | 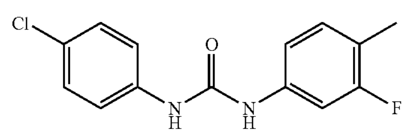 [SMILES: Cc1ccc(NC(=O)Nc2ccc(Cl)cc2)cc1F] |

TABLE 1-continued

Compounds according to certain exemplary embodiments.

| Compound Number | Structure |
|---|---|
| 1551 | 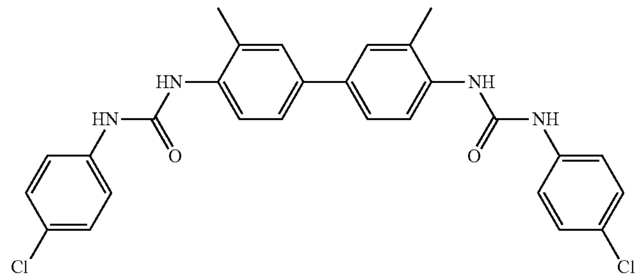 [SMILES: Cc1cc(-c2ccc(NC(=O)Nc3ccc(Cl)cc3)c(C)c2)ccc1NC(=O)Nc1ccc(Cl)cc1] |
| 1552 | 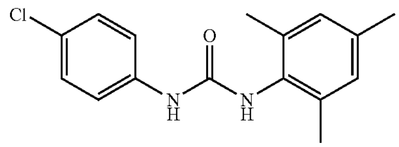 [SMILES: Cc1cc(C)c(NC(=O)Nc2ccc(Cl)cc2)c(C)c1] |
| 1553 | 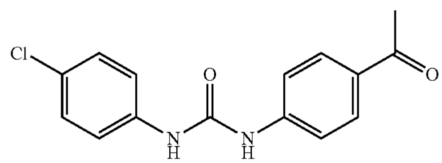 [SMILES: CC(=O)c1ccc(NC(=O)Nc2ccc(Cl)cc2)cc1] |
| 1554 | 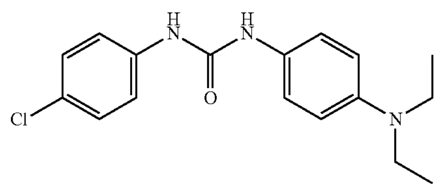 [SMILES: CCN(CC)c1ccc(NC(=O)Nc2ccc(Cl)cc2)cc1] |
| 1555 | 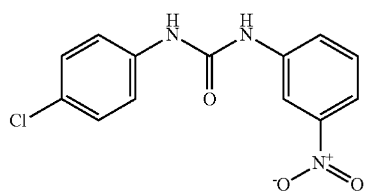 |
| 1556 | 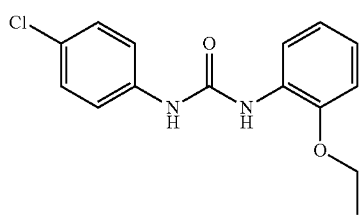 [SMILES: CCOc1ccccc1NC(=O)Nc1ccc(Cl)cc1] |
| 1557 | 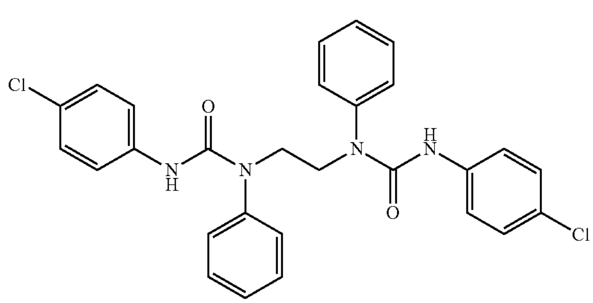 [SMILES: O=C(Nc1ccc(Cl)cc1)N(CCN(C(=O)Nc1ccc(Cl)cc1)c1ccccc1)c1ccccc1] |

TABLE 1-continued

Compounds according to certain exemplary embodiments.

| Compound Number | Structure |
|---|---|
| 1558 | 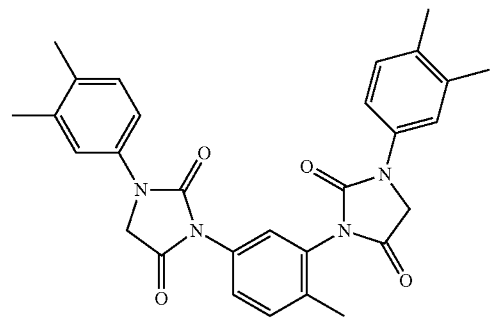 |
| 1559 | 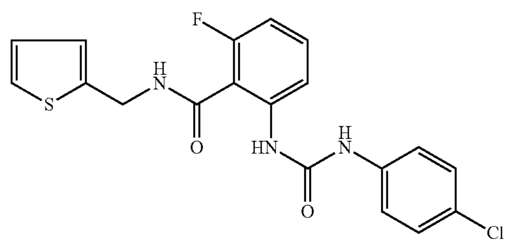 [SMILES: O=C(Nc1ccc(Cl)cc1)Nc1cccc(F)c1C(=O)NCc1cccs1] |
| 1560 | 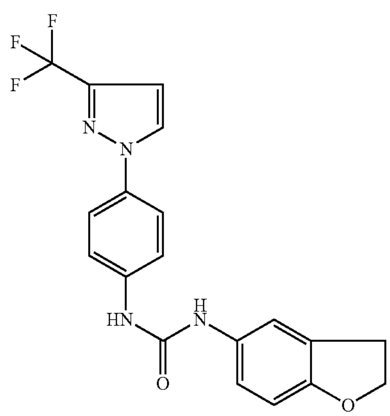 [SMILES: O=C(Nc1ccc(-n2ccc(C(F)(F)F)n2)cc1)Nc1ccc2c(c1)CCO2] |
| 1561 | 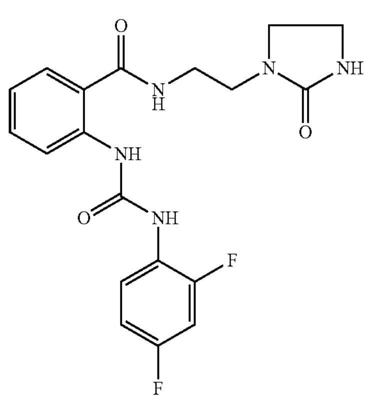 [SMILES: O=C(Nc1ccc(F)cc1F)Nc1ccccc1C(=O)NCCN1CCNC1=O] |

TABLE 1-continued

Compounds according to certain exemplary embodiments.

| Compound Number | Structure |
|---|---|
| 1562 | 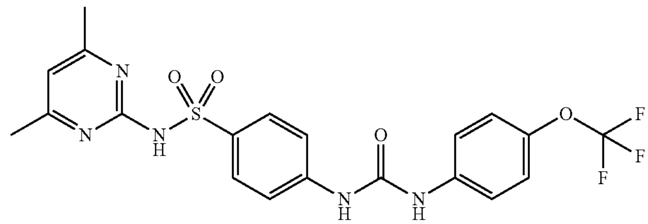 [SMILES: Cc1cc(C)nc(NS(=O)(=O)c2ccc(NC(=O)Nc3ccc(OC(F)(F)F)cc3)cc2)n1] |
| 1563 | 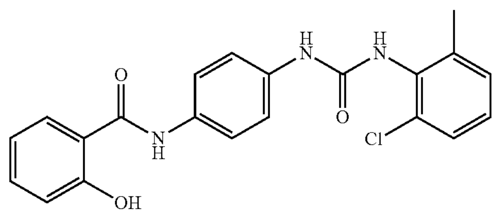 [SMILES: Cc1cccc(Cl)c1NC(=O)Nc1ccc(NC(=O)c2ccccc2O)cc1] |
| 1564 | 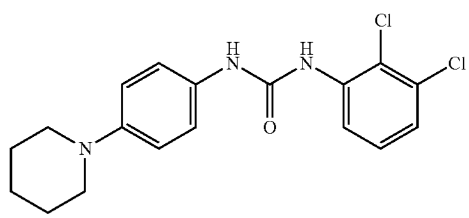 [SMILES: O=C(Nc1ccc(N2CCCCC2)cc1)Nc1cccc(Cl)c1Cl] |
| 1565 | 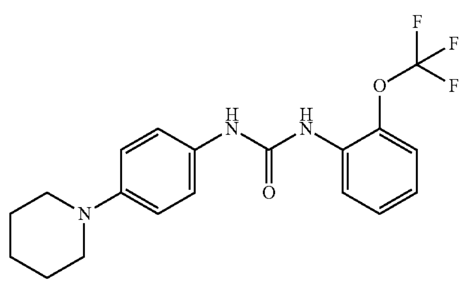 [SMILES: O=C(Nc1ccc(N2CCCCC2)cc1)Nc1ccccc1OC(F)(F)F] |
| 1566 | 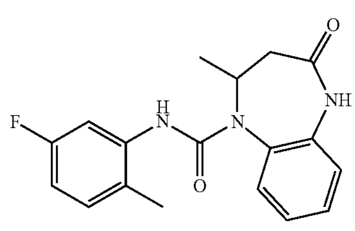 [SMILES: Cc1ccc(F)cc1NC(=O)N1c2ccccc2NC(=O)CC1C] |
| 1567 | 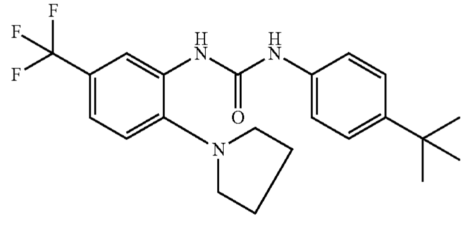 [SMILES: CC(C)(C)c1ccc(NC(=O)Nc2cc(C(F)(F)F)ccc2N2CCCC2)cc1] |

TABLE 1-continued

Compounds according to certain exemplary embodiments.

| Compound Number | Structure |
|---|---|
| 1568 | 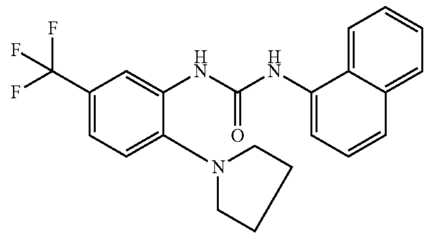 [SMILES: O=C(Nc1cc(C(F)(F)F)ccc1N1CCCC1)Nc1cccc2ccccc12] |
| 1569 | 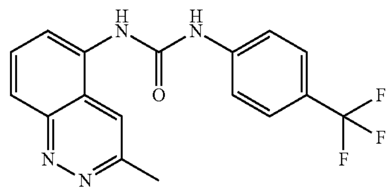 [SMILES: Cc1cc2c(NC(=O)Nc3ccc(C(F)(F)F)cc3)cccc2nn1] |
| 1570 | 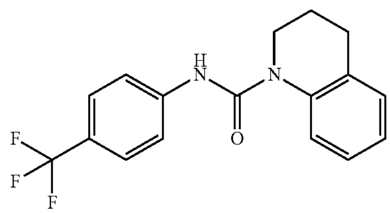 [SMILES: O=C(Nc1ccc(C(F)(F)F)cc1)N1CCCc2ccccc21] |
| 1571 | 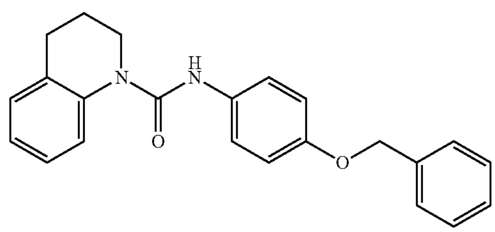 [SMILES: O=C(Nc1ccc(OCc2ccccc2)cc1)N1CCCc2ccccc21] |
| 1572 | 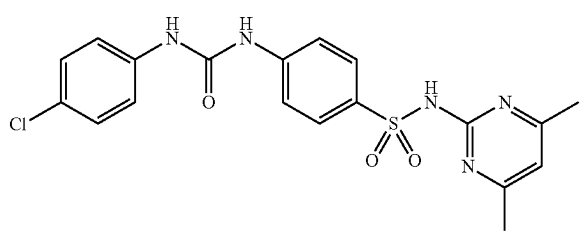 [SMILES: Cc1cc(C)nc(NS(=O)(=O)c2ccc(NC(=O)Nc3ccc(Cl)cc3)cc2)n1] |
| 1573 | 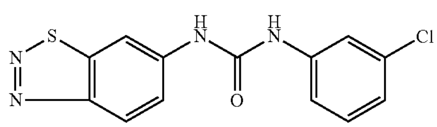 [SMILES: O=C(Nc1cccc(Cl)c1)Nc1ccc2nnsc2c1] |
| 1574 | 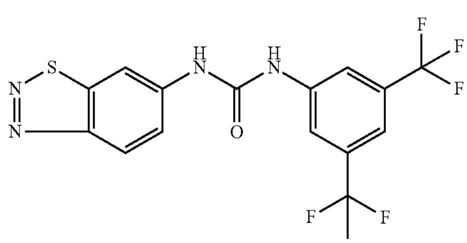 [SMILES: CC(F)(F)c1cc(NC(=O)Nc2ccc3nnsc3c2)cc(C(F)(F)F)c1] |

TABLE 1-continued
Compounds according to certain exemplary embodiments.
| Compound Number | Structure |
|---|---|
| 1575 | 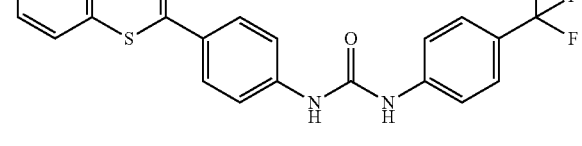 |
| 1576 | 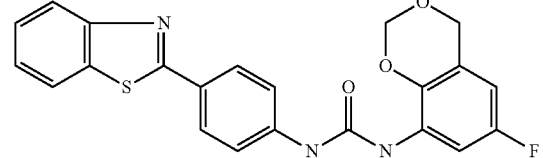 |
| 1577 | 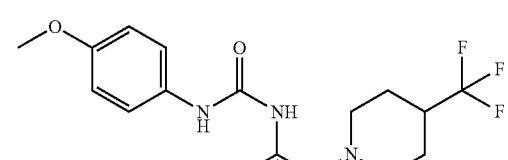 |
| 1578 | 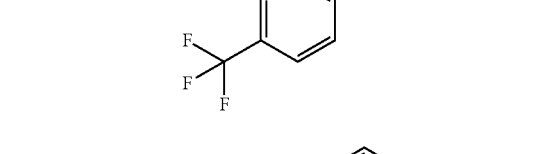 |
| 1584 | 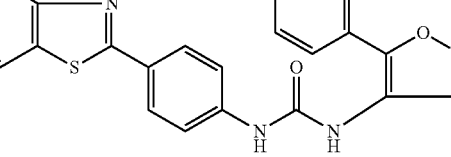 |
| 1585 | 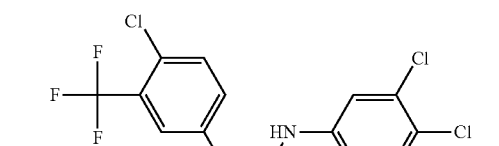 |
| 1586 | 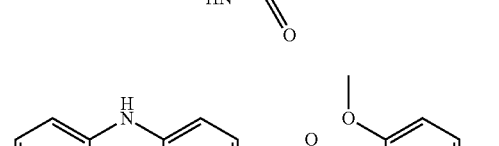 |

TABLE 1-continued

Compounds according to certain exemplary embodiments.

| Compound Number | Structure |
|---|---|
| 1587 | 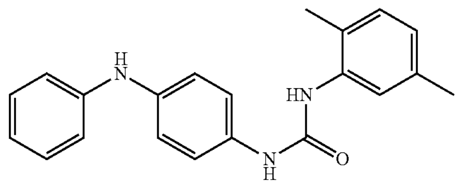 [SMILES: Cc1ccc(C)c(NC(=O)Nc2ccc(Nc3ccccc3)cc2)c1] |
| 1612 | 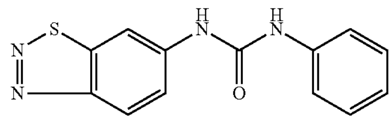 [SMILES: O=C(Nc1ccccc1)Nc1ccc2nnsc2c1] |
| 1613 | 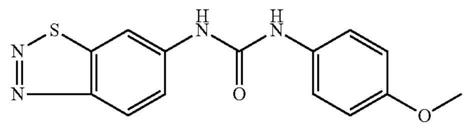 [SMILES: COc1ccc(NC(=O)Nc2ccc3nnsc3c2)cc1] |
| BAS 93909 | 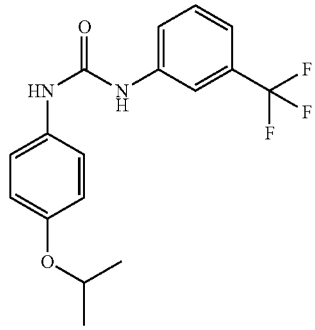 [SMILES: CC(C)Oc1ccc(NC(=O)Nc2cccc(C(F)(F)F)c2)cc1] |
| BAS 93826 | 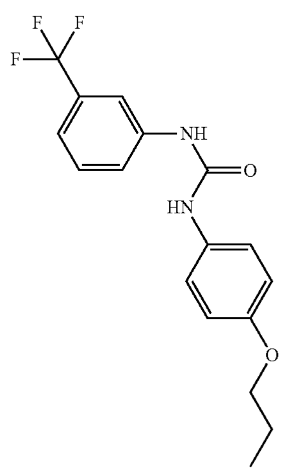 [SMILES: CCCOc1ccc(NC(=O)Nc2cccc(C(F)(F)F)c2)cc1] |
| BAS 167472 | 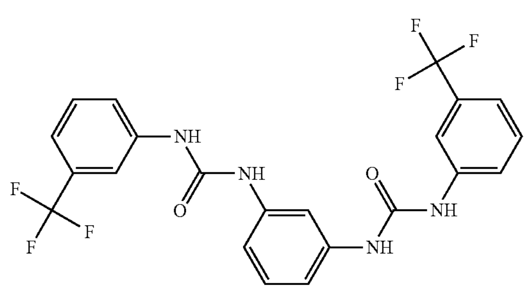 [SMILES: O=C(Nc1cccc(NC(=O)Nc2cccc(C(F)(F)F)c2)c1)Nc1cccc(C(F)(F)F)c1] |

TABLE 1-continued

Compounds according to certain exemplary embodiments.

| Compound Number | Structure |
|---|---|
| BAS 728878 | 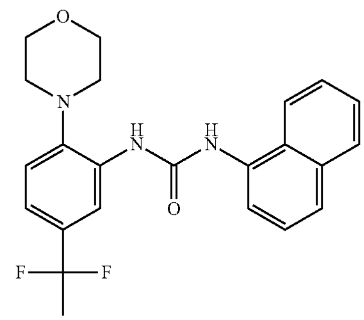 [SMILES: CC(F)(F)c1ccc(N2CCOCC2)c(NC(=O)Nc2cccc3ccccc23)c1] |
| BTB 06969 | 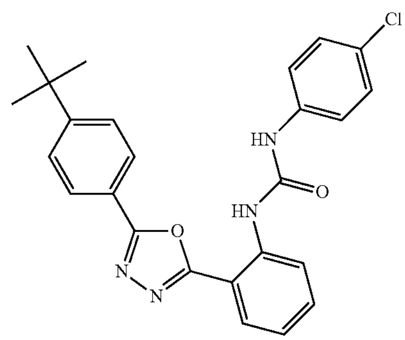 [SMILES: CC(C)(C)c1ccc(-c2nnc(-c3ccccc3NC(=O)Nc3ccc(Cl)cc3)o2)cc1] |
| CD 06116 | 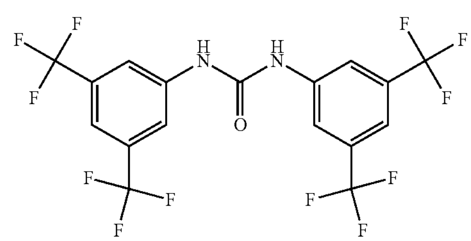 [SMILES: O=C(Nc1cc(C(F)(F)F)cc(C(F)(F)F)c1)Nc1cc(C(F)(F)F)cc(C(F)(F)F)c1] |
| HTS 02561 | 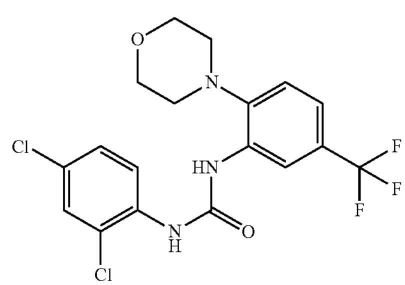 [SMILES: O=C(Nc1ccc(Cl)cc1Cl)Nc1cc(C(F)(F)F)ccc1N1CCOCC1] |
| HTS 02562 | 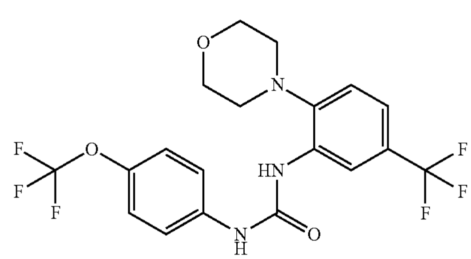 [SMILES: O=C(Nc1ccc(OC(F)(F)F)cc1)Nc1cc(C(F)(F)F)ccc1N1CCOCC1] |

TABLE 1-continued

Compounds according to certain exemplary embodiments.

| Compound Number | Structure |
|---|---|
| HTS 04043 | 1-(4-(5-(thiophen-2-yl)-3-(trifluoromethyl)-1H-pyrazol-1-yl)phenyl)-3-(3,5-dimethylphenyl)urea |
| HTS 06049 | 1-(4-(3-(trifluoromethyl)-1H-pyrazol-1-yl)phenyl)-3-(3,5-dimethylphenyl)urea |
| KM 08479 | 1-(3-oxo-1,3-dihydroisobenzofuran-5-yl)-3-(3,5-dichlorophenyl)urea |
| KM 09745 | 1-phenyl-3-(benzo[c][1,2,5]oxadiazol-5-yl)urea |
| KM 09748 | 1-(4-chlorophenyl)-3-(benzo[c][1,2,5]oxadiazol-5-yl)urea |
| KM 09749 | 1-(4-methoxyphenyl)-3-(benzo[c][1,2,5]oxadiazol-5-yl)urea |

TABLE 1-continued
Compounds according to certain exemplary embodiments.
| Compound Number | Structure |
|---|---|
| KM 09750 | 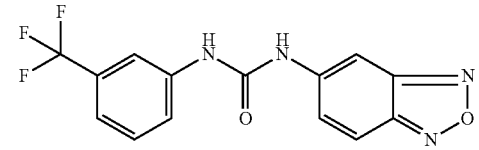 [SMILES: O=C(Nc1cccc(C(F)(F)F)c1)Nc1ccc2nonc2c1] |
| RF 00386 | 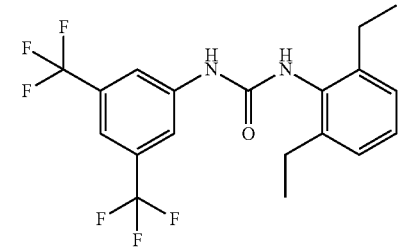 [SMILES: CCc1cccc(CC)c1NC(=O)Nc1cc(C(F)(F)F)cc(C(F)(F)F)c1] |
| RF 00680 | 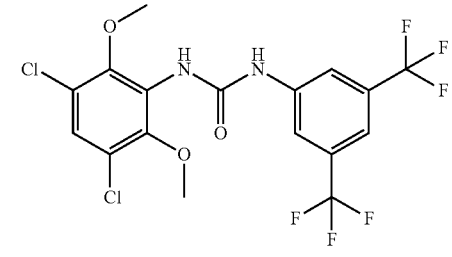 [SMILES: COc1c(Cl)cc(Cl)c(OC)c1NC(=O)Nc1cc(C(F)(F)F)cc(C(F)(F)F)c1] |
| S 09172 | 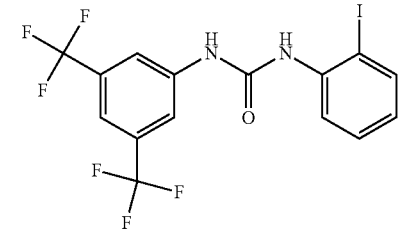 [SMILES: O=C(Nc1cc(C(F)(F)F)cc(C(F)(F)F)c1)Nc1ccccc1I] |
| SPB 06399 | 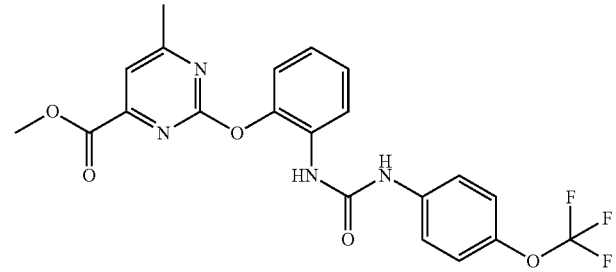 [SMILES: COC(=O)c1cc(C)nc(Oc2ccccc2NC(=O)Nc2ccc(OC(F)(F)F)cc2)n1] |

TABLE 1-continued
Compounds according to certain exemplary embodiments.
| Compound Number | Structure |
|---|---|
| BAS 4320322 | 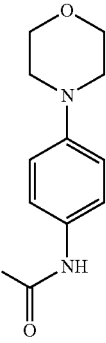 |
| CGX-0138398 | 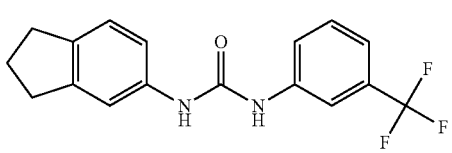 [SMILES: O=C(Nc1cccc(C(F)(F)F)c1)Nc1ccc2c(c1)CCC2] |
| CGX-0778260 | 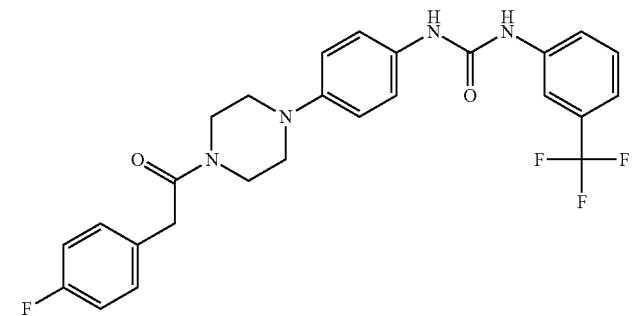 [SMILES: O=C(Nc1ccc(N2CCN(C(=O)Cc3ccc(F)cc3)CC2)cc1)Nc1cccc(C(F)(F)F)c1] |
| CGX-0778468 | 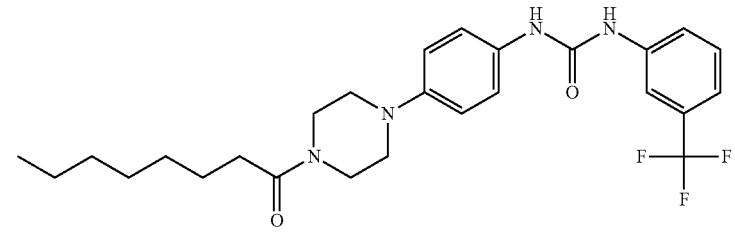 [SMILES: CCCCCCCC(=O)N1CCN(c2ccc(NC(=O)Nc3cccc(C(F)(F)F)c3)cc2)CC1] |
| CGX-0778832 | 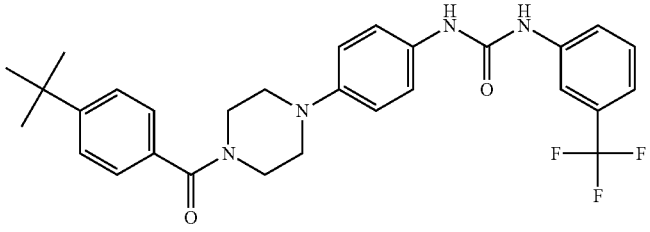 [SMILES: CC(C)(C)c1ccc(C(=O)N2CCN(c3ccc(NC(=O)Nc4cccc(C(F)(F)F)c4)cc3)CC2)cc1] |
| CGX-0778728 | 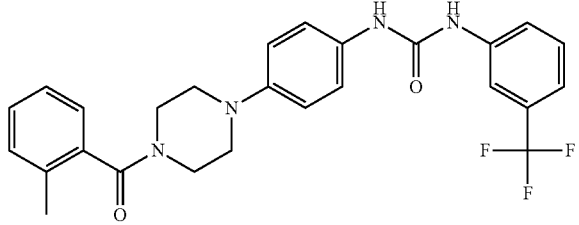 [SMILES: Cc1ccccc1C(=O)N1CCN(c2ccc(NC(=O)Nc3cccc(C(F)(F)F)c3)cc2)CC1] |

TABLE 1-continued
Compounds according to certain exemplary embodiments.
| Compound Number | Structure |
|---|---|
| CGX-0778220 | 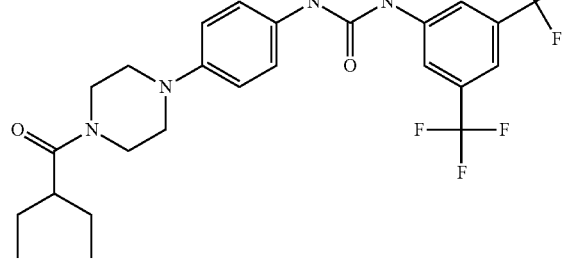 |
| CGX-0778272 | 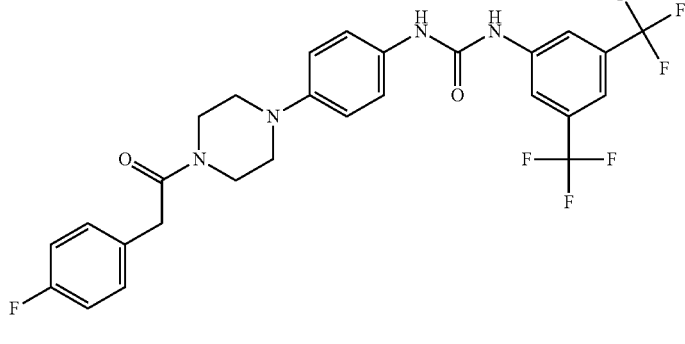 |
| CGX-0778480 | 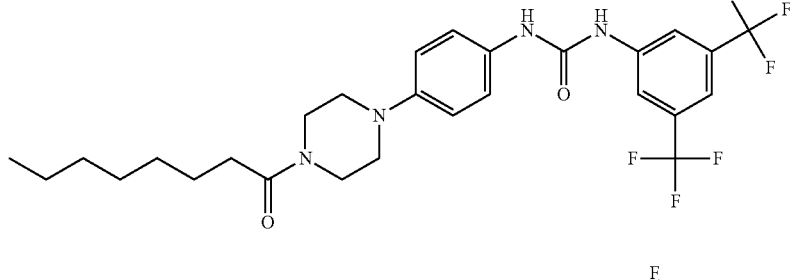 |
| CGX-0778688 | 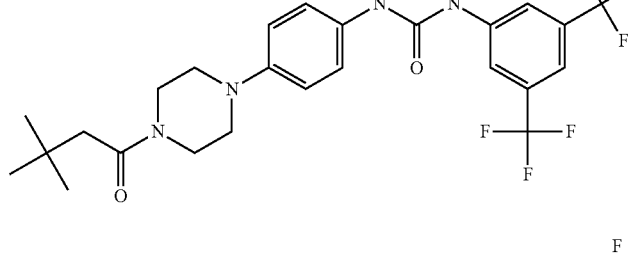 |
| CGX-0778636 | 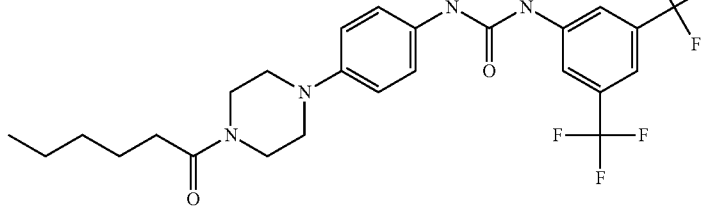 |

TABLE 1-continued

Compounds according to certain exemplary embodiments.

| Compound Number | Structure |
|---|---|
| CGX-0778844 | 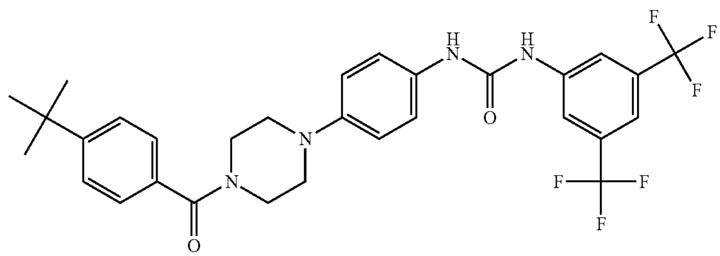 [SMILES: CC(C)(C)c1ccc(C(=O)N2CCN(c3ccc(NC(=O)Nc4cc(C(F)(F)F)cc(C(F)(F)F)c4)cc3)CC2)cc1] |
| CGX-0779582 | 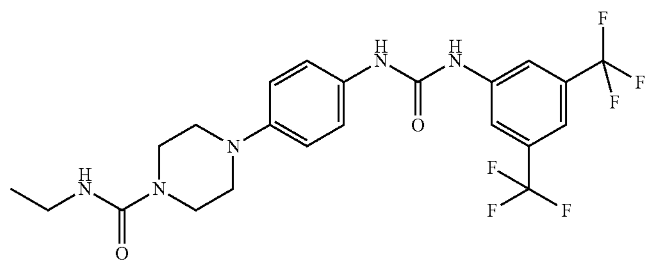 [SMILES: CCNC(=O)N1CCN(c2ccc(NC(=O)Nc3cc(C(F)(F)F)cc(C(F)(F)F)c3)cc2)CC1] |
| CGX-0790347 | 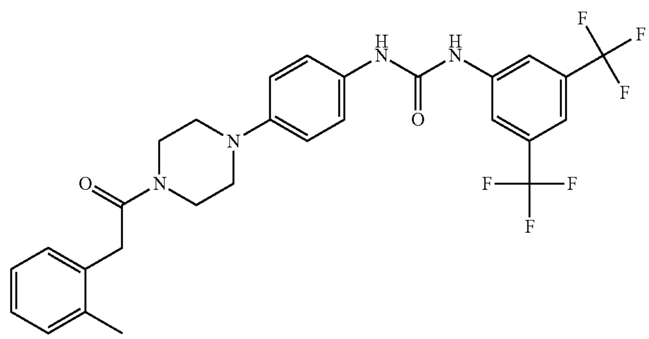 [SMILES: Cc1ccccc1CC(=O)N1CCN(c2ccc(NC(=O)Nc3cc(C(F)(F)F)cc(C(F)(F)F)c3)cc2)CC1] |
| CGX-0790503 | 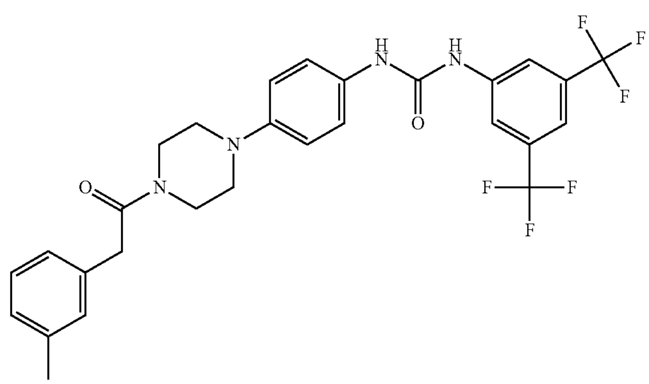 [SMILES: Cc1cccc(CC(=O)N2CCN(c3ccc(NC(=O)Nc4cc(C(F)(F)F)cc(C(F)(F)F)c4)cc3)CC2)c1] |
| CGX-0778896 | 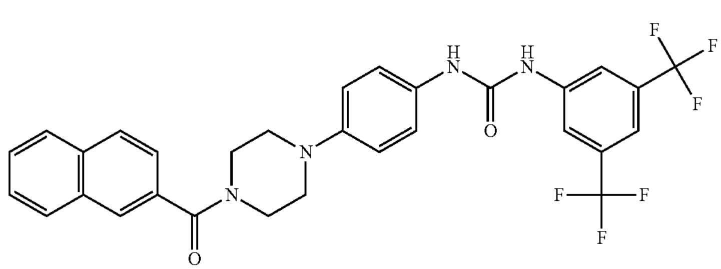 [SMILES: O=C(Nc1ccc(N2CCN(C(=O)c3ccc4ccccc4c3)CC2)cc1)Nc1cc(C(F)(F)F)cc(C(F)(F)F)c1] |

TABLE 1-continued
Compounds according to certain exemplary embodiments.
| Compound Number | Structure |
|---|---|
| CGX-2086541 | 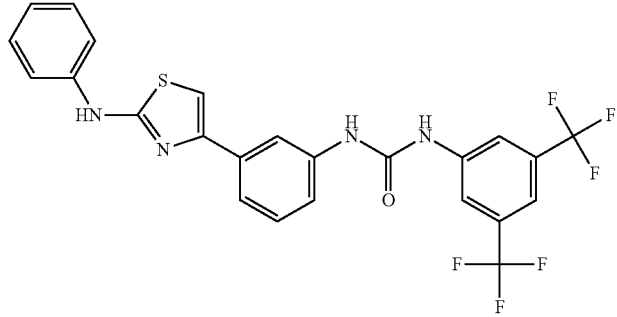 [SMILES: O=C(Nc1cccc(-c2csc(Nc3ccccc3)n2)c1)Nc1cc(C(F)(F)F)cc(C(F)(F)F)c1] |
| CGX-3075570 | 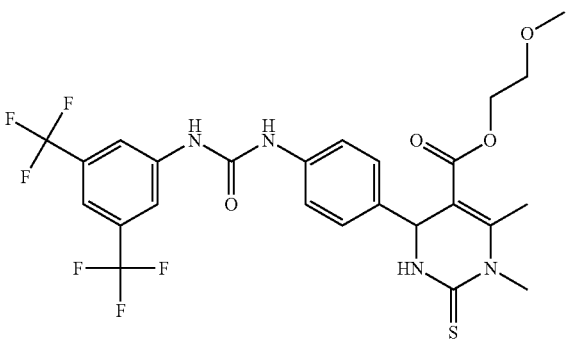 [SMILES: COCCOC(=O)C1=C(C)N(C)C(=S)NC1c1ccc(NC(=O)Nc2cc(C(F)(F)F)cc(C(F)(F)F)c2)cc1] |
| BAY 43-9006 | 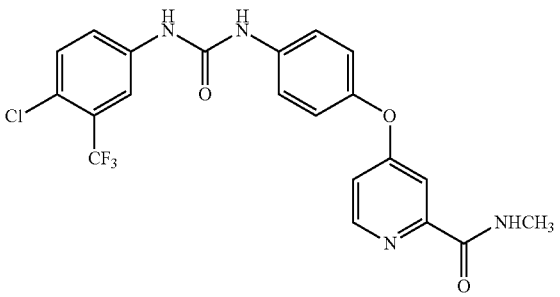 [SMILES: CNC(=O)c1cc(Oc2ccc(NC(=O)Nc3ccc(Cl)c(C(F)(F)F)c3)cc2)ccn1] |
| GK 00687 | 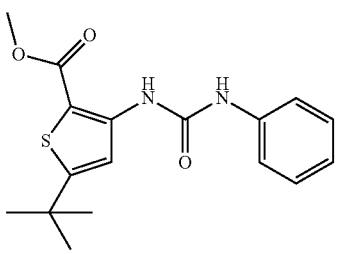 [SMILES: COC(=O)c1sc(C(C)(C)C)cc1NC(=O)Nc1ccccc1] |
| GK 00700 | 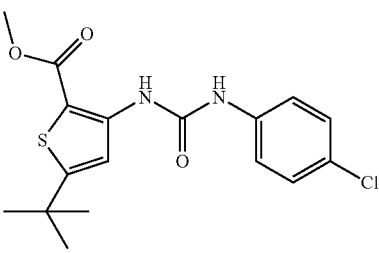 [SMILES: COC(=O)c1sc(C(C)(C)C)cc1NC(=O)Nc1ccc(Cl)cc1] |

TABLE 1-continued

Compounds according to certain exemplary embodiments.

| Compound Number | Structure |
|---|---|
| T1653 | methyl 5-tert-butyl-3-[[(thiophen-2-ylcarbamoyl)amino]]thiophene-2-carboxylate |
| T1649 | 1-(3-hydroxy-4-methylphenyl)-3-(4-chloro-3-trifluoromethylphenyl)urea |
| T1650 | 1-(3-hydroxy-4-methylphenyl)-3-(3,4-dichlorophenyl)urea |
| T1651 | 1-(3-hydroxy-4-methylphenyl)-3-(3,5-bis(trifluoromethyl)phenyl)urea |
| T1652 | 1-(3-hydroxy-4-methylphenyl)-3-phenylurea |
| T1654 | 1,3-bis(3,4-dichlorophenyl)urea |
| T1655 | 1,3-bis(4-chloro-3-trifluoromethylphenyl)urea |
| T1656 | 1,3-bis(3,5-bis(trifluoromethyl)phenyl)urea |
| T1657 | 1,3-diphenylurea |
| 1658 | 1,3-bis(3-nitrophenyl)urea |

TABLE 1-continued
Compounds according to certain exemplary embodiments.
| Compound Number | Structure |
|---|---|
| 1659 | 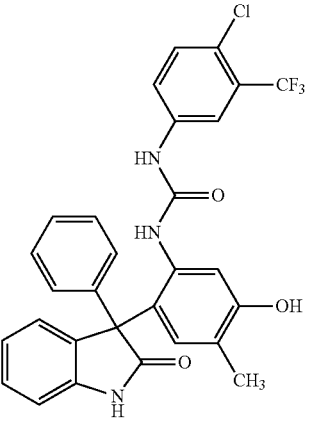 [SMILES: Cc1cc(C2(c3ccccc3)C(=O)Nc3ccccc32)c(NC(=O)Nc2ccc(Cl)c(C(F)(F)F)c2)cc1O] |
| 1660 | 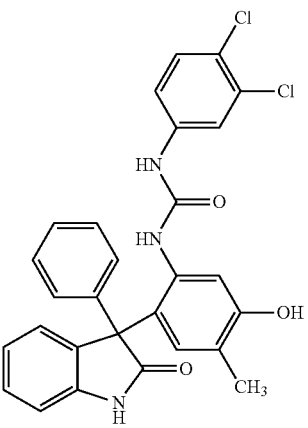 [SMILES: Cc1cc(C2(c3ccccc3)C(=O)Nc3ccccc32)c(NC(=O)Nc2ccc(Cl)c(Cl)c2)cc1O] |
| 1661 | 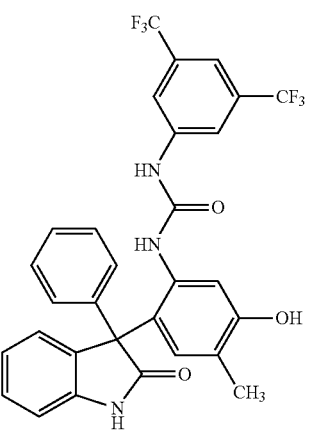 [SMILES: Cc1cc(C2(c3ccccc3)C(=O)Nc3ccccc32)c(NC(=O)Nc2cc(C(F)(F)F)cc(C(F)(F)F)c2)cc1O] |

TABLE 1-continued

Compounds according to certain exemplary embodiments.

| Compound Number | Structure |
|---|---|
| 1662 | 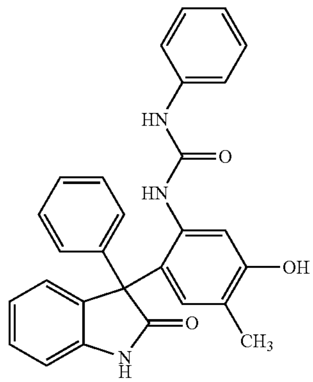 [SMILES: Cc1cc(C2(c3ccccc3)C(=O)Nc3ccccc32)c(NC(=O)Nc2ccccc2)cc1O] |
| 1663 | 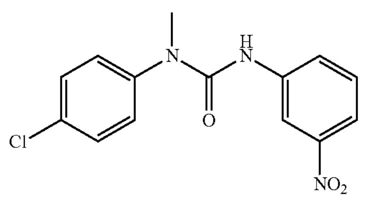 [SMILES: CN(C(=O)Nc1cccc([N+](=O)[O-])c1)c1ccc(Cl)cc1] |
| 1664 | 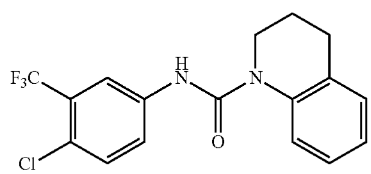 [SMILES: O=C(Nc1ccc(Cl)c(C(F)(F)F)c1)N1CCCc2ccccc21] |
| 1665 | 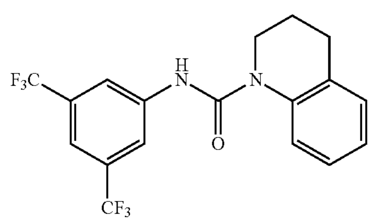 [SMILES: O=C(Nc1cc(C(F)(F)F)cc(C(F)(F)F)c1)N1CCCc2ccccc21] |
| 1778 | 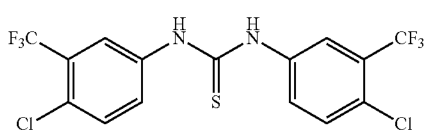 [SMILES: FC(F)(F)c1cc(NC(=S)Nc2ccc(Cl)c(C(F)(F)F)c2)ccc1Cl] |
| 1779 | 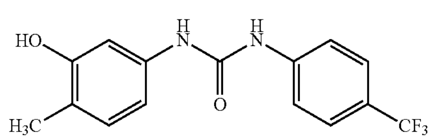 [SMILES: Cc1ccc(NC(=O)Nc2ccc(C(F)(F)F)cc2)cc1O] |
| 1780 | 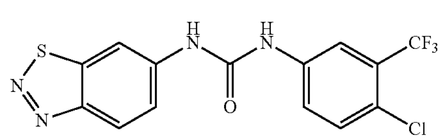 [SMILES: O=C(Nc1ccc(Cl)c(C(F)(F)F)c1)Nc1ccc2nnsc2c1] |
| 1781 | 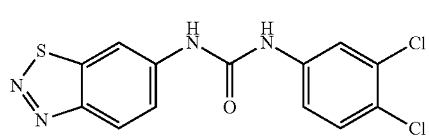 [SMILES: O=C(Nc1ccc(Cl)c(Cl)c1)Nc1ccc2nnsc2c1] |

TABLE 1-continued

Compounds according to certain exemplary embodiments.

| Compound Number | Structure |
|---|---|
| 1782 | 3,4-dichlorophenyl-N-methyl-N'-(4-chloro-3-trifluoromethylphenyl)urea |
| 1783 | N-(benzo[c][1,2,5]oxadiazol-5-yl)-N'-(4-chloro-3-trifluoromethylphenyl)urea |
| 1791 | N-(4-chloro-3-trifluoromethylphenyl)-N'-(2-cyanophenyl)urea |
| 1792 | N-(4-chloro-3-trifluoromethylphenyl)-N'-(3-cyanophenyl)urea |
| 1793 | N-(4-chloro-3-trifluoromethylphenyl)-N'-(4-cyanophenyl)urea |
| 1794 | N,N'-bis(benzo[c][1,2,5]oxadiazol-5-yl)urea |
| 1797 | N-(4-trifluoromethylphenyl)-N'-(3,4-dichlorophenyl)thiourea |
| 1798 | N-(3,5-bis(trifluoromethyl)phenyl)-N'-(3,4-dichlorophenyl)thiourea |
| 1799 | N-(3,4-dichlorophenyl)-N'-(4-chloro-3-trifluoromethylphenyl)thiourea |
| 1800 | N-(4-chlorophenyl)-N'-(3,5-bis(trifluoromethyl)phenyl)thiourea |

TABLE 1-continued
Compounds according to certain exemplary embodiments.
| Compound Number | Structure |
|---|---|
| 1801 | 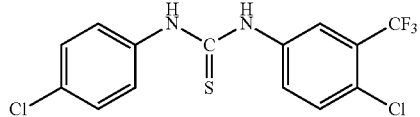 [SMILES: FC(F)(F)c1cc(NC(=S)Nc2ccc(Cl)cc2)ccc1Cl] |
| 1802 | 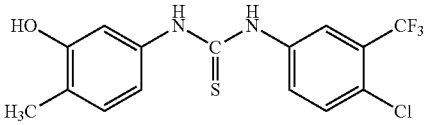 [SMILES: Cc1ccc(NC(=S)Nc2ccc(Cl)c(C(F)(F)F)c2)cc1O] |
| 1803 | 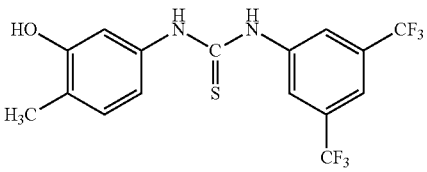 [SMILES: Cc1ccc(NC(=S)Nc2cc(C(F)(F)F)cc(C(F)(F)F)c2)cc1O] |
| 1804 | 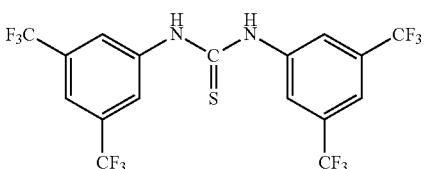 |
| 1805 | 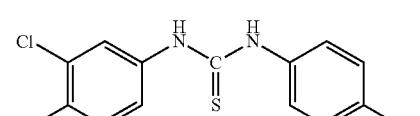 |
| 1806 | 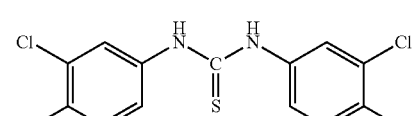 |
| 1809 | 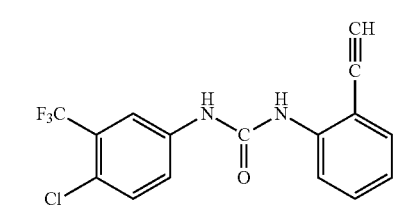 [SMILES: C#Cc1ccccc1NC(=O)Nc1ccc(Cl)c(C(F)(F)F)c1] |
| 1810 | 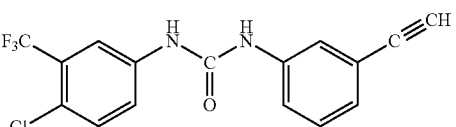 |
| 1811 | 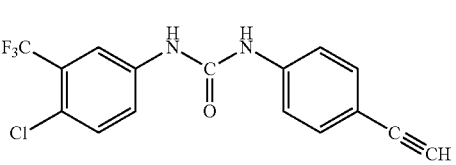 [SMILES: C#Cc1ccc(NC(=O)Nc2ccc(Cl)c(C(F)(F)F)c2)cc1] |

TABLE 1-continued

Compounds according to certain exemplary embodiments.

| Compound Number | Structure |
|---|---|
| 1812 | 1-(3-chloro-4-(trifluoromethyl)phenyl)-3-(4-chloro-3-(trifluoromethyl)phenyl)urea |
| 1813 | 1,3-bis(3-chloro-4-(trifluoromethyl)phenyl)urea |
| 1822 | 1-(4-chloro-3-(trifluoromethyl)phenyl)-3-(3-(1H-tetrazol-5-yl)phenyl)urea |
| 1823 | 1-(4-chloro-3-(trifluoromethyl)phenyl)-3-(4-(1H-tetrazol-5-yl)phenyl)urea |
| BLS17 | BLS17 |
| BLS13 | BLS13 |

In at least certain examples, the compounds disclosed here can be used in the treatment of cellular proliferative disorders, such as cancer and non-cancerous cellular proliferative disorders. Treatment of cellular proliferative disorders is intended to include, but is not limited to, inhibition of proliferation including rapid proliferation. As used herein, the term "cellular proliferative disorder" includes, but is not limited to, disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition (1995)). The terms "neoplasm" and "tumor" refer to an abnormal tissue that grows by cellular proliferation more rapidly than normal and continues to grow after the stimuli that initiated proliferation is removed. Id. Such abnormal tissue shows partial or complete lack of structural organization and functional coordination with the normal tissue which may be either benign (i.e., benign tumor) or malignant (i.e., malignant tumor).

Examples of general categories of cancer include, but are not limited to, carcinomas (i.e., malignant tumors derived from epithelial cells such as, for example, common forms of breast, prostate, lung and colon cancer), sarcomas (i.e., malignant tumors derived from connective tissue or mesenchymal cells), lymphomas (i.e., malignancies derived from hematopoietic cells), leukemias (i.e., malignancies derived from hematopoietic cells), germ cell tumors (i.e., tumors derived from totipotent cells. In adults most often found in the testicle or ovary; in fetuses, babies and young children, most often found on the body midline, particularly at the tip of the tailbone), blastic tumors (i.e., a typically malignant tumor which resembles an immature or embryonic tissue) and the like. One of skill in the art will understand that this list is exemplary only and is not exhaustive, as one of skill in the art will readily be able to identify additional cancers based on the disclosure herein.

Examples of specific neoplasms intended to be encompassed by the present invention include, but are not limited to, acute lymphoblastic leukemia; myeloid leukemia, acute myeloid leukemia, childhood; adrenocortical carcinoma; AIDS-related cancers; AIDS-related lymphoma; anal cancer; appendix cancer; astrocytoma (e.g., cerebellar, cerebral); atypical teratoid/rhabdoid tumor; basal cell carcinoma; bile duct cancer, extrahepatic; bladder cancer; bone cancer, osteosarcoma and malignant fibrous histiocytoma; brain tumor (e.g., brain stem glioma, central nervous system atypical teratoid/rhabdoid tumors, central nervous system embryonal tumors, cerebellar astrocytoma, cerebral astrocytoma/malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors); breast cancer; bronchial tumors; Burkitt lymphoma; carcinoid tumor (e.g., gastrointestinal); carcinoma of unknown primary; central nervous system (e.g., atypical teratoid/rhabdoid tumor, embryonal tumors (e.g., lymphoma, primary); cerebellar astrocytoma; cerebral astrocytoma/malignant glioma; cervical cancer; chordoma; chronic lymphocytic leukemia; chronic myelogenous leukemia; chronic myeloproliferative disorders; colon cancer; colorectal cancer; craniopharyngioma; cutaneous T-cell lymphoma; embryonal tumors, central nervous system; endometrial cancer; ependymoblastoma; ependymoma; esophageal cancer; Ewing family of tumors; extracranial germ cell tumor; extragonadal germ cell tumor; extrahepatic bile duct cancer; eye cancer (e.g., intraocular melanoma, retinoblastoma); gallbladder cancer; gastric cancer; gastrointestinal tumor (e.g., carcinoid tumor, stromal tumor (gist), stromal cell tumor); germ cell tumor (e.g., extracranial, extragonadal, ovarian); gestational trophoblastic tumor; glioma (e.g., brain stem, cerebral astrocytoma); hairy cell leukemia; head and neck cancer; hepatocellular cancer; Hodgkin lymphoma; hypopharyngeal cancer; hypothalamic and visual pathway glioma; intraocular melanoma; islet cell tumors; Kaposi sarcoma; kidney cancer; large cell tumors; laryngeal cancer (e.g., acute lymphoblastic, acute myeloid); leukemia (e.g., acute myeloid, chronic lymphocytic, chronic myelogenous, hairy cell); lip and/or oral cavity cancer; liver cancer; lung cancer (e.g., non-small cell, small cell); lymphoma (e.g., AIDS-related, Burkitt, cutaneous Tcell, Hodgkin, non-Hodgkin, primary central nervous system); macroglobulinemia, Waldenstrom; malignant fibrous histiocytoma of bone and/or osteosarcoma; medulloblastoma; medulloepithelioma; melanoma; merkel cell carcinoma; mesothelioma; metastatic squamous neck cancer; mouth cancer; multiple endocrine neoplasia syndrome; multiple myeloma/plasma cell neoplasm; mycosis fungoides; myelodysplastic syndromes; myelodysplastic/myeloproliferative diseases; myelogenous leukemia (e.g., chronic, acute, multiple); myeloproliferative disorders, chronic; nasal cavity and/or paranasal sinus cancer; nasopharyngeal cancer; neuroblastoma; non-Hodgkin lymphoma; non-small cell lung cancer; oral cancer; oral cavity cancer; oropharyngeal cancer; osteosarcoma and/or malignant fibrous histiocytoma of bone; ovarian cancer (e.g., ovarian epithelial cancer, ovarian germ cell tumor, ovarian low malignant potential tumor); pancreatic cancer (e.g., islet cell tumors); papillomatosis; paranasal sinus and/or nasal cavity cancer; parathyroid cancer; penile cancer; pharyngeal cancer; pheochromocytoma; pineal parenchymal tumors of intermediate differentiation; pineoblastoma and supratentorial primitive neuroectodermal tumors; pituitary tumor; plasma cell neoplasm/multiple myeloma; pleuropulmonary blastoma; primary central nervous system lymphoma; prostate cancer; rectal cancer; renal cell cancer; renal, pelvis and/or ureter, transitional cell cancer; respiratory tract carcinoma involving the nut gene on chromosome 15; retinoblastoma; rhabdomyosarcoma; salivary gland cancer; sarcoma (e.g., Ewing family of tumors, Kaposi, soft tissue, uterine); Sezary syndrome; skin cancer (e.g., non-melanoma, melanoma, merkel cell); small cell lung cancer; small intestine cancer; soft tissue sarcoma; squamous cell carcinoma; squamous neck cancer with occult primary, metastatic; stomach cancer; supratentorial primitive neuroectodermal tumors; T-cell lymphoma, cutaneous; testicular cancer; throat cancer; thymoma and/or thymic carcinoma; thyroid cancer; transitional cell cancer of the renal, pelvis and/or ureter; trophoblastic tumor; unknown primary site carcinoma; urethral cancer; uterine cancer, endometrial; uterine sarcoma; vaginal cancer; visual pathway and/or hypothalamic glioma; vulvar cancer; Waldenstrom macroglobulinemia; Wilms tumor and the like. For a review, see the National Cancer Institute's Worldwide Website (cancer.gov/cancertopics/alphalist). One of skill in the art will understand that this list is exemplary only and is not exhaustive, as one of skill in the art will readily be able to identify additional cancers and/or neoplasms based on the disclosure herein.

Examples of noncancerous cellular proliferative disorders includes fibroadenoma, adenoma, intraductal papilloma, nipple adenoma, adenosis, fibrocystic disease or changes of breast, plasma cell proliferative disorder (PCPD), restenosis, atherosclerosis, rheumatoid arthritis, myofibromatosis, fibrous hamartoma, granular lymphocyte proliferative disorders, benign hyperplasia of prostate, heavy chain diseases (HCDs), lymphoproliferative disorders, psoriasis, idiopathic pulmonary fibrosis, sclroderma, cirrhosis of the liver, IgA nephropathy, mesangial proliferative glomerulonephritis, membranoproliferative glomerulonephritis, hemangiomas, vascular and non-vascular intraocular proliferative disorders and the like. One of skill in the art will understand that this list is exemplary only and is not exhaustive, as one of skill in the art will readily be able to identify additional noncancerous cellular proliferative disorders based on the disclosure herein.

The language "treatment of cellular proliferative disorders" is intended to include, but is not limited to, the prevention of the growth of neoplasms in a subject or a reduction in the growth of pre-existing neoplasms in a subject, as well as the prevention or reduction of increased or uncontrollable cell growth. The inhibition also can be the inhibition of the metastasis of a neoplasm from one site to another. In certain embodiments, the neoplasms are sensitive to one or more compounds of Formulae I and II as described herein.

In accordance with certain other examples, methods for treating viral infections are also disclosed. Treatment of viral infections is intended to include, but is not limited to, the use of a N,N'-diarylurea and/or N,N'-diarylthiourea compounds described herein to prevent the initiation of viral protein synthesis. The term "viral infection," as used herein, refers to one or more cells which have been infected with a virus, such as a DNA or RNA animal virus. As used herein, RNA viruses include, but are not limited to, virus families such as picornaviridae (e.g., polioviruses), reoviridae (e.g., rotaviruses), togaviridae (e.g., encephalitis viruses, yellow fever virus, rubella virus), orthomyxoviridae (e.g., influenza viruses), paramyxoviridae (e.g., respiratory syncytial virus, measles virus, mumps virus, parainfluenza virus), rhabdoviridae (e.g., rabies virus), coronaviridae, bunyaviridae, flaviviridae, filoviridae, arenaviridae, bunyaviridae, and retroviridae (e.g., human T-cell lymphotropic viruses (HTLV), human immunodeficiency viruses (HIV)). As used herein, DNA viruses include, but are not limited to, virus families such as papovaviridae (e.g., papilloma viruses), adenoviridae (e.g., adenovirus), herpesviridae (e.g., herpes simplex viruses), and poxviridae (e.g., variola viruses). In certain embodiments, the viral infection is caused by hepatitis B virus, hepatitis C virus and/or HIV. One of skill in the art will understand that this list is exemplary only and is not exhaustive, as one of skill in the art will readily be able to identify additional viral infections based on the disclosure herein.

In accordance with other examples, methods for treating disorders associated with viral infections are disclosed. Treatment of one or more disorders associated with viral infections is intended to include, but is not limited to, the use of a N,N'-diarylurea and/or N,N'-diarylthiourea compound described herein to reduce or alleviate one or more symptoms of a viral infection. As used herein, the term "disorders associated with viral infection" refers to the host's response to infection by one or more viruses. Such responses include, but are not limited to neurological symptoms (e.g., encephalitis, meningoencephalitis, paralysis, myelopathy, neuropathy, aseptic meningitis, hemiparesis, dementia, dysphagia, lack of muscular coordination, impaired vision, coma, and the like), wasting symptoms (e.g., inflammatory cell infiltration, perivascular cuffing of blood vessels, demyelination, necrosis, reactive gliosis and the like), gastroenteritis symptoms (e.g., diarrhea, vomiting, cramps and the like), hepatitis symptoms (nausea, vomiting, right upper quadrant pain, raised liver enzyme levels (e.g., AST, ALT and the like), jaundice and the like), hemorrhagic fever symptoms (e.g., headache, fever, chills body pains, diarrhea, vomiting, dizziness, confusion, abnormal behavior, pharyngitis, conjunctivitis, red face, red neck, hemorrhage, organ failure and the like), oncogenic symptoms (e.g., sarcomas, leukemias and the like, as well as "rare" malignancies, e.g., Kaposi's sarcoma, oral hairy leukoplasia, lymphomas and the like), immunodeficiency symptoms (e.g., opportunistic infections, wasting, rare malignancies, neurological disease, fever, diarrhea, skin rashes and the like), lesions (e.g., warts (e.g., common wart, flat wart, deep hyperkaratotic palmoplantar wart, superficial mosaic type palmoplantar wart and the like), epidermodysplasia, mucosal lesions, ulcers and the like), and systemic symptoms (e.g., fever, chills, headache, muscle pain, bone pain, joint pain, pharyngitis, tonsillitis, sinusitis, otitis, bronchitis, pneumonia, bronchopneumonia, nausea, vomiting, increased salivation, rash, macules, lymphadenopothy, arthritis, ulcers, photosensitivity, weight loss, irritability, restlessness, anxiety, coma, death and the like). Disorders associated with viral infections are described in *Fields Virology* 4*th* Ed. (2001) Lippincott, Williams & Wilkins, and the introduction to medical virology website (web.uct.ac.za/depts./mmi/jmoodie/introvi2.html). One of skill in the art will understand that this list is exemplary only and is not exhaustive, as one of skill in the art will readily be able to identify additional disorders associate with viral infections based on the disclosure herein.

In accordance with other examples, methods for treating disorders characterized by unwanted synthesis and/or abnormal accumulation of one or more mutant and/or wild-type proteins are provided. Treatment of one or more disorders associated with unwanted synthesis and/or abnormal accumulation is intended to include, but is not limited to, the use of a N,N'-diarylurea and/or N,N'-diarylthiourea compound described herein to reduce or alleviate one or more symptoms characterized by unwanted synthesis and/or abnormal accumulation. Without intending to be bound by scientific theory, contacting a subject afflicted with a disorder characterized by unwanted synthesis and/or abnormal accumulation of one or more mutant and/or wild-type proteins with a compound described herein (e.g., a compound that can inhibit translation initiation) can reduce the load on the protein-folding machinery and, accordingly, may reduce the severity of the disorder. Disorders associated with unwanted synthesis and/or abnormal accumulation of one or more mutant and/or wild-type proteins include, but are not limited to, Tay-Sachs disease, cystic fibrosis, phenylketonuria, Fabry disease, Alzheimer's disease, Huntington's disease, Parkinson's disease, congophilic angiopathy, prion related disorders (i.e., transmissible spongiform encephalopathies such as Creutzfeldt-Jacob disease, kuru, fatal familial insomnia, scrapie, bovine spongiform encephalopathy and the like) and the like. One of skill in the art will understand that this list is exemplary only and is not exhaustive, as one of skill in the art will readily be able to identify additional disorders characterized by unwanted synthesis and/or abnormal accumulation of one or more mutant and/or wild-type proteins based on the disclosure herein.

In accordance with other examples, methods for treating non-proliferative, degenerative disorders associated with aberrant translation initiation using a N,N'-diarylurea and/or N,N'-diarylthiourea compound described herein to alleviate and/or reduce one or more symptoms associated with a non-proliferative, degenerative disorder are disclosed. Treatment of non-proliferative, degenerative diseases is intended to include, but is not limited to, the use of N,N'-diarylurea and/or N,N'-diarylthiourea compounds described herein. As used herein, the term "non-proliferative degenerative disorder" is intended to include, but is not limited to, diseases characterized by a loss of function of cells, tissues, and/or organs due to aberrant translation initiation. Non-proliferative degenerative disorders include, but are not limited to, disorders such as Alzheimer's disease and insulin resistance. One of skill in the art will understand that this list is exemplary only and is not exhaustive, as one of skill in the art will readily be able to identify additional non-proliferative degenerative disorders based on the disclosure herein.

In accordance with certain other examples, kits for treating one or more (1) proliferative disorders, (2) non-proliferative, degenerative disorders, (3) viral infections, and/or (4) disorders associated with viral infections are provided. In one example, the kit may comprise one or more compounds of Formulae I and II as described herein. In another example, the kit may comprise a pharmaceutically acceptable carrier. In an additional example, the kit may also include instructions for treating (1) proliferative disorders, (2) non-proliferative, degenerative disorders, (3) viral infections, (4) disorders associated with viral infections, and/or (5) disorders characterized by unwanted protein synthesis or diseases for which reducing protein synthesis is advantageous. In some examples, the kit may also comprise, e.g., a buffering agent, a preservative, or a protein stabilizing agent. In other examples, the kit may also contain a control sample or a series of control samples which can be assayed and compared to the test sample contained. Other suitable components for including in the kit will be selected by the person of ordinary skill in the art, given the benefit of this disclosure.

In accordance with certain examples, compounds of the present invention can be incorporated into pharmaceutical compositions suitable for administration. Such compositions typically comprise the compounds disclosed here and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In accordance with certain examples, a pharmaceutical composition of the invention is formulated to be compatible with its intended route of administration. Such pharmaceutical compositions may be administered by inhalation, transdermally, orally, rectally, transmucosally, intestinally, parenterally, intramuscularly, subcutaneously, intravenously or other suitable methods that will be readily selected by the person of ordinary skill in the art, given the benefit of this disclosure. For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

In accordance with other examples, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMPHOR EL™ (BASF, Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

In accordance with other examples, sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation can be vacuum drying and freeze-drying which yields a powder of the active ingredient plus any additional desired ingredient from a previously sterile-filtered solution thereof. Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In at least certain examples, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811, incorporated herein by reference in its entirety for all purposes.

In accordance with certain examples, pharmaceutical compositions of the invention comprise one or more N,N'-diarylurea and/or N,N'-diarylthiourea compounds covalently linked to a peptide (i.e., a polypeptide comprising two or more amino acids). Peptides may be assembled sequentially from individual amino acids or by linking suitable small peptide fragments. In sequential assembly, the peptide chain is extended stepwise, starting at the C-terminus, by one amino acid per step. In fragment coupling, fragments of different lengths can be linked together, and the fragments can also be obtained by sequential assembly from amino acids or by fragment coupling of still shorter peptides.

In both sequential assembly and fragment coupling it is necessary to link the units (e.g., amino acids, peptides, compounds and the like) by forming an amide linkage, which can be accomplished via a variety of enzymatic and chemical methods. The methods described herein for formation of peptidic amide linkages are also suitable for the formation of non-peptidic amide linkages.

Chemical methods for forming the amide linkage are described in detail in standard references on peptide chemistry, including Muller, *Methoden der organischen Chemie* Vol. XV/2, 1-364, Thieme Verlag, Stuttgart, (1974); Stewart and Young, *Solid Phase Peptide Synthesis,* 31-34 and 71-82, Pierce Chemical Company, Rockford, Ill. (1984); Bodanszky et al., Peptide Synthesis, 85-128, John Wiley & Sons, New York, (1976); *Practice of Peptide Synthesis*, M. Bodansky, A. Bodansky, Springer-Verlag, 1994 and other standard works in peptide chemistry. Methods include the azide method, the symmetric and mixed anhydride method, the use of in situ generated or preformed active esters, the use of urethane protected N-carboxy anhydrides of amino acids and the formation of the amide linkage using coupling reagents, such as dicyclohexylcarbodiimide (DCC), diisopropylcarbodiimide (DIC), 1-ethoxycarbonyl-2-ethoxy-1,2-dihydroquinoline (EEDQ), pivaloyl chloride, 1-ethyl-3-(3-dimethylaminopropyl)carbodiimide hydrochloride (EDCl), n-propane-phosphonic anhydride (PPA), N,N-bis (2-oxo-3-oxazolidinyl)amido phosphoryl chloride (BOP-Cl), bromo-tris-pyrrolidinophosphonium hexafluorophosphate (Py-Brop), diphenylphosphoryl azide (DPPA), Castro's reagent (BOP, PyBop), O-benzotriazolyl-N,N,N',N'-tetramethyluronium salts (HBTU), O-azabenzotriazolyl-N,N,N',N'-tetramethyluronuim salts (TATU), diethylphosphoryl cyanide (DEPCN), 2,5-diphenyl-2,3-dihydro-3-oxo-4-hydroxythiophene dioxide (Steglich's reagent; HOTDO), 1,1'-carbonyldiimidazole (CDI) and the like. The coupling reagents can be employed alone or in combination with additives such as N,N-dimethyl-4-aminopyridine (DMAP), N-hydroxy-benzotriazole (HOBt), N-hydroxybenzotriazine (HOOBt), N-hydroxysuccinimide (HOSu), 2-hydroxypyridine and the like.

In accordance with other examples, methods of modulating translation initiation for therapeutic purposes are disclosed. In one example, a method involves contacting a cell with an agent that inhibits translation initiation. An agent that inhibits translation initiation can be any one of the compounds described herein, such as a N,N'-diarylurea and/or N,N'-diarylthiourea compound. In at least certain examples, the compound modulates the depletion of intracellular calcium stores. Methods of modulating translation initiation can be performed in vitro (e.g., by culturing a cell with the agent) or, alternatively, in vivo (e.g., by administering the agent to a subject). Certain examples disclosed herein are directed to methods of treating an individual afflicted with a disease or disorder characterized by aberrant translation initiation. Examples of such disorders are described herein. In one embodiment, the method involves administering an agent (e.g., an agent identified by a screening assay described herein), or combination of agents that inhibits translation initiation. As used herein, an individual afflicted with a disease or disorder is intended to include both human and non-human mammals. Examples of non-human mammals include, but are not limited to, non-human primates, horses, cows, goats, sheep, dogs, cats, mice, rats, hamsters, guinea pigs and the like.

The present invention provides for both prophylactic and therapeutic methods of treating a subject for one or more (1) proliferative disorders, (2) non-proliferative, degenerative disorders, (3) viral infections, and/or (4) disorders associated with viral infection. In one aspect, the invention provides a method for preventing in a subject, a disease or condition associated with one or more (1) proliferative disorders, (2) non-proliferative, degenerative disorders, (3) viral infections, and/or (4) disorders associated with viral infection, by administering, to the subject one or more N,N'-diarylurea and/or N,N'-diarylthiourea compounds described herein to modulate one or more (1) proliferative disorders, (2) non-proliferative, degenerative disorders, (3) viral infections, and/or (4) disorders associated with viral infection. Administration of a prophylactic agent can occur prior to the manifestation of symptoms, such that a disease or disorder is prevented or, alternatively, delayed in its progression.

Another aspect of the invention pertains to therapeutic methods of treating one or more (1) proliferative disorders, (2) non-proliferative, degenerative disorders, (3) viral infections, and/or (4) disorders associated with viral infection for therapeutic purposes. Accordingly, in an exemplary embodiment, a therapeutic method of the invention involves contacting a subject with a N,N'-diarylurea and/or N,N'-diarylthiourea compound that therapeutically treats one or more (1) proliferative disorders, (2) non-proliferative, degenerative disorders, (3) viral infections, (4) disorders associated with viral infection, and/or (5) disorders characterized by unwanted protein synthesis or diseases for which reducing protein synthesis is advantageous.

One embodiment of the present invention involves a method of treating a translation initiation-associated disease or disorder which includes the step of administering a therapeutically and/or prophylactically effective amount of an agent which inhibits translation initiation to a subject. In another embodiment, a subject is administered a therapeutically and/or prophylactically effective amount that is effective to deplete intracellular calcium stores. As defined herein, a therapeutically and/or prophylactically effective amount of agent (i.e., an effective dosage) ranges from about 0.001 to 30 mg/kg body weight, from about 0.01 to 25 mg/kg body weight, from about 0.1 to 20 mg/kg body weight, from about 1 to 10 mg/kg, from about 2 to 9 mg/kg, from about 3 to 8 mg/kg, from about 4 to 7 mg/kg, or from about 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Treatment of a subject with a therapeutically and/or prophylactically effective amount of an inhibitor can include a single treatment or can include a series of treatments. It will also be appreciated that the effective dosage of in used for treatment may increase or decrease over the course of a particular treatment.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, and accompanying claims.

Example I

N,N'-Diarylurea Translation Initiation Inhibitors

Design and Development of a Ternary Complex Assay

Figure 2:
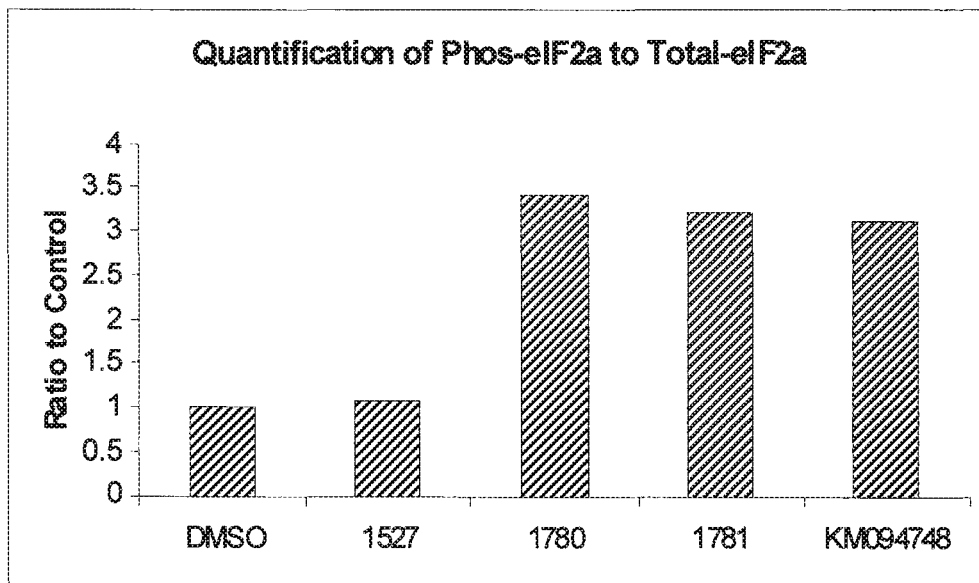
FIG. 2 graphically depicts quantification of phosphorylated eIF2α relative to total eIF2α.
Figure 6:
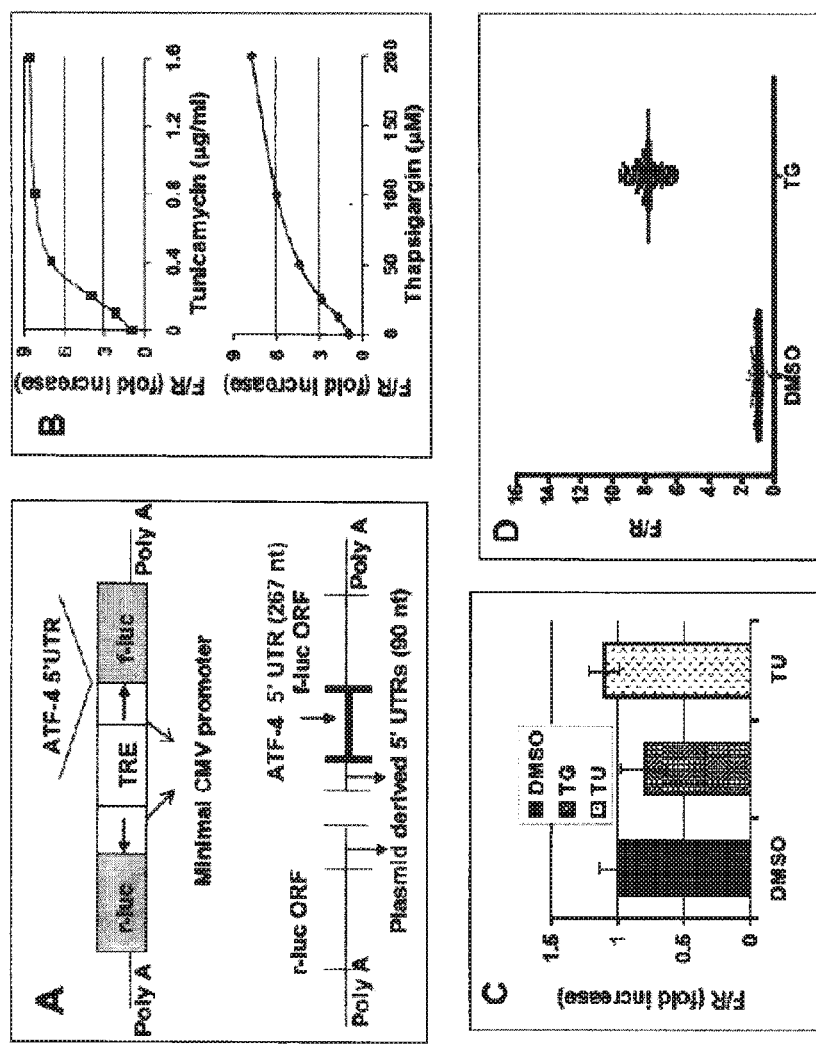
FIGS. 6A-6D depict the development and validation of the eIF2-GTP-Met-tRNA$_i$ ternary complex assay. A) Firefly and *renilla* luciferase open reading frames (ORFs) were cloned into pBISA plasmid to generate two mRNAs that differ only in their coding region (pBISA-DL, top). This vector was further modified by cloning 5' untranslated region (UTR) of mouse ATF-4 gene in frame with the AUG start codon of firefly luciferase ORF (pBISA-DL$^{(ATF-4)}$, bottom). B) pBISA-DL$^{(ATF-4)}$ construct was stably transfected into KLN-tTA cells and responsiveness of these cells to thapsigargin and tunicamycin was evaluated by a Dual Luciferase Assay (DLR assay). The firefly/*renilla* (F/R) ratio in vehicle treated cells was taken as 1. C) The second uORF in the ATF-4 5' UTR was fused in frame to AUG start codon of firefly luciferase to remove eIF2α phosphorylation dependent induction of ATF-4 translation, the plasmid was transiently transfected into KLN-tTA cells. The cells were treated with DMSO (vehicle) Thapsigargin (100 nM) or tunicamycin (1 µg/ml) and R/F ratio was determined by DLR assay. D) Stable KLN-tTA/pBISA-DL$^{(ATF-4)}$ cell line in B was plated into a 384 well plate, half the plate was treated with TG and other half with the vehicle (DMSO). Firefly/*renilla* ratio was determined by DLR assay and plotted.

For assay development, a bi-directional plasmid was designed in which a common promoter/enhancer complex drives the transcription of firefly luciferase (F-luc) ORF fused to the 5' untranslated region (UTR) of ATF-4, and of the *renilla* luciferase (R-luc) ORF fused to a 90-nucleotide 5' UTR derived from the plasmid (FIG. 6A). Because the tetracycline-regulated transactivator ((tTA), required for driving transcription from this vector) is not normally expressed in the mammalian cells, stable KLN cancer cells were constructed that expressed tTA (KLN-tTA).

The KLN-tTA colonies that drove expression of reporter genes from pBISA-DL plasmid were selected by transient transfection and dual luciferase assay. One of these KLN-tTA cell lines was transfected with the pBISA-DL$^{(ATF-4)}$ expression vector, stable colonies were selected by dual luciferase assay and expanded. To determine if reduced availability of the eIF2*GTP*Met-tRNA$_i$ ternary complex increased the translation of firefly luciferase and decreased translation of *renilla* luciferase, selected KLN-tTA/pBISA-DL$^{(AFT-4)}$ colonies were treated with thapsigargin (TG) or tunicamycin (TU), two agents known to cause phosphorylation of eIF2α. FIG. 6B shows that treatment with these agents increased the expression of firefly luciferase and decreased expression of *renilla* luciferase, leading to an increase in the ratio of firefly activity relative to *renilla* activity. This effect was due to presence of multiple uORFs but not other elements in the 5' UTR of ATF-4 (for example an internal ribosomal entry site, IRES, element) because removal of uORF2 by insertion of a single nucleotide abolished increased firefly/*renilla* ratio in TG or TU treated cells (FIG. 6C). Furthermore, the firefly/*renilla* ratio was increased only in response to decreased abundance of the ternary complex but not inhibition of cell growth because several anti-proliferative agents such as etoposite or mitomycin had no effect on Firefly luciferase/*Renilla* luciferase ratio, indicating that this assay is suitable for identification of agents that reduce abundance of the ternary complex (Table 6).

This assay was then adapted for high throughput screening in 96 and 384 well plates. This was done by evaluating the cell density, length of exposure to compounds, DMSO tolerance and optimum firefly and *renilla* substrate. We then challenged these cells with thapsigargin or DMSO. The scattered plot of these data is shown in FIG. 6D. Using these data, the suitability of the assay for high throughput screening in 384 well was determined by determining signal to background ratio and the Z-factor. Cell-based assays usually have higher variation than homogeneous in vitro assays due to position effect in the plate, and other variables associated with handling of cells and the plates. Overall, this assay had a very high signal to background ratio (approximately 100 for both luciferases), and a Z score of 0.58, an excellent value for a cell based assay.

Screening

Screening was conducted in 384 well white opaque plates (Nalge Nunc), 100 μl volume RPMI+10% fetal bovine serum. Cells were plated at the sub-confluent density of 10,000 cells/well, and allowed to attach for a period of 16-18 hours at 37° C., 5% $CO_2$. Compounds were added as 1 μl of a 1 mM DMSO stock solution for a final screening concentration of 10 μM, using low-volume tips for transfer (Molecular Bioproducts). Cells were then incubated in the presence of compound for an additional sixteen hours, again at 37° C., 5% $CO_2$. Following incubation 70 μl of the culture medium was removed from each well to allow for reagent addition and plates were allowed to equilibrate to room temperature for thirty minutes. Firefly luciferase reporter activity was then read by the addition of thirty microliters of Dual Glo Luciferase reagent (Promega), followed by one hour incubation at room temperature to allow for adequate signal buildup. Luminescence counting was conducted on a Microbeta Trilux using a 1 second read time. *Renilla* luciferase reporter activity was measured following addition of 30 μl Stop and Glo Luciferase reagent (Promega) and incubation identical to the one carried out for the firefly luciferase one.

Compound scores were interpreted as firefly luciferase activity divided by *renilla* luciferase activity, normalized to the plate's DMSO control. Using a preliminary screen of the NCI Diversity set as a guide (1990 compounds), a hit threshold of three times the DMSO control readout was chosen to achieve a target hit rate of 1%; wells with this threshold value typically fell three standard deviations from the plate mean. All data analysis was conducted using the BioAssay HTS software package (CambridgeSoft).

With this format, signal-to-noise and signal-to-background typically ran at 100 and 10 respectively, with thapsigargin (TG) an agent known to induce eIF2α phosphorylation at 100 nM.

102,709 compounds in the NCI Open Chemical Repository were then screened using this HTS assay. Of these, approximately 1200 compounds were identified as hits in the primary screen (1.2% hit rate). Initial hits were confirmed by repeating the same dual luciferase assay in 96 well plates. Briefly, 20,000 cells/well were plated in triplicate for each concentration (10, 5 and 2.5 μM) of the compounds. The compounds that increased firefly/*renilla* luciferase ratio at least three-fold above the same ratio in the DMSO treated wells were considered confirmed hits. The final number of confirmed hits was 648 (See Table 5).

Lead Scaffolds

Figure 7:
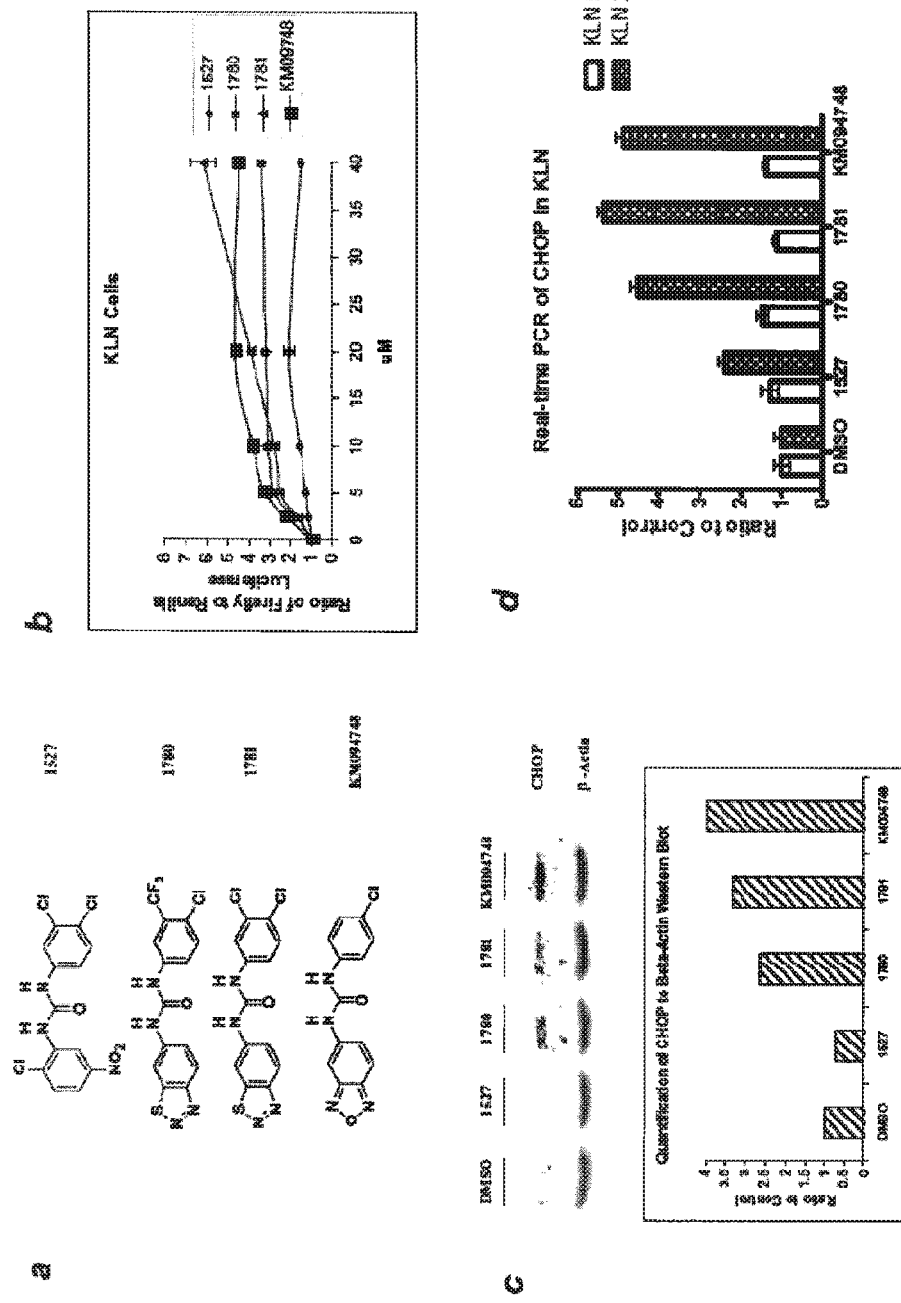
FIGS. 7A-7D depict the validation of N,N'-diarylureas as modifiers of the eIF2-GTP-Met-tRNA$_i$ ternary complex. A) The structure of three active and one inactive N,N'-diarylurea compounds selected for further studies. B) KLN-tTA/pBISA-DL$^{(ATF-4)}$ cells were incubated with the indicated concentrations of each N,N'-diarylurea compound and firefly/*renilla* (F/R) ratio was determined by DLR assay. C) KLN-tTA/pBISA-DL$^{(ATF-4)}$ cells were incubated with the indicated concentrations of each N,N'-diarylurea compound and expression of endogenous CHOP protein was determined by Western blot analysis. D) KLN-tTA/pBISA-DL$^{(ATF-4)}$ cells were incubated with 5 or 20 µM of each N,N'-diarylurea compound and expression of endogenous CHOP mRNA was determined by real time PCR analysis.

A review of the confirmed hits identified N,N'-diarylureas as a privileged scaffold that can provide attractive leads. Using commercially available sources we assembled a 120 member lead finding library of N,N'-diarylureas with various substitutions. Among these compounds three aryl-substituted active and one inactive N,N'-diarylureas were selected for further evaluation (FIG. 7A). FIG. 7B shows dose dependent effects of selected compounds on firefly/*renilla* luciferase ratio in KLN-tTA/pBISA-DL$^{(ATF-4)}$ cells.

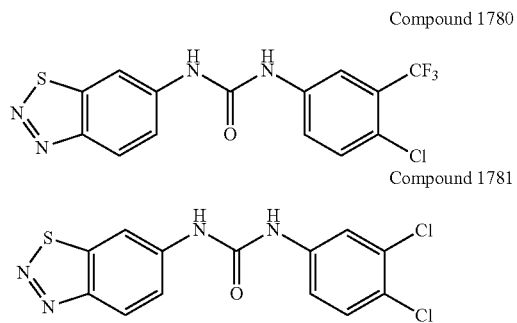

Compound 1780

Compound 1781

-continued

Compound 1527

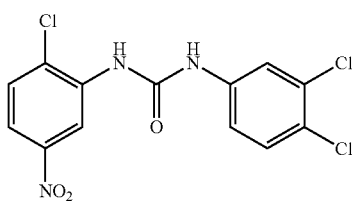

Compound KM09748

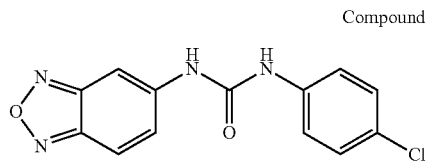

Characterization of N,N'-Diarylurea Compounds in Secondary Assays

In order to validate the N,N'-diarylurea compounds bona fide modifiers of the abundance of the eIF2-GTP-Met-tRNA$_i$ ternary complex, we determined effects selected active and inactive N,N'-diarylureas on endogenous cellular markers of the ternary complex. For example, reducing amount of the ternary complex increases translation of ATF-4, which results in elevated expression of CHOP mRNA and protein.

Figure 8:
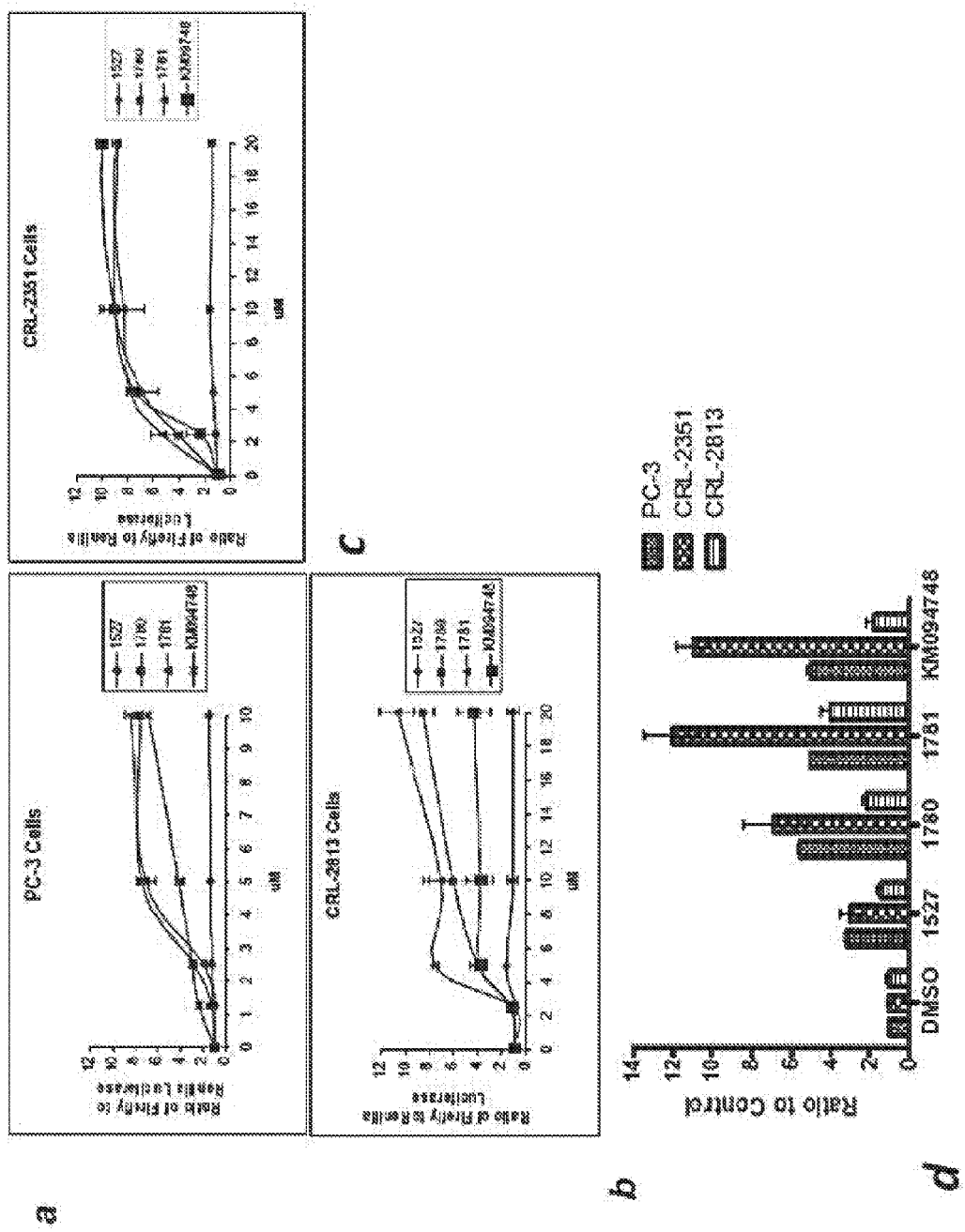
FIGS. 8A-8D depict that N,N'-diarylureas reduce the availability of the eIF2-GTP-Met-tRNA$_i$ ternary complex in human cancer cells. A-C) PC-3, CR-L2351, and CRL-2813 human cancer cell lines were co-transfected with pBISA-DL$^{(ATF-4)}$ and ptTA plasmids. One day post-transfection, the cells were treated with the indicated concentrations of N,N'-diarylureas. Firefly/renilla ratio was determined by DLR assay 8 hours after treatment. D) PC-3, CR-L2351, and CRL-2813 human cancer cell lines were treated with the indicated concentrations of N,N'-diarylureas four 8 hours, and expression of endogenous CHOP mRNA was determined by real-time PCR.

Therefore, expression of endogenous CHOP mRNA and CHOP protein in KLN-tTA/pBISA-DL$^{(ATF-4)}$ cells were utilized as secondary assays to validate N,N'-diarylurea compounds as modifiers of the eIF2•GTP•Met-tRNA$_i$ ternary complex. As shown in FIGS. 7C and D, active N,N'-diarylureas did indeed induce expression of CHOP mRNA and protein. These findings demonstrate that the ternary complex assay reported herein is a very valuable tool for screening the chemical repositories for the inhibitors of translation initiation that reduce the amount of the ternary complex. To rule out the possibility that the activity of N,N'-diarylurea compounds was confined to a single cell type, the effects of these compounds on the ternary complex assay and the expression of CHOP mRNA was assayed in CRL-2351, PC-3, CRL-2813 human breast, prostate, and melanoma cancer cell lines respectively. For the reporter gene assay, the three human cell lines were co-transfected with tTA expression vector and the pBISA-DL$^{(ATF-4)}$ dual luciferase expression vector shown in FIG. 6. As shown in FIGS. 8A-C, the active N,N'-diarylureas displayed significant activity in all the cell lines tested, albeit with different potencies. The expression of CHOP mRNA was assayed by real time PCR in the same cell lines treated with 5 or 20 µM of each compound. As shown in FIG. 8D, the effect of all four compounds on CHOP mRNA expression closely followed their effect in the firefly/*renilla* ratio.

The effect of certain compounds on ternary complex activity has been studied and the results presented below

| Compound Structure | Ternary Complex Activity | |
|---|---|---|
| | Maximum effect ($E_{max}$, fold over control) | Maximum effective dose $C_{max}$ (µM) |
| BLS17 | 13 | 10 |
| BLS14 | Inactive | Not applicable |
| BLS13 | 8.5 | 80 |

N'N'-Diarylurea Compounds Modify Availability of the eIF2-GTP-Met-tRNA$_i$ Ternary Complex by Causing Phosphorylation of eIF2α

The amount of the eIF2 GTP Met-tRNA$_i$ complex can be reduced by phosphorylation of eIF2α, reduced expression of Met-tRNA$_i$, or eIF2α phosphorylation independent reduction in the activity of eIF2B, the eIF2 guanine nucleotide exchange factor. To determine which of these was the case, the effect of active N,N'-diarylureas on the phosphorylation of eIF2α was studied. KLN-tTA/pBISA-DL$^{(ATF-4)}$ or PC-3 prostate cancer cells were incubated with three active and one inactive N,N'-diarylurea compounds and determined the phosphorylation of eIF2α by Western blot analysis. As shown in FIG. 9A, three N,N'-diarylureas that increased firefly/renilla luciferase ratio and induce endogenous CHOP also caused the phosphorylation of eIF2α, whereas the inactive N,N'-diarylurea compound had no effect on eIF2α phosphorylation. To determine if the phosphorylation of eIF2α was responsible for reduced amount of the ternary complex in the cells treated with N,N'-diarylurea compounds, previously generated PC-3 human prostate cancer cell lines in which expression of endogenous eIF2α was replaced with recombinant wild type (WT) or non-phosphorylatable eIF2α-S51A were utilized. These cells were co-transfected with tTA and pBISA-DL$^{(ATF-4)}$ dual luciferase expression vector and treated with three active and one inactive N,N'-diarylurea compounds. FIG. 9B demonstrates replacement of endogenous eIF2α with the non-phosphorylated eIF2α-S51A abrogated the activity of N,N'-diarylureas in this assay. These finding demonstrate conclusively that N,N'-diarylurea compounds reduce the amount of the ternary complex by causing phosphorylation of eIF2α.

N,N'-Diarylurea Compounds Reduce Expression of Cyclin D1

Figure 11:
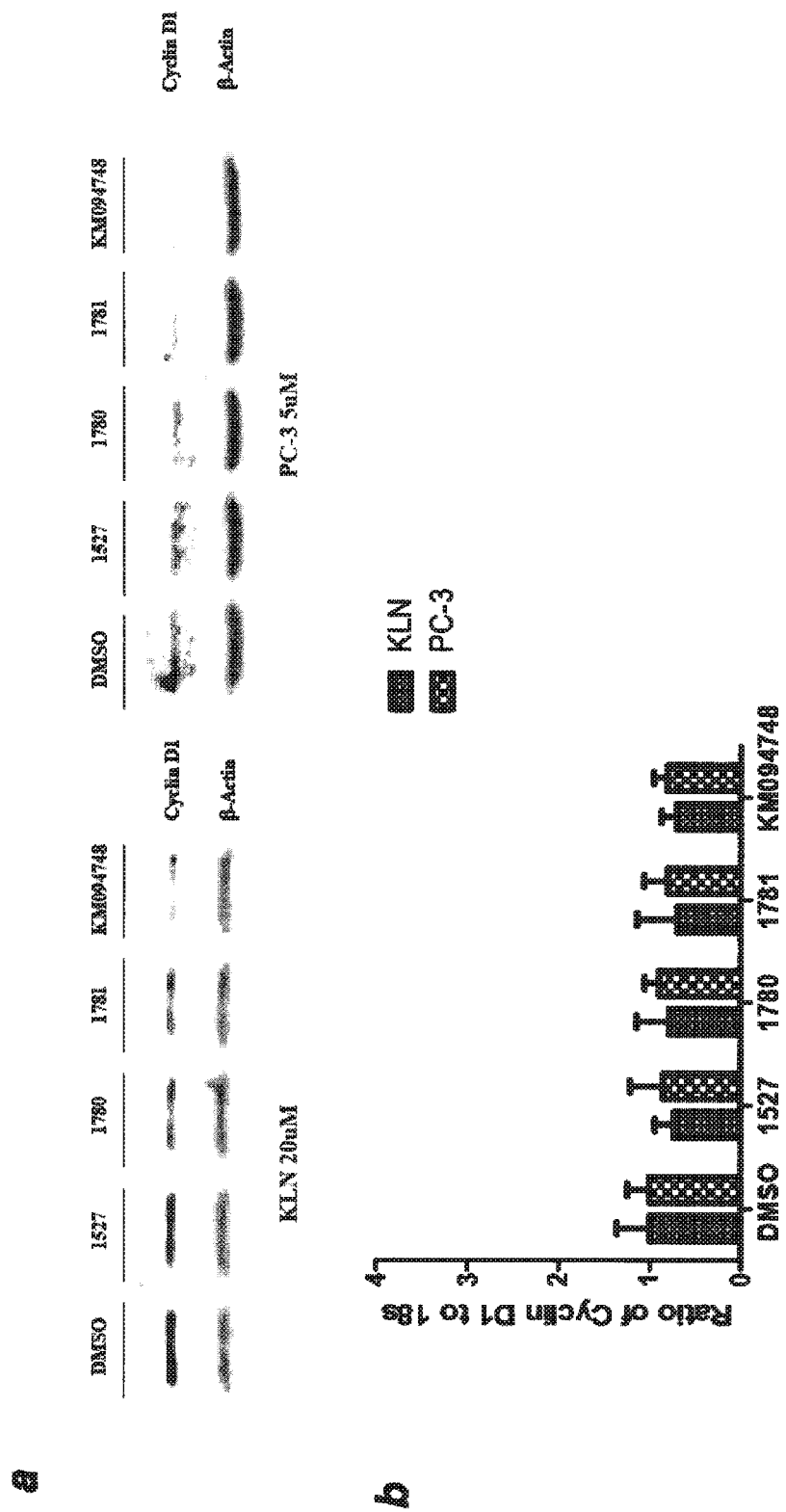

As shown in FIG. 11, active N,N'-diarylurea compounds inhibited cyclin D1 protein expression without any effect on p27$^{Kip1}$ protein. These agents had no effect on the level of cyclin D1 mRNA indicating that they inhibit cyclin D1 expression at the level of translation.

N,N'-Diarylurea Compounds Specifically Activate Heme Regulated Inhibitor (HRI)

Figure 12:
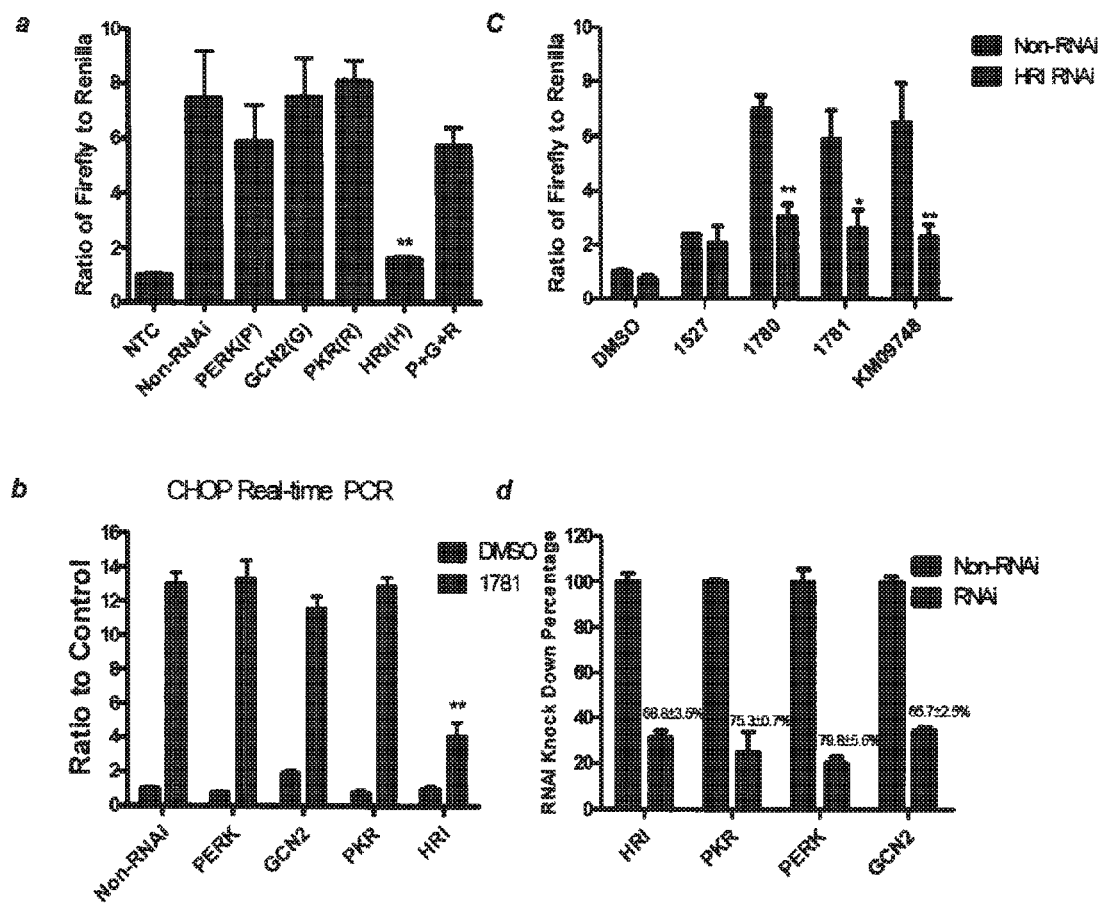

Four distinct kinases are shown to specifically phosphorylate eIF2α in response to the metabolic state of the cells or external stimuli. These are PKR, PKR-like endoplasmic reticulum kinase (PERK), general control derepressible kinase 2 (GCN2), and heme regulated inhibitor. To determine if N,N'-diarylurea compounds cause phosphorylation of eIF2α by causing activation of one or more of these kinases, knockdown expression of these kinases was assayed in KLN-tTA/pBISA-DL$^{(ATF-4)}$ cells individually or in combinations, treating the cells with compound #1781 or DMSO. As seen in FIG. 12A, knocking down the expression of PKR, PERK, or GCN had no effect on the induction of F-luc/R-luc ratio by compound #1781. In contrast, knocking down the expression of HRI almost completely abrogated activity of the compound #1181 (FIG. 12A). Furthermore simultaneous knocking down of PKR, PERK, and GCN2 failed to abrogate effects of #1781 indicating that these three kinases do not play a role in the induction of eIF2α phosphorylation by N,N'-diarylurea compounds. Furthermore real-time PCR analysis revealed that knocking down HRI expression but not that of PKR, PRK or GCN2 abrogated induction of CHOP mRNA by compound #1781, further supporting the finding that the HRI is the molecular target of N,N'-diarylurea compounds (FIG. 12B). To further confirm these data, KLN-tTA/pBISA-DL$^{(ATF-4)}$ cells were transfected with or without siRNA against HRI followed by their treatment with one inactive and three active N,N'-diarylurea compounds or vehicle. As shown in FIG. 11C, knocking down the expression of HRI abrogated induction of R-luc/R-luc ratio (indicative of the limited availability of the ternary complex) by all three active compounds with no effect on the inactive compound (FIG. 11C). Finally, all four kinases were knocked down by about the same efficiency, ruling out the possibility that the lack of effect by PKR, PERK, and GCN2 was due to failure of siRNA knockdown (FIG. 11D). Taken together these data clearly demonstrated that N,N'-diarylurea compounds cause phosphorylation of eIF2α specifically by activating HRI.

Heme Regulated Inhibitor (HRI) Mediates Phosphorylation of eIF2α by N,N'-Diarylureas Further studies were done to determine which eIF2α kinase(s) mediate phosphorylation of eIF2α by N,N'-diarylureas. In accordance with this aspect, the expression of each one of the four eIF2α kinases was knocked down either individually or in all possible combinations. Mouse KLN-tTA/pBISA-DL$^{(ATF-4)}$ and human CRL-2813 melanoma cells were transfected with siRNAs targeting PKR, GCN2, PERK or HRI, which knocked down their respective mRNAs with 70-80% efficiency (see data presented in Table 1).

TABLE 1

Efficiency of siRNAs in knocking down the expression of eIF2☐ kinase mRNAs in KLN-tTA/pBISA-DL$^{(ATF-4)}$ and CRL-2813 cancer cells.

| | Knockdown efficiency (%) | | | |
|---|---|---|---|---|
| | PERK | GCN2 | PKR | HRI |
| KLN | 68.8 ± 3.5 | 75.3 ± 0.7 | 79.8 ± 5.6 | 65.7 ± 2.5 |
| CRL-2813 | 82.5 ± 5.7 | 80.3 ± 1.5 | 69.4 ± 2.6 | 70.5 ± 3.4 |

Figure 13:
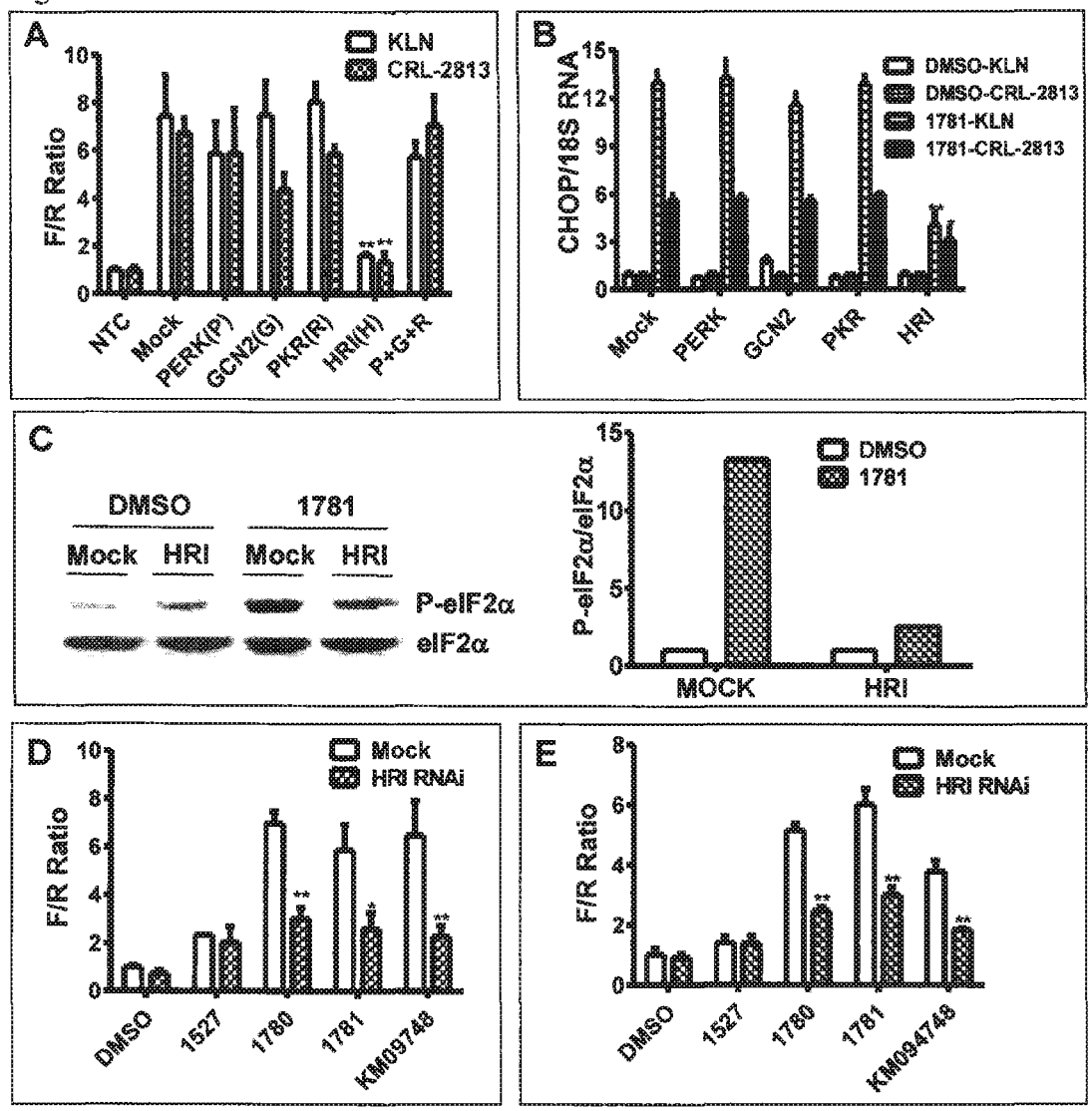

The co-transfected cells were treated with vehicle or an active N,N'-diarylurea, compound #1781, and determined the normalized F-luc/R-luc ratio. FIG. 13A shows that reduced expression of HRI significantly abrogated the activity of #1781. In sharp contrast, knocking down PKR, PERK, or GCN2 expression either individually or in double or triple combination had no effect on the activity of #1781. Consistent with these results, silencing HRI but not the other eIF2α kinases abrogated the increased expression of CHOP mRNA induced by compound #1781 (FIG. 13B). Furthermore, silencing of HRI reduced the induction of eIF2α phosphorylation by #1781 (FIG. 13C). Finally, studies in additional cell lines with N,N'-diarylureas showed that knocking-down expression of HRI but not other eIF2 kinases abrogated the effect of all active N,N'-diarylureas on the ternary complex abundance in these cell lines (FIGS. 13D and 13E). Taken together, these data demonstrate that activation of HRI mediates the phosphorylation of eIF2α, the reduced availability of the ternary complex and the other downstream effects induced by active N,N'-diarlyureas.

N,N'-Diarylureas Activate HRI in Cell-Free Lysates

Figure 14:
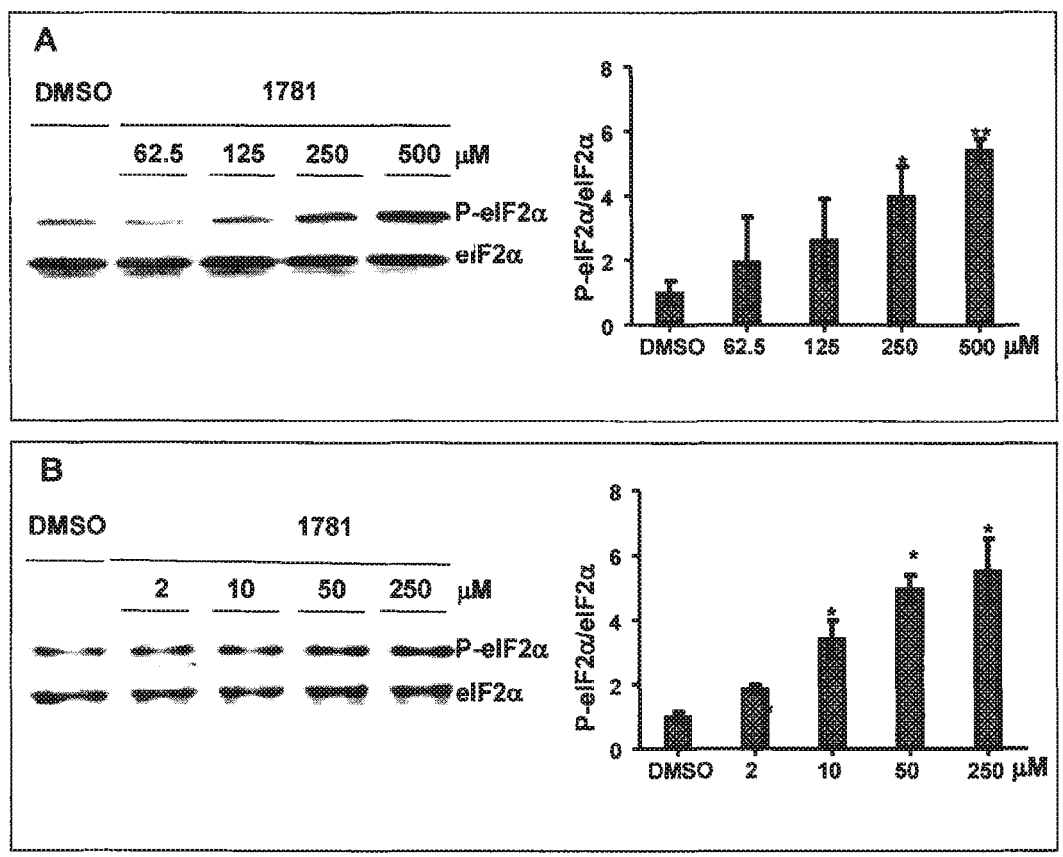

Compound #1781 was added to lysates of CRL-2813 cells or heme-supplemented rabbit reticulocytes and phosphorylation of eIF2α by Western blot was determined. As shown in FIG. 14, compound #1781 caused phosphorylation of eIF2α in cell lysates in a dose dependent manner ruling out the possibility the N,N'-diarylureas activate HRI due to cellular cytotoxicity.

N,N'-Diarylureas Inhibit Cell Proliferation by Reducing the Availability of the eIF2•GTP•Met-tRNA$_i$ Ternary Complex Reduced availability of the ternary complex causes inhibition of translation initiation and thereby of cell proliferation. Cell proliferation was selected as a biological response parameter to demonstrate target specificity and in vitro potency of N,N'-diarlyureas. The effects of N,N'-diarlyureas on the proliferation KLN mouse squamous cell carcinoma, CRL-2351 human breast, CRL-2813 human melanoma, A549 human lung and PC-3 human prostate cancer cell lines were tested. N,N'-diarylureas active in the ternary complex assay were potent inhibitors of cells proliferation (see data presented in Table 2).

TABLE 2

Effect of N,N -diarylureas on proliferation of human cancer cells

| | $IC_{50}$ *(µM) | | | |
|---|---|---|---|---|
| Cell line | 1527 | 1780 | 1781 | KM094748 |
| PC-3 | 8.3 | 0.9 | 1.1 | 1.4 |
| KLN | >20 | 14.8 | 17.1 | 8.5 |
| CRL-2813 | 20 | 0.1 | 0.5 | 0.3 |
| CRL-2351 | 9.5 | 1.3 | 3.0 | 0.1 |
| A549 | >20 | 0.8 | 1.2 | 1.3 |

*Concentration of compound that inhibit cell proliferation by 50%.

Figure 15:
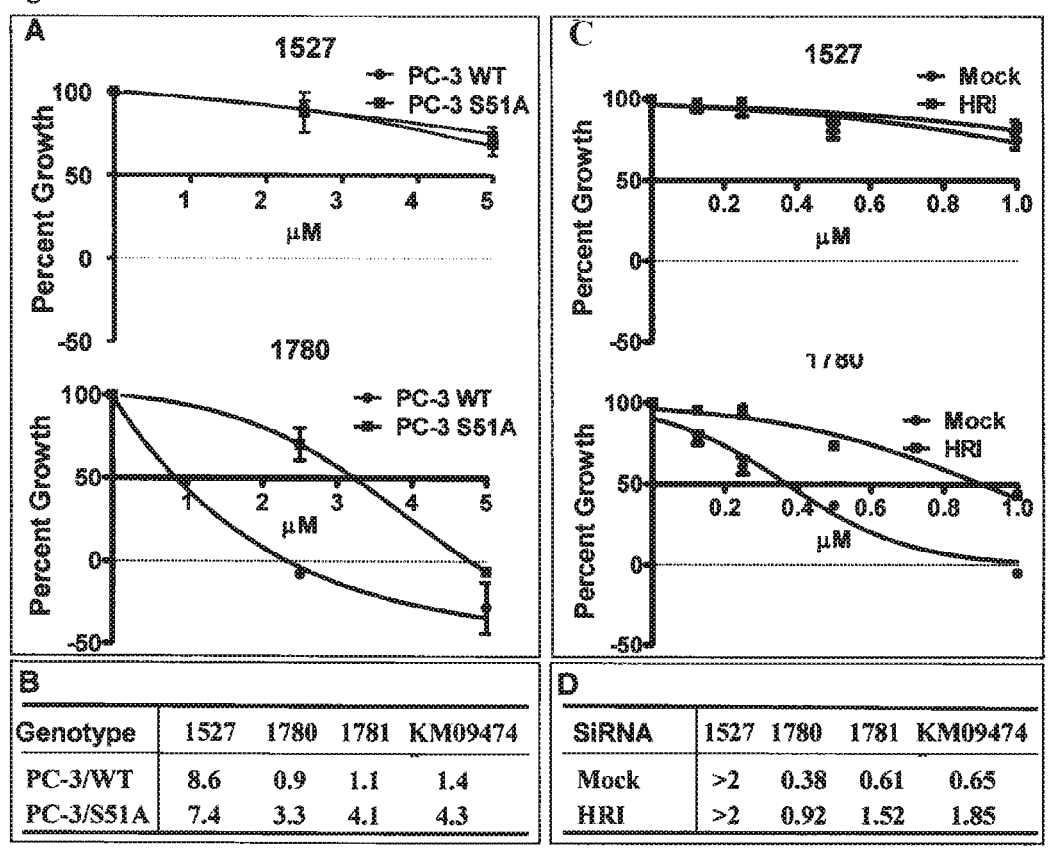

To determine if N,N'-diarylureas inhibit cell proliferation by reducing the availability of the ternary complex, the effect of N,N'-diarylureas on proliferation of previously described transgenic PC-3 human prostate cancer cell lines expressing either the non-phosphorylatable eIF2α-S51A mutant or the eIF2α-WT was studied. The results of these studies, shown in FIGS. 15A and 15B demonstrate that PC-3 cancer cells expressing the non-phoshorylatable eIF2α-S51A mutant were resistant while those expressing eIF2α-WT were sensitive to the inhibition of cell proliferation by N,N'-diarylureas. Reducing the expression of HRI, the eIF2α kinase that mediates N,N'-diarlyurea induced phosphorylation of eIF2α similarly abrogates the effect of these agents on cell proliferation (FIGS. 15C and 15D). Taken together, these data demonstrate that N,N'-diarlyureas possess the required potency and specificity to interrogate the role of the eIF2-GTP-Met-tRNA$_i$ ternary complex in normal physiology and pathobiology of human disorders.

Expression of HRI Correlates with the Sensitivity of Cancer Cells to N,N'-Diarylureas To determine correlate the sensitivity of the various cell lines to anti-proliferative effects of N,N'-diarylureas with the expression of HRI, cell lysates were probed with anti-HRI antibodies and relative level of HRI expression was correlated with the inhibition of cell proliferation exerted by N,N'-diarylureas. KLN cells, which express undetectable levels of HRI are very resistant to inhibition of cell proliferation by N,N'-diarylureas whereas CRL-2813 cells that express high level of HRI are most sensitive (see Table 2 and FIG. 16).

N,N'-Diarylureas Display No Apparent Toxicity In Vivo

To study toxicity effects, mice were treated with various doses of compound #1781 or vehicle. As shown in FIG. 17, seven consecutive day administration of #1781 had no adverse effect on weight gain or food consumption of mice even at the highest dose tested indicating that N,N'-diarylureas can be utilized to probe normal and patho-biology of the ternary complex in vivo.

Discussion

The ternary complex assay described herein is particularly robust because expression of both reporters is controlled by the same enhancer/promoter complex, therefore any effect of the test compounds on the transcription will be same for both reporters. Furthermore any effect of the test compounds on translation elongation or termination will be similar for both reporters. Because of these features, the ternary complex assay described herein controls for many variables at once. In addition, the primary assay is backed by the secondary assays such as the expression of CHOP protein and mRNA, which faithfully reflects the abundance of the ternary complex. The specificity of the assay was further demonstrated by testing well-known anti-cancer agents for their effects on the abundance of the ternary complex. None of these anti-cancer agents with no known effect on the formation of the ternary complex showed any activity, indicating that this assay is suitable for identification of mechanism specific active compounds. In addition to identifying privileged scaffolds that could be utilized for design of focused libraries for lead generation, a library of N,N'-diarylureas was prepared and studied using the ternary complex assay. Further characterization of selected compounds indicated that N,N'-diarylurea compounds reduced the amount of the ternary complex by causing phosphorylation of eIF2α. These findings indicate that the ternary complex assay is highly suitable for guiding development of translation initiation inhibitors, and that these N,N'-diarylurea compounds do in fact display potent anti-proliferative activity correlated with their activity in the ternary complex assay.

The data described herein indicate that the active N,N'-diarylurea compounds cause phosphorylation of eIF2α, induce expression of CHOP mRNA and protein and potently inhibit cell proliferation. The N,N'-diarylurea compounds also preferentially inhibited expression of cyclin D1. The data presented herein demonstrate that phosphorylation of eIF2α by N,N'-diarylurea compounds is required for reducing amount of the ternary complex by these agents. It was further demonstrated that N,N'-diarylureas compounds inhibit cell proliferation by causing phosphorylation of eIF2α with $IC_{50}$ values in the low/sub-micromolar range.

The data presented herein demonstrates the clear potential for targeting of the eIF2-GTP-Met-tRNA$_i$ ternary complex in a cell based high throughput screening campaign to develop translation initiation inhibitors and potential of N,N'-diarylurea compounds for development of novel mechanism specific agents for cancer therapy.

Materials and Methods

Cell Growth Assay: Cell growth was measured by the SRB assay.

Plasmids: The bi-directional mammalian expression vector pBI (Clontech, CA) was modified to expand the multiple cloning sites MCSs and thereafter named pBISA. This vector contains seven copies of the tetracycline regulated transactivator response element (TRE), which together act as core promoter/enhancer. The TRE is flanked on both sides by minimal human cytomegalovirus (CMV) minimal promoters allowing bi-directional transcription and two (MCS). Firefly and *renilla* luciferases were subcloned into MCS-I and MCS-II, respectively. This base plasmid, designated pBISA-DL, transcribes two mRNAs that contain the 90 nucleotide plasmid derived 5' UTR (same sequence in both mRNAs), and the ORF encoding either firefly or *renilla* luciferase followed by a polyadenylation sequence. This plasmid was further modified by inserting the 5' UTR of ATF-4 into MCS-I in front of the firefly luciferase mRNA. Transcription from this direction generates an mRNA that contains the firefly luciferase ORF preceded by a 5' UTR composed of 90 nucleotides derived from the plasmid and 267 nucleotides derived from the 5' UTR of ATF-4 mRNA. Transcription from the other direction generates an mRNA that contains the *renilla* luciferase ORF preceded only by the 90-nucleotide plasmid-derived sequence in the 5' UTR (FIG. 1B). This expression plasmid is called pBISA-DL$^{(ATF-4)}$.

Stable and transient transfection: Cells were seeded at the density of $10^5$ in 60-mm (stable transfection) or $10^4$ cells per well of 96-well plate (transient transfection) plates and transfected one day later using the Qiagen Transfectamine transfection kit. For selection of stable cell lines, transfected cells were transferred to 100-mm plates and selected with appropriate antibiotics.

Western blotting: Cell extracts were separated by SDS-PAGE and probed with anti-phosphoserine-51-eIF2α (PS51-eIF2α), anti-total eIF2α-specific antibodies (PS51-eIF2α (Biosource International, Hopkinton, Mass.), anti-CHOP, or anti β-actin (Santa Cruz Biotechnology, CA) as described.

Robotics: Liquid handling was conducted on a Biomek FX (Beckman Coulter). Luminescence measurements were conducted on a Microbeta Trilux (Perkin Elmer). Both are components on a Sagian Core robotic platform (Beckman Coulter).

Dual luciferase assay: Cells or minced tumors expressing firefly and *renilla* luciferases were lysed and the extracts assayed with a glow type dual luciferase assay kit, per manufacturer's instruction (Promega Inc., Madison, Wis.).

Real time PCR: For real time PCR, total RNA was extracted with TaqMan Gene Expression Cells-to-Ct™ Kit (Applied Biosystems, Branchburg, N.J.) according to manufacturer's protocol. Contaminating DNA was removed by DNase I treatment. 1-Step Real-time PCR was performed on a Bio-Rad iCycler IQ5 system by using B-R 1-Step SYBR Green qRT-PCR Kit (Quanta BioSciences, Gaithersburg, Md.) according to manufacturer's specifications. The thermal cycler conditions were as follows: 10 minutes at 50° C., hold for 5 minutes at 95° C., followed by 2-step PCR for 45 cycles of 95° C. for 15 seconds followed by 60° C. for 30 seconds. All PCRs were performed triplicate in independent PCR runs. Mean values of these repeated measurements were used for calculation. To calibrate the results, all the transcripts quantities were normalized to 18S rRNA (was 18S ribosomal RNA-like mRNA in mouse). The following primers were used in real-time PCR reactions:

```
Human CHOP
                            (SEQ ID NO: 1)
5' AGAACCAGGAAACGGAAACAGA 3'

(SEQ ID NO: 2)
5' TCTCCTTCATGCGCTGCTTT 3'

Mouse CHOP
                            (SEQ ID NO: 3)
5' CATACACCACCACACCTGAAAG 3'

(SEQ ID NO: 4)
5' CCGTTTCCTAGTTCTTCCTTGC 3'

Human Cyclin D1
                            (SEQ ID NO: 5)
5' CGGAGGAGAACAAACAGA 3'

(SEQ ID NO: 6)
5' TGAGGCGGTAGTAGGACA 3'

Mouse Cyclin D1
                            (SEQ ID NO: 7)
5' TACCGCACAACGCACTTTCTT 3'

(SEQ ID NO: 8)
5' CGCAGGCTTGACTCCAGAAG 3'

Human/Mouse 18s rRNA
                            (SEQ ID NO: 9)
5' CGGCGACGACCCATTCGAAC 3'

(SEQ ID NO: 10)
5' GAATCGAACCCTGATTCCCCGTC 3'
```

Example II

Structure-Activity Relationship (SAR) Study of N,N'-Diarylureas as Inhibitors of Translation Initiation, Potent Anti-Cancer Agents The general synthetic approaches to produce N,N'-diarylurea compounds of the present invention are set forth below.

Chemistry

The first series of molecules in this example, most of which are symmetrical N,N'-diarylureas substituted by heteroatoms or groups of heteroatoms, was prepared by using appropriate commercially available aryl isocyanates and aryl amines according to Scheme 1.

Scheme 1:

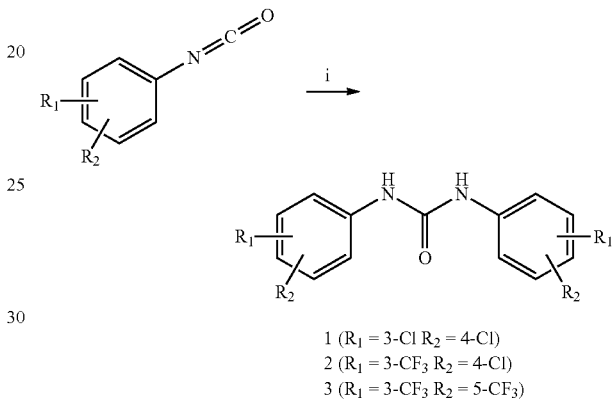

1 ($R_1$ = 3-Cl $R_2$ = 4-Cl)
2 ($R_1$ = 3-$CF_3$ $R_2$ = 4-Cl)
3 ($R_1$ = 3-$CF_3$ $R_2$ = 5-$CF_3$)

Reagents and conditions: (i) anilines, 1,4-dioxane, 55° C.

The synthesis of compounds 1-3 was carried out in one step in 1,4-dioxane at 55° C. overnight. The same simple procedure using 5-aminocresol or 3-methoxy-4-methylaniline as new starting aryl amines was followed for the elaboration of the unsymmetrical N,N'-diarylureas 4-9 according to Scheme 2.

Scheme 2:

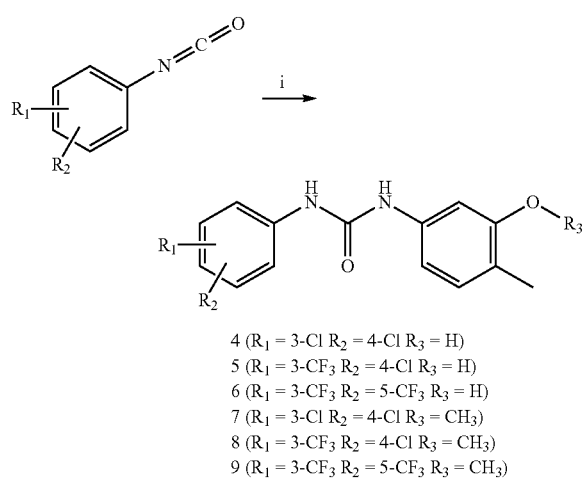

4 ($R_1$ = 3-Cl $R_2$ = 4-Cl $R_3$ = H)
5 ($R_1$ = 3-$CF_3$ $R_2$ = 4-Cl $R_3$ = H)
6 ($R_1$ = 3-$CF_3$ $R_2$ = 5-$CF_3$ $R_3$ = H)
7 ($R_1$ = 3-Cl $R_2$ = 4-Cl $R_3$ = $CH_3$)
8 ($R_1$ = 3-$CF_3$ $R_2$ = 4-Cl $R_3$ = $CH_3$)
9 ($R_1$ = 3-$CF_3$ $R_2$ = 5-$CF_3$ $R_3$ = $CH_3$)

Reagents and conditions: (i) anilines, 1,4-dioxane, 55° C.

Analogs 11-13 and 15-17 were prepared in a slightly different manner. The synthesis began by the elaboration of two different substituted anilines starting from 2-methyl-5-nitrophenol. Compound 10, which was the precursor of N,N'-diarylureas 11-13, was obtained via a classic Mitsunobu coupling reaction in presence of N,N-dimethylethanolamine according to Scheme 3.

Scheme 3:

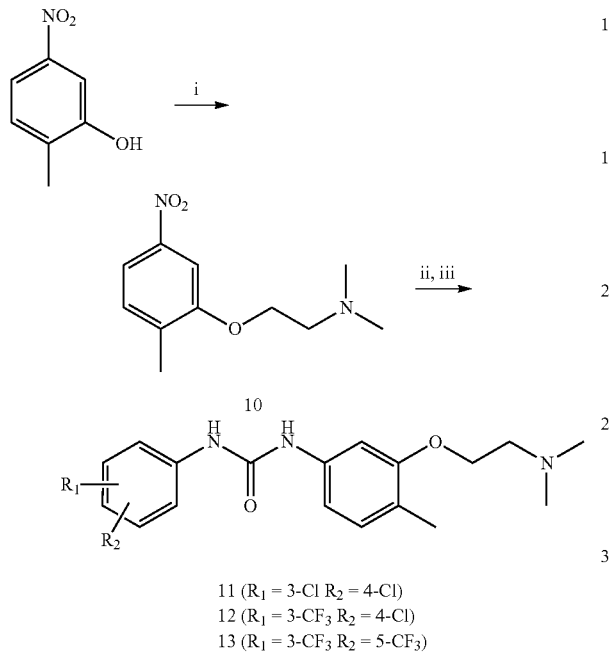

11 (R₁ = 3-Cl R₂ = 4-Cl)
12 (R₁ = 3-CF₃ R₂ = 4-Cl)
13 (R₁ = 3-CF₃ R₂ = 5-CF₃)

Reagents and conditions: (i) N,N-dimethylethanolamine, PPh₃, DEAD, THF, 0° C.; (ii) SnCl₂, EtOH, 90° C.; (iii) phenylisocyanates, dioxane, 55° C.

In the same way, compound 14, which was the precursor of N,N'-diarylureas 15-17 was obtained starting from 4-(2-hydroxymethyl)morpholine according to Scheme 4.

Scheme 4:

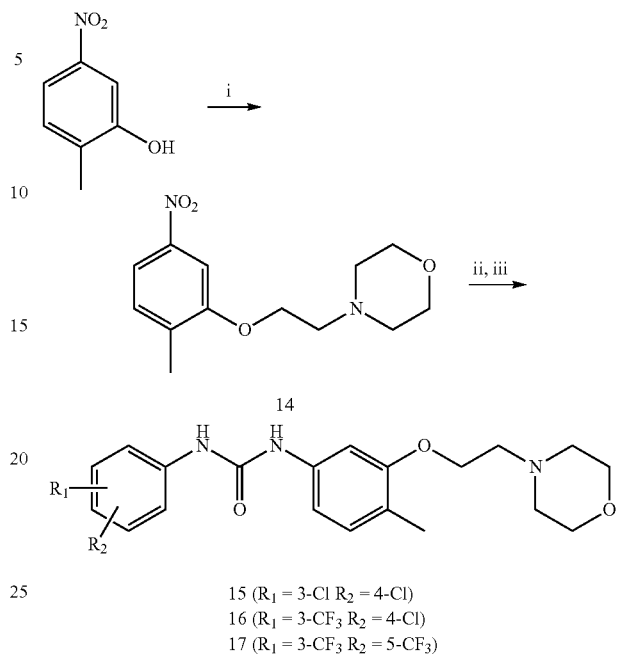

15 (R₁ = 3-Cl R₂ = 4-Cl)
16 (R₁ = 3-CF₃ R₂ = 4-Cl)
17 (R₁ = 3-CF₃ R₂ = 5-CF₃)

Reagents and conditions: (i) 4-(2-hydroxyethyl)morpholine, PPh₃, DEAD, THF, 0° C.; (ii) SnCl₂, EtOH, 90° C.; (iii) phenylisocyanates, dioxane, 55° C.

After reduction of the nitro group in amine by the use of tin chloride in ethanol at 90° C., the substituted anilines were directly coupled to the same various isocyanates in 1,4-dioxane at 55° C. overnight to produce 11-13 and 15-17.

In order to couple piperazine with 2-methyl-5-nitrophenol via a Mitsunobu reaction (compound 19), the secondary amine was first protected by a benzyloxycarbonyl group. The protection was carried out with benzylchloroformate and a solution of NaOH 4N to afford 18 according to Scheme 5.

Scheme 5:

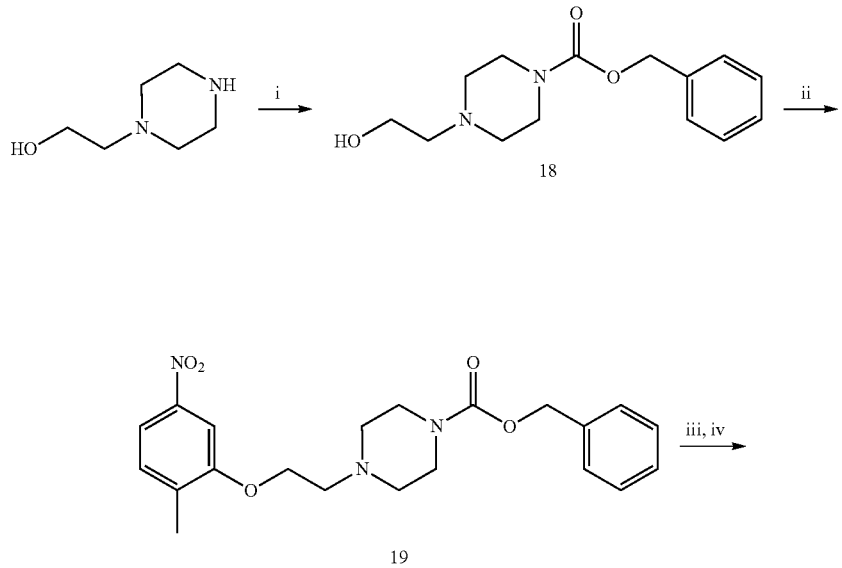

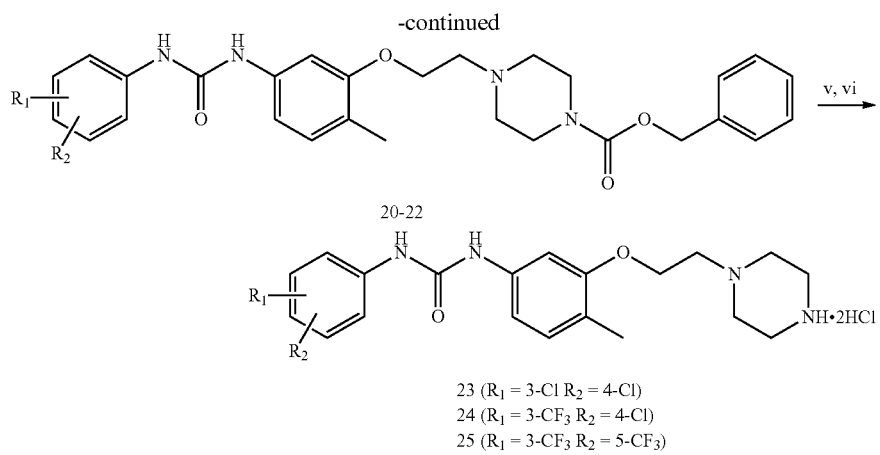

23 (R₁ = 3-Cl R₂ = 4-Cl)
24 (R₁ = 3-CF₃ R₂ = 4-Cl)
25 (R₁ = 3-CF₃ R₂ = 5-CF₃)

Reagents and conditions: (i) benzylchloroformate, NaOH 4N, CH₃CN/H₂O; (ii) 2-methyl-5-nitrophenol, PPh₃, DEAD, THF, 0° C.; (iii) SnCl₂, EtOH, 90° C.; (iv) phenylisocyanates, dioxane, 55° C.; (v) H₂, Pd—C, MeOH, 1 atm; (vi) HCl 4N, dioxane.

After the coupling reaction using triphenylphosphine and DEAD in THF, the nitro group was, as previously described, reduced in amine and coupled to the same various isocyanates to produce protected intermediates 20-22. Finally, after a hydrogenolysis carried out at atmospheric pressure under hydrogen and in presence of palladium on carbon, a precipitation in a solution of HCl 4N in 1,4-dioxane allowed the isolation of N,N'-diarylureas 23-25 as salts.

The last series of molecules in this example, in which heteroatoms were included in the aromatic ring, was prepared starting from several substituted pyridine and pyrimidine and using the same general procedure in 1,4-dioxane at 55° C. overnight according to Scheme 6.

Scheme 6:

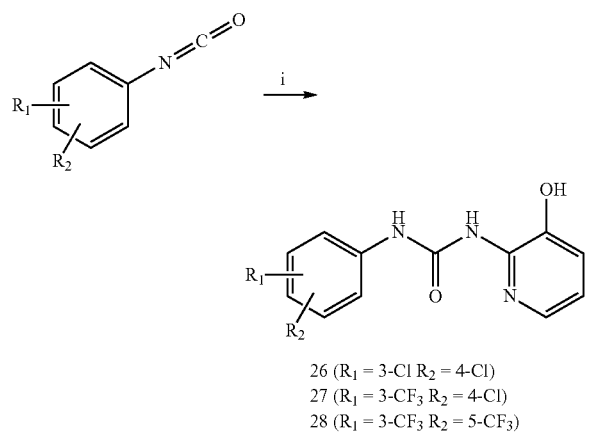

26 (R₁ = 3-Cl R₂ = 4-Cl)
27 (R₁ = 3-CF₃ R₂ = 4-Cl)
28 (R₁ = 3-CF₃ R₂ = 5-CF₃)

Reagents and conditions: (i) 2-amino-3-hydroxypyridine, dioxane 55° C.

While compounds 26 and 27 appeared to be easily isolable by crystallization or purification by preparative HPLC, compound 28, which was derived from 2-amino-4-hydroxy-6-methylpyrimidine, appeared to be not soluble in any solvent. Because it could not be purified, this compound was removed from the structure-activity relationship (SAR) study.

General Procedure A for the Synthesis of Compounds 1-9

1,3-bis(3,4-dichlorophenyl)urea (Compound 1)

As a non-limiting example, 3,4-dichlorophenylisocyanate (188 mg, 1 mmol) and 3,4-dichloroaniline (178 mg, 1.1 mmol) were dissolved in 10 mL of anhydrous dioxane. The reaction mixture was warmed to 55° C., stirred under nitrogen over night and then cooled to room temperature. The solvent was removed under vacuum and the crude was purified twice by crystallization in ethyl acetate/hexane to afford 1 (262 mg, 75%) as a white powder.

1,3-bis[4-chloro-3-(trifluoromethyl)phenyl]urea (Compound 2)

As another non-limiting example, 4-chloro-3(trifluoromethyl)phenylisocyanate (222 mg, 1 mmol) and 4-chloro-3-(trifluoromethyl)aniline (215 mg, 1.1 mmol) were used following the general procedure A to isolate 2 (250 mg, 60%) as a white powder.

1,3-bis[3,5-bis(trifluoromethyl)phenyl]urea (Compound 3)

As another non-limiting example, 3,5-bis(trifluoromethyl)phenylisocyanate (600 mg, 2.353 mmol) and 3,5-bis(trifluoromethyl)aniline (647 mg, 2.824 mmol) were used following the general procedure A to isolate 3 (1140 mg, 78%) as a white powder. $^1$H NMR (500 MHz, CD₃OD, δ): 8.12 (s, 1H, $CH_{arom.}$), 7.59 (s, 1H, $CH_{arom.}$). $^{13}$C NMR (400 MHz, CD₃OD, δ): 152.89, 141.32, 132.55, 131.80, 124.9, 122.2, 118.4, 115.24.

3-(3,4-dichlorophenyl)-1-(3-hydroxy-4-methylphenyl)urea (Compound 4)

As another non-limiting example, 3,4dichlorophenylisocyanate (202 mg, 1.073 mmol) and 5-aminocresol (120 mg, 0.976 mmol) were used following the general procedure A to isolate 4 (244 mg, 81%) as a white powder. $^1$H NMR (500 MHz, DMSO$_{d6}$, δ): 9.24 (s, 1H, OH), 8.82 (s, 1H, NH), 8.57

(s, 1H, NH), 7.85 (s, 1H, CH$_{arom.}$), 7.47 (d, J=11 Hz, 1H, CH$_{arom.}$), 7.28 (d, J=11 Hz, 1H, CH$_{arom.}$), 7.04 (s, 1H, CH$_{arom.}$), 6.90 (d, J=10 Hz, 1H, CH$_{arom.}$), 6.69 (d, J=10 Hz, 1H, CH$_{arom.}$), 2.02 (s, 3H, CH$_3$). $^{13}$C NMR (400 MHz, DMSO$_{d6}$, δ): 156.09, 152.84, 140.77, 138.45, 131.68, 131.19, 131.06, 123.54, 119.78, 118.84, 118.35, 109.71, 105.96, 16.09.

3-[4-chloro-3-(trifluoromethyl)phenyl]-1-(3-hydroxy-4-methylphenyl)urea (Compound 5)

As another non-limiting example, 4-chloro-3-(trifluoromethyl)phenylisocyanate (198 mg, 0.894 mmol) and 5-aminocresol (100 mg, 0.813 mmol) were used following the general procedure A to isolate 5 (102 mg, 46%) as a white powder. $^1$H NMR (500 MHz, DMSO$_{d6}$, δ): 9.26 (s, 1H, OH), 9.03 (s, 1H, NH), 8.64 (s, 1H, NH), 8.12 (s, 1H, CH$_{arom.}$), 7.58 (m, 2H, CH$_{arom.}$), 7.10 (s, 1H, CH$_{arom.}$), 6.92 (d, J=8 Hz, 1H, CH$_{arom.}$), 6.69 (d, J=8 Hz, 1H, CH$_{arom.}$), 2.04 (s, 3H, CH$_3$). $^{13}$C NMR (400 MHz, DMSO$_{d6}$, δ): 156.09, 125.93, 140.17, 138.38, 132.62, 131.05, 123.53, 122.72, 118.40, 109.79, 106.04, 16.07.

3-[3,5-bis(trifluoromethyl)phenyl]-1-(3-hydroxy-4-methylphenyl)urea (Compound 6)

As another non-limiting example, 3,5-bis(trifluoromethyl) phenylisocyanate (200 mg, 0.784 mmol) and 5-aminocresol (106 mg, 0.862 mmol) were used following the general procedure A to synthesize 9. At the end of the reaction, the crude was purified by flash chromatography (15 to 30% of ethyl acetate in cyclohexane). After concentration of the pure fractions, the white solid was crystallized in hexane to afford 6 (260 mg, 52.5%) as a white powder. $^1$H NMR (500 MHz, DMSO$_{d6}$, δ): 9.27 (s, 1H, OH), 9.25 (s, 1H, NH), 8.79 (s, 1H, NH), 8.11 (s, 2H, CH$_{arom.}$), 7.61 (s, 1H, CH$_{arom.}$), 7.12 (s, 1H, CH$_{arom.}$), 6.94 (d, J=8 Hz, 1H, CH$_{arom.}$), 6.72 (d, J=8 Hz, 1H, CH$_{arom.}$), 2.05 (s, 3H, CH$_3$). $^{13}$C NMR (500 MHz, DMSO$_{d6}$, δ): 156.11, 152.97, 142.26, 138.20, 131.48, 131.23, 130.97, 127.27, 125.10, 122.93, 118.76, 114.85, 110.05, 106.30, 16.09.

Compound 7

As another non-limiting example, 3,4-dichlorophenylisocyanate (151 mg, 0.803 mmol) and 3-methoxy-4-methylaniline (100 mg, 0.730 mmol) were used following the general procedure A to isolate 7 (204 mg, 86%) as a white powder. $^1$H NMR (500 MHz, DMSO$_{d6}$, δ): 8.91 (s, 1H, NH), 8.70 (s, 1H, NH), 7.88 (s, 1H, CH$_{arom.}$), 7.50 (d, J=9 Hz, 1H, CH$_{arom.}$), 7.30 (d, J=9 Hz, 1H, CH$_{arom.}$), 7.19 (s, 1H, CH$_{arom.}$), 7.01 (d, J=8 Hz, 1H, CH$_{arom.}$), 6.82 (d, J=8 Hz, 1H, CH$_{arom.}$), 3.76 (s, 3H, OCH$_3$), 2.07 (s, 3H, CH$_3$). $^{13}$C NMR (400 MHz, DMSO$_{d6}$, δ): 157.99, 152.97, 140.71, 139.02, 131.70, 131.22, 130.87, 123.67, 119.91, 119.84, 119.00, 110.72, 102.14, 55.72, 16.15.

Compound 8

As another non-limiting example, 4-chloro-3-(trifluoromethyl)phenylisocyanate (151 mg, 0.682 mmol) and 3-methoxy-4-methylaniline (85 mg, 0.620 mmol) were used following the general procedure A to isolate 8 (102 mg, 46%) as a white powder. 1H NMR (500 MHz, DMSO$_{d6}$, δ): 9.07 (s, 1H, NH), 8.74 (s, 1H, NH), 8.07 (s, 1H, CH arom.), 7.60 (m, 2H, CH arom.), 7.17 (s, 1H, CH arom.), 7.00 (d, J=10 Hz, 1H, CH arom.), 6.82 (d, J=10 Hz, 1H, CH arom.), 3.74 (s, 3H, OCH$_3$), 2.06 (s, 3H, CH$_3$). 13C NMR (400 MHz, DMSO$_{d6}$, δ): 157.99, 153.05, 140.10, 138.95, 132.64, 130.87, 123.70, 119.95, 117.39, 110.85, 102.22, 55.70, 16.14.

Compound 9

As another non-limiting example, 3,5-bis(trifluoromethyl)phenylisocyanate (143 mg, 0.562 mmol) and 3-methoxy-4-methylaniline (70 mg, 0.511 mmol) were used following the general procedure A to isolate 9 (92 mg, 46%) as a white powder. $^1$H NMR (500 MHz, DMSO$_{d6}$, δ): 9.32 (s, 1H, NH), 8.90 (s, 1H, NH), 8.10 (m, 2H, CH$_{arom.}$), 7.61 (s, 1H, CH$_{arom.}$), 7.18 (s, 1H, CH$_{arom.}$), 7.00 (d, J=10 Hz, 1H, CH$_{arom.}$), 6.85 (d, J=10 Hz, 1H, CH$_{arom.}$), 3.74 (s, 3H, OCH$_3$), 2.06 (s, 3H, CH$_3$). $^{13}$C NMR (400 MHz, DMSO$_{d6}$, δ): 157.98, 153.05, 142.59, 138.74, 131.50, 131.18, 130.86, 128.06, 125.35, 122.64, 120.16, 118.59, 114.92, 111.08, 102.42, 55.73, 16.15.

General Procedure B (for the Synthesis of Compounds 10, 14 and 19)

Compound 10

As another non-limiting example, 2-methyl-5-nitrophenol (2.00 g, 13.07 mmol), N,N-dimethylethanolamine (1.31 mL, 13.07 mmol) and triphenylphosphine (4.46 g, 16.99 mmol) were placed in a 100 mL round-bottomed flask under nitrogen. 40 mL of anhydrous THF were added via syringe at 0° C. After stirring the reaction mixture at this temperature for 10 minutes, 7.32 mL of a solution of diethylazodicarboxylate 40% in toluene (2.93 g, 16.99 mmol) were added via syringe. The reaction was warmed to room temperature and stirred under nitrogen for two hours. The solvents were removed under vacuum. Triphenylphosphine oxide formed during the reaction was precipitated in a mixture of ethyl acetate/hexane and filtrated. The crude was then purified by flash chromatography (0 to 2% of MeOH in DCM) to afford 10 (2.11 g, 70%) as a yellow oil.

General Procedure C (for the Synthesis of Compounds 11-13, 14-16 and 20-22)

3-(3,4-dichlorophenyl)-1-{3-[2-(dimethylamino) ethoxy]-4-methylphenyl}urea (Compound 11)

As another non-limiting example, Compound 10 (262 mg, 1.169 mmol) was dissolved in 10 mL of EtOH. SnCl$_2$H$_2$O (1316 mg, 5.848 mmol) was added and the temperature was increased to 90° C. The reaction mixture was stirred for 1.5 hours, cooled to room temperature and poured into iced water. The solution was made alkaline with solid NaOH and then extracted with DCM (3×30 mL). Organic extracts were combined, washed with water (60 mL) and brine (60 mL), dried over sodium sulfate, concentrated and finally dried under high vacuum over night to afford the substituted aniline (202 mg, 1.041 mmol) as a light-yellow oil. This compound was then dissolved in 10 mL of anhydrous dioxane and 3,4-dichlorophenylisocyanate (254 mg, 1.353 mmol) was added. The reaction mixture was warmed to 55° C., stirred under nitrogen overnight and then cooled to room temperature. The crude was purified by flash chromatography (0 to 2% of MeOH in DCM). After concentration of the pure fractions, the obtained white solid was crystallized in hexane to afford 11 (260 mg, 58%) as a white powder. $^1$H NMR (300 MHz, DMSO$_{d6}$, δ): 8.92 (s, 1H, NH), 8.69 (s, 1H, NH), 7.85 (s, 1H, CH$_{arom.}$), 7.45 (d, J=8.7 Hz, 1H, CH$_{arom.}$), 7.27 (d, J=8.7 Hz, 1H, CH$_{arom.}$), 7.15 (m, 1H, CH$_{arom.}$), 6.98 (d, J=7.8 Hz, 1H, CH$_{arom.}$), 6.80 (d, J=7.8 Hz, 1H, CH$_{arom.}$), 3.98 (t, J=5.7 Hz, 2H, OCH$_2$), 2.63 (t, J=5.7 Hz, 2H, CH$_2$N), 2.21 (s, 6H, N(CH$_3$)$_2$), 2.04 (s, 3H, CH$_3$). $^{13}$C NMR (400 MHz, DMSO$_{d6}$, δ): 157.22, 152.97, 140.67, 138.88, 131.68, 131.19, 130.90, 123.66, 120.11, 119.89, 118.99, 110.88, 103.09, 66.72, 58.30, 46.30, 16.11.

3-[4-chloro-3-(trifluoromethyl)phenyl]-1-{3-[2-(dimethylamino)ethoxy]-4-methylphenyl}urea (Compound 12)

As another non-limiting example, Compound 10 (155 mg, 0.692 mmol) and 4-chloro-3-(trifluoromethyl) phenyl isocyanate (151 mg, 0.682 mmol) were used following the general procedure B to synthesize 12. At the end of the reaction, the mixture was precipitated in a solution of HCl 4N in dioxane. After filtration, the white solid was dissolved in acetic acid and purified by preparative HPLC (10 to 40% of acetonitrile in water with 0.1% of acetic acid) to afford 12 (161 mg, 52%) as a white powder. $^1$H NMR (500 MHz, DMSO$_{d6}$, δ): 9.26 (s, 1H, NH), 8.86 (s, 1H, NH), 8.09 (s, 1H, CH$_{arom.}$), 7.62 (m, 2H, CH$_{arom.}$), 7.18 (s, 1H, CH$_{arom.}$), 7.15 (d, J=8 Hz, 1H, CH$_{arom.}$), 6.85 (d, J=8 Hz, 1H, CH$_{arom.}$), 4.02 (t, J=5.5 Hz, 2H, OCH$_2$), 2.71 (t, J=5.5 Hz, 2H, CH$_2$N), 2.27 (s, 6H, N(CH$_3$)$_2$), 2.08 (s, 3H, CH$_3$).

3-[3,5-bis(trifluoromethyl)phenyl]-1-{3-[2-(dimethylamino)ethoxy]-4-methylphenyl}urea (Compound 13)

As another non-limiting example, Compound 10 (248 mg, 1.107 mmol) and 3,5-bis(trifluoromethyl) phenylisocyanate (326 mg, 1.280 mmol) were used following the general procedure B to synthesize 13. At the end of the reaction, the crude was purified by flash chromatography (2 to 8% of MeOH in DCM). After concentration of the pure fractions, the white solid was crystallized in hexane to afford 13 (260 mg, 52.5%) as a white powder. $^1$H NMR (500 MHz, DMSO$_{d6}$, δ): 9.37 (s, 1H, NH), 8.90 (s, 1H, NH), 8.12 (s, 2H, CH$_{arom.}$), 7.62 (m, 1H, CH$_{arom.}$), 7.19 (s, 1H, CH$_{arom.}$), 7.03 (d, J=8 Hz, 1H, CH$_{arom.}$), 6.88 (d, J=8 Hz, 1H, CH$_{arom.}$), 4.03 (t, J=5.5 Hz, 2H, OCH$_2$), 2.68 (t, J=5.5 Hz, 2H, CH$_2$N), 2.25 (s, 6H, N(CH$_3$)$_2$), 2.09 (s, 3H, CH$_3$). $^{13}$C NMR (400 MHz, DMSO$_{d6}$, δ): 157.24, 153.05, 142.58, 138.61, 131.51, 131.19, 130.90, 127.78, 125.34, 122.62, 120.46, 118.53, 114.89, 111.26, 103.40, 66.77, 58.30, 46.28, 15.95.

Compound 14

As another non-limiting example, 2-methyl-5-nitrophenol (2.00 g, 13.07 mmol), 4(2-hydroxyethyl)morpholine (1.71 mg, 13.07 mmol), triphenylphosphine (4.46 g, 16.99 mmol) and 7.32 mL of a solution of diethylazodicarboxylate 40% in toluene (2.93 g, 16.99 mmol) were used following the general procedure B to synthesize 14. After treatments, the crude was purified by flash chromatography (0 to 3% of MeOH in DCM) to afford 14 (0.85 g, 23%) as a brown oil.

3-(3,4-dichlorophenyl)-1-{4-methyl-3-[2-(morpholin-4-yl)ethoxy]phenyl}urea (Compound 15)

As another non-limiting example, Compound 14 (278 mg, 1.045 mmol) and 3,4-dichlorophenylisocyanate (285 mg, 1.118 mmol) were used following the general procedure C to synthesize 14. At the end of the reaction, the crude was purified by flash chromatography in normal phase (10 to 0% of cyclohexane in ethyl acetate). After concentration of the pure fractions, the obtained white solid was crystallized in hexane to afford 15 (217 mg, 49%) as a white powder. $^1$H NMR (500 MHz, DMSO$_{d6}$, δ): 8.94 (s, 1H, NH), 8.70 (s, 1H, NH), 7.89 (s, 1H, CH$_{arom.}$), 7.51 (d, J=8.5 Hz, 1H, CH$_{arom.}$), 7.32 (d, J=8.5 Hz, 1H, CH$_{arom.}$), 7.20 (s, 1H, CH$_{arom.}$), 7.02, (d, J=8 Hz, 1H, CH$_{arom.}$), 6.81 (d, J=8 Hz, 1H, CH$_{arom.}$), 4.05 (t, J=5.5 Hz, 2H, OCH$_2$), 3.58 (m, 4H, CH$_2$OCH$_2$), 2.73 (t, J=5.5 Hz, 2H, CH$_2$N), 2.50 (m, 4H, N(CH$_2$)$_2$), 2.08 (s, 3H, CH$_3$). $^{13}$C NMR (400 MHz, DMSO$_{d6}$, δ): 157.19, 152.96, 140.66, 138.88, 131.68, 131.19, 130.91, 123.67, 120.15, 119.89, 118.98, 110.95, 103.22, 66.87, 66.46, 57.62, 54.62, 15.98.

3-[4-chloro-3-(trifluoromethyl)phenyl]-1-{4-methyl-3-[2-(morpholin-4-yl)ethoxy]phenyl}urea (Compound 16)

As another non-limiting example, Compound 14 (267 mg, 1.004 mmol) and 4-chloro-3-(trifluoromethyl) phenylisocyanate (241 mg, 1.091 mmol) were used following the general procedure C to synthesize 16. At the end of the reaction, the crude was purified by flash chromatography (10 to 0% of cyclohexane in ethyl acetate). After concentration of the pure fractions, the obtained white solid was crystallized in hexane to afford 16 (263 mg, 58%) as a white powder. $^1$H NMR (500 MHz, DMSO$_{d6}$, δ): 9.11 (s, 1H, NH), 8.74 (s, 1H, NH), 8.09 (s, 1H, CH$_{arom.}$), 7.61 (m, 2H, CH$_{arom.}$), 7.20 (s, 1H, CH$_{arom.}$), 7.02 (d, J=8 Hz, 1H, CH$_{arom.}$), 6.83 (d, J=8 Hz, 1H, CH$_{arom.}$), 4.05 (t, J=5.5 Hz, 2H, OCH$_2$), 3.58 (m, 4H, CH$_2$OCH$_2$), 2.73 (t, J=5.5 Hz, 2H, CH$_2$N), 2.50 (m, 4H, N(CH$_2$)$_2$), 2.08 (s, 3H, CH$_3$). $^{13}$C NMR (400 MHz, DMSO$_{d6}$, δ): 157.23, 153.07, 140.11, 138.85, 1321.65, 130.92, 123.71, 120.27, 117.35, 110.12, 103.40, 66.77, 66.37, 57.65, 54.28, 15.98.

3-[3,5-bis(trifluoromethyl)phenyl]-1-{4-methyl-3-[2-(morpholin-4-yl)ethoxy]phenyl}urea (Compound 17)

As another non-limiting example, Compound 14 (273 mg, 1.026 mmol) and 3,5-bis(trifluoromethyl) phenylisocyanate (285 mg, 1.118 mmol) were used following the general procedure C to synthesize 17. At the end of the reaction, the crude was purified by flash chromatography in normal phase (20 to 10% of cyclohexane in ethyl acetate). After concentration of the pure fractions, the obtained white solid was crystallized in hexane to afford 17 (235 mg, 48%) as a white powder. $^1$H NMR (500 MHz, DMSO$_{d6}$, δ): 10.11 (s, 1H, NH), 9.34 (s, 1H, NH), 8.11 (s, 2H, CH$_{arom.}$), 7.60 (s, 1H, CH$_{arom.}$), 7.22, (s, 1H, CH$_{arom.}$), 7.02 (d, J=7.5 Hz, 1H, CH$_{arom.}$), 6.85 (d, J=7.5 Hz, 1H, CH$_{arom.}$), 4.05 (m, 2H, OCH$_2$), 3.58 (m, 4H, CH$_2$OCH$_2$), 2.73 (m, 2H, CH$_2$N), 2.51 (m, 4H, N(CH$_2$)$_2$), 2.08 (s, 3H, CH$_3$).

Compound 18

As another non-limiting example, piperazine (3.00 g, 23.04 mmol) was dissolved in 15 mL of water in a three-neck round-bottomed flask. A solution of benzylchloroformate (3.95 mL, 27.65 mmol) in 15 mL of acetonitrile was added drop wise via isobar cylindrical funnel. In order to maintain the pH around 9, a solution of NaOH 4N was added drop wise via a second isobar cylindrical funnel. The reaction mixture was stirred over night at room temperature and then extracted with DCM (2×75 mL). The aqueous phase containing the final compound was acidified with HCl 3N and extracted with DCM (3×75 mL). Organic extracts were combined, washed with brine (150 mL), dried over sodium sulfate and concentrated under vacuum. The crude was purified by flash chromatography (0 to 2% of MeOH in DCM) to afford 18 (5.41 g, 90%) as a colorless oil.

Compound 19:

As another non-limiting example, 2-methyl-5-nitrophenol (1.70 g, 11.11 mmol), compound 18 (2.94 mg, 11.1 mmol), triphenylphosphine (3.79 g, 14.44 mmol) and 6.27 mL of a solution of diethylazodicarboxylate 40% in toluene (2.51 g, 14.44 mmol) were used following the general procedure B to synthesize 19. After treatments, the crude was then purified by flash chromatography (0 to 3% of MeOH in DCM) to afford 19 (3.82 g, 86%) as a yellow oil.

Compound 20

As another non-limiting example, Compound 19 (1.172 g, 2.937 mmol) and 3,4-dichlorophenylisocyanate (0.545 g, 2.778 mmol) were used following the general procedure C to synthesize 20. After treatments, the crude was purified by flash chromatography (40 to 0% of cyclohexane in ethyl acetate) to afford 20 (0.984 g, 60%) as a white powder.

Compound 21

As another non-limiting example, Compound 19 (1.042 g, 2.609 mmol) and 4-chloro-3-(trifluoromethyl) phenylisocyanate (0.545 g, 2.459 mmol) were used following the general procedure C to synthesize 21. After treatments, the crude was purified by flash chromatography (40 to 0% of cyclohexane in ethyl acetate) to afford 21 (1.045 g, 68%) as a white powder.

Compound 22

As another non-limiting example, Compound 19 (992 mg, 2.486 mmol) and 3,5-bis(trifluoromethyl) phenylisocyanate (600 mg, 2.352 mmol) were used following the general procedure C to synthesize 22. After treatments, the crude was purified by flash chromatography (5 to 0% of cyclohexane in ethyl acetate) to afford 22 (945 mg, 71%) as a white powder.

General Procedure D (for the Synthesis of Compounds 23-25)

4-[2-(5-{[(3,4-dichlorophenyl)carbamoyl]amino}-2-methylphenoxy)ethyl]piperazine-1,4-diium dichloride (Compound 23)

As another non-limiting example, Compound 20 (870 mg, 1.561 mmol) was dissolved in 20 mL of MeOH and Pd—C (10% by weight, 93 mg) was carefully added. The reaction mixture was stirred under a flux of hydrogen for 2 hours at atmospheric pressure and room temperature (the reaction was monitored by LCMS) and then filtered through a pad of celite. The filtrate was concentrated and purified by HPLC (10 to 45% of acetonitrile in water with 0.1% of acetic acid). After concentration of the pure fractions, the compound was precipitated in a solution of HCl 4N in dioxane to afford 23 (379 mg, 49%) as a white powder. $^1$H NMR (500 MHz, DMSO$_{d6}$, δ): 12.03 (s, 1H, NH), 9.77 (s, 1H, NH), 9.57 (m, 2H, NH), 9.36 (s, 1H, NH), 7.89 (s, 1H, CH$_{arom.}$), 7.50 (d, J=8.5 Hz, 1H, CH$_{arom.}$), 7.32 (m, 2H, CH$_{arom.}$), 7.05 (d, J=8 Hz, 1H, CH$_{arom.}$), 6.83 (d, J=8 Hz, 1H, CH$_{arom.}$), 4.33 (m, 2H, OCH$_2$), 3.74-3.39 (m, 10H, CH$_2$N), 2.13 (s, 3H, CH$_3$).

4-{2-[5-({[4-chloro-3-(trifluoromethyl)phenyl] carbamoyl}amino)-2-ethylphenoxy] ethyl}piperazine-1,4-diium dichloride (Compound 24)

As another non-limiting example, Compound 21 (930 mg, 1.573 mmol) was treated following the general procedure D and purified by HPLC (15 to 45% of acetonitrile in water with 0.1% of acetic acid). After concentration of the pure fractions, the compound was precipitated in a solution of HCl 4N in dioxane to afford 24 (600 mg, 72%) as a white powder. $^1$H NMR (500 MHz, DMSO$_{d6}$, δ): 12.00 (s, 1H, NH), 9.94 (s, 1H, NH), 9.61 (m, 2H, NH), 9.40 (s, 1H, NH), 8.11 (s, 1H, CH$_{arom.}$), 7.61 (m, 2H, CH$_{arom.}$), 7.29 (s, 1H, CH$_{arom.}$), 7.06 (d, J=8 Hz, 1H, CH$_{arom.}$), 6.85 (d, J=8 Hz, 1H, CH$_{arom.}$), 4.37 (m, 2H, OCH$_2$), 3.85-3.46 (m, 10H, CH$_2$N), 2.13 (s, 3H, CH$_3$).

4-{2-[5-({[3,5-bis(trifluoromethyl)phenyl] carbamoyl}amino)-2-methylphenoxy] ethyl}piperazine-1,4-diium dichloride (Compound 25)

As another non-limiting example, Compound 22 (840 mg, 1.345 mmol) was treated following the general procedure D and purified by HPLC (15 to 45% of acetonitrile in water with 0.1% of acetic acid). After concentration of the pure fractions, the compound was precipitated in a solution of HCl 4N in dioxane to afford 25 (318 mg, 42%) as a white powder. $^1$H NMR (500 MHz, DMSO$_{d6}$, δ): 12.13 (s, 1H, NH), 10.45 (s, 1H, NH), 9.71 (m, 2H, NH), 9.58 (s, 1H, NH), 8.10 (s, 2H, CH$_{arom.}$), 7.61 (m, 12H, CH$_{arom.}$), 7.29 (s, 1H, CH$_{arom.}$), 7.07 (d, J=8 Hz, 1H, CH$_{arom.}$), 6.87 (d, J=8 Hz, 1H, CH$_{arom.}$), 4.37 (m, 2H, OCH$_2$), 3.77-3.40 (m, 10H, CH$_2$N), 2.14 (s, 3H, CH$_3$).

General Procedure E (for the Synthesis of Compounds 26-28)

Compound 26

As another non-limiting example, 3,4-dichlorophenylisocyanate (250 mg, 1.330 mmol) and 2-amino-3-hydroxypyridine (146 mg, 1.330 mmol) were dissolved in 10 mL of anhydrous dioxane. The reaction mixture was warmed to 55° C., stirred under nitrogen over night and then cooled to room temperature. The crude was purified twice by crystallization in EtOH to afford 26 (178 mg, 45%) as a white powder.

Compound 27

As another non-limiting example, 3,4-dichlorophenylisocyanate (250 mg, 1.330 mmol) and 4-amino-6-methoxypyrimidine (166 mg, 1.330 mmol) were used following the general procedure E to synthesize 27. At the end of the reaction, the crude was dissolved in acetic acid and purified by HPLC (70 to 100% of acetonitrile in water) to afford 27 (224 mg, 54%) as a white powder.

Compound 28

As another non-limiting example, 3,4-dichlorophenylisocyanate (250 mg, 1.330 mmol) and 2-amino-4-hydroxy-6-methylpyrimidine (166 mg, 1.330 mmol) were used following the general procedure E to synthesize 28. Unfortunately, at the end of the reaction the crude wasn't purified as it wasn't soluble in any solvent tested.

TABLE 2

ATF-4 assays in CRL-2351 cell line.

| | Structure | ATF-4 $A_{max}{}^a$ | $C_{max}$ (μM)$^b$ | $C_{[5]}$ (μM)$^c$ |
|---|---|---|---|---|
| 1 | 3,4-Cl₂-C₆H₃-NH-C(O)-NH-C₆H₃-3,4-Cl₂ | 11 | 5 | 2 |
| 2 | 3-CF₃-4-Cl-C₆H₃-NH-C(O)-NH-C₆H₃-3-CF₃-4-Cl | 11 | 2.4 | 1.5 |
| 3 | 3,5-(CF₃)₂-C₆H₃-NH-C(O)-NH-C₆H₃-3,5-(CF₃)₂ | 11 | 2.5 | 1.5 |
| 4 | 3,4-Cl₂-C₆H₃-NH-C(O)-NH-C₆H₃(3-OH, 4-Me) | 13 | 20 | 11 |
| 5 | 3-CF₃-4-Cl-C₆H₃-NH-C(O)-NH-C₆H₃(3-OH, 4-Me) | 11 | 10 | 6 |
| 6 | 3,5-(CF₃)₂-C₆H₃-NH-C(O)-NH-C₆H₃(3-OH, 4-Me) | 13 | 5 | 3 |
| 7 | 3,4-Cl₂-C₆H₃-NH-C(O)-NH-C₆H₃(3-OMe, 4-Me) | NA | NA | NA |
| 8 | 3-CF₃-4-Cl-C₆H₃-NH-C(O)-NH-C₆H₃(3-OMe, 4-Me) | 8 | 10 | 3 |
| 9 | 3,5-(CF₃)₂-C₆H₃-NH-C(O)-NH-C₆H₃(3-OMe, 4-Me) | 12 | 20 | <2.5 |
| 11 | 3,4-Cl₂-C₆H₃-NH-C(O)-NH-C₆H₃(3-OCH₂CH₂NMe₂, 4-Me) | 7.5 | 20 | 8 |

TABLE 2-continued

ATF-4 assays in CRL-2351 cell line.

| | Structure | ATF-4 | | |
|---|---|---|---|---|
| | | $A_{max}{}^{a}$ | $C_{max}$ ($\mu M$)$^{b}$ | $C_{[5]}$ ($\mu M$)$^{c}$ |
| 12 | F₃C–⟨⟩–Cl, NH-C(O)-NH–⟨⟩–O–CH₂CH₂–N(CH₃)₂, with CH₃ on ring | 7 | 10 | 7 |
| 13 | 3,5-(CF₃)₂–C₆H₃–NH-C(O)-NH–⟨⟩–O–CH₂CH₂–N(CH₃)₂, with CH₃ | 12.5 | 10 | 5 |
| 15 | 3,4-Cl₂–C₆H₃–NH-C(O)-NH–⟨⟩–O–CH₂CH₂–morpholine, with CH₃ | 5.5 | 10 | 9 |
| 16 | F₃C/Cl–C₆H₃–NH-C(O)-NH–⟨⟩–O–CH₂CH₂–morpholine, with CH₃ | 7 | 10 | 7 |
| 17 | 3,5-(CF₃)₂–C₆H₃–NH-C(O)-NH–⟨⟩–O–CH₂CH₂–morpholine, with CH₃ | 9 | 10 | 3 |
| 23 | 3,4-Cl₂–C₆H₃–NH-C(O)-NH–⟨⟩–O–CH₂CH₂–piperazine-NH, with CH₃; 2HCl | 7.5 | 10 | 7 |
| 24 | F₃C/Cl–C₆H₃–NH-C(O)-NH–⟨⟩–O–CH₂CH₂–piperazine-NH, with CH₃; 2HCl | 6 | 10 | 7 |
| 25 | 3,5-(CF₃)₂–C₆H₃–NH-C(O)-NH–⟨⟩–O–CH₂CH₂–piperazine-NH, with CH₃; 2HCl | 10 | 10 | 6 |
| 26 | 3,4-Cl₂–C₆H₃–NH-C(O)-NH–(3-hydroxypyridin-2-yl) | 12 | 40 | 13 |

TABLE 2-continued

ATF-4 assays in CRL-2351 cell line.

| | Structure | $A_{max}{}^a$ | $C_{max}$ ($\mu M$)$^b$ | $C_{[5]}$ ($\mu M$)$^c$ |
|---|---|---|---|---|
| 27 | F₃C-, Cl- phenyl-NH-C(=O)-NH-pyridine-OH | 6.5 | 40 | 10 |
| 28 | F₃C-, CF₃- phenyl-NH-C(=O)-NH-pyridine-OH | 5 | 40 | 40 |

$^a$Maximal activity corresponding to the ration of firefly over renilla luceferase expression.
$^b$Concentration (in $\mu M$) corresponding to the maximal activity.
$^c$Concentration (in $\mu M$) corresponding to an activity threshold of 5.

TABLE 3

Determination of the IC$_{50}$ ($\mu M$) of the compounds by SRB assay.

| Compound | IC$_{50}$ ($\mu M$) | | |
|---|---|---|---|
| | 2351 | 2813 | KLN |
| 1 | 2.6 | 0.8 | >20 |
| 2 | 2.8 | 1.7 | ND |
| 3 | 0.6 | 0.1 | 3.9 |
| 4 | 9 | 1.8 | >20 |
| 5 | 9.3 | 1.6 | 20 |
| 6 | 3.2 | 1 | 13.5 |
| 7 | 11 | >20 | >20 |
| 8 | 2.5 | 3 | 17.2 |
| 9 | 2.2 | 0.7 | 20 |
| 11 | 5.8 | 5.3 | 13.5 |
| 12 | 2.5 | 2.8 | 12.3 |
| 13 | 2.9 | ND | 12.4 |
| 15 | 2.4 | ND | 20 |
| 16 | 2.7 | 0.9 | >20 |
| 17 | 2.3 | 0.8 | 18.6 |
| 23 | 4.5 | 5.1 | >20 |
| 24 | 2 | 3.5 | >20 |
| 25 | 5.2 | 3.1 | ND |
| 26 | 2 | 1.8 | >20 |
| 27 | 1.2 | 0.8 | 12.5 |
| 28 | 0.7 | 0.7 | 15 |

TABLE 4

In vitro Structure Activity Relationship of N,N'-Diarylthioureas.

| Structure | Code | Ternary Complex* 10 $\mu m$ | Ternary Complex* 3 $\mu m$ | Growth Inhibition IC$_{50}$** ($\mu m$) |
|---|---|---|---|---|
| 3,4-Cl₂-C₆H₃-NH-C(=S)-NH-C₆H₃-3,4-Cl₂ | 1806 | 3.5 | 2.5 | 0.9 |

TABLE 4-continued

In vitro Structure Activity Relationship of N,N'-Diarylthioureas.

| Structure | Code | Ternary Complex* 10 μm | Ternary Complex* 3 μm | Growth Inhibition IC$_{50}$** (μm) |
|---|---|---|---|---|
| 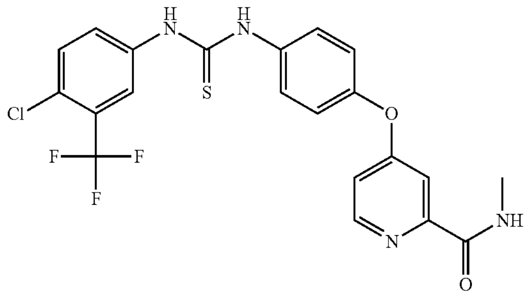 [SMILES: CNC(=O)c1cc(Oc2ccc(NC(=S)Nc3ccc(Cl)c(C(F)(F)F)c3)cc2)ccn1] | 1814 | 2 | 1.5 | 2 |
| 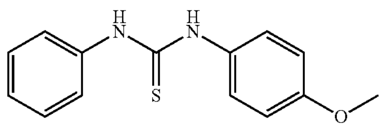 [SMILES: COc1ccc(NC(=S)Nc2ccccc2)cc1] | 1815 | 1 | 1 | >20 |
| 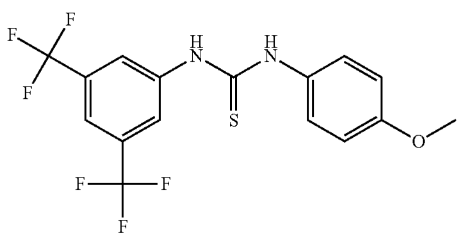 [SMILES: COc1ccc(NC(=S)Nc2cc(C(F)(F)F)cc(C(F)(F)F)c2)cc1] | 1816 | 2.5 | 1 | 1.5 |
| | 1817 | 6 | 1 | 1.4 |
| | 1817 | 7 | 1 | 1.4 |
| 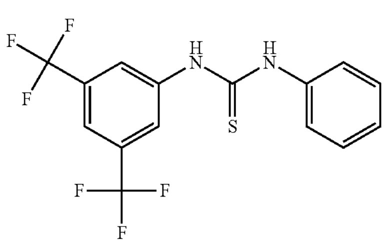 [SMILES: FC(F)(F)c1cc(NC(=S)Nc2ccccc2)cc(C(F)(F)F)c1] | 1819 | 6 | 1 | 1.5 |

TABLE 4-continued

In vitro Structure Activity Relationship of N,N'-Diarylthioureas.

| Structure | Code | Ternary Complex* 10 μm | Ternary Complex* 3 μm | Growth Inhibition IC$_{50}$** (μm) |
|---|---|---|---|---|
| (3,4-dihydroxyphenyl)-(4-chloro-3-trifluoromethylphenyl)thiourea | 1802 | 7 | 1.5 | 3.5 |
| bis(3,5-bis(trifluoromethyl)phenyl)triazole amine | 1836 | 1 | 1 | 2 |
| (3-hydroxy-4-methylphenyl)-(3,5-bis(trifluoromethyl)phenyl)thiourea | 1803 | 12 | 1 | 1.7 |
| (3,4-dichlorophenyl)-(3,4-dichlorophenyl)triazole amine | 1842 | 1 | 1 | NA |
| bis(4-chloro-3-trifluoromethylphenyl)thiourea | 1778 | 8 | 5 | 0.4 |
| (4-trifluoromethylphenyl)-(3,4-dichlorophenyl)thiourea | 1797 | 1 | 1 | 1.2 |

TABLE 4-continued

In vitro Structure Activity Relationship of N,N'-Diarylthioureas.

| Structure | Code | Ternary Complex* 10 μm | Ternary Complex* 3 μm | Growth Inhibition IC$_{50}$** (μm) |
|---|---|---|---|---|
| 3,5-bis(CF$_3$)phenyl-NH-C(=S)-NH-3,4-dichlorophenyl | 1798 | 5 | 3 | 0.4 |
| 3,5-bis(CF$_3$)phenyl-NH-C(=S)-NH-2-isopropylphenyl | 1820 | 11 | 1.5 | 1.5 |
| 3,5-bis(CF$_3$)phenyl-NH-C(=S)-NH-2-tert-butylphenyl | 1821 | 1 | 1 | 4 |
| phenyl-NH-C(=S)-NH-phenyl | 1831 | 1.8 | 1 | NA |
| 3,4-dichlorophenyl-NH-C(=S)-NH-4-chlorophenyl | 1805 | 8 | 1.4 | 1.6 |

TABLE 4-continued

In vitro Structure Activity Relationship of N,N'-Diarylthioureas.

| Structure | Code | Ternary Complex* 10 μm | Ternary Complex* 3 μm | Growth Inhibition IC$_{50}$** (μm) |
|---|---|---|---|---|
| 3,4-diCl-C6H3-NH-C(=S)-NH-C6H3-3,5-(CF3)2 | 1799 | 4 | 4 | 0.7 |
| 4-Cl-C6H4-NH-C(=S)-NH-C6H3-3,5-(CF3)2 | 1800 | 4 | 3 | 0.5 |
| 4-Cl-C6H4-NH-C(=S)-NH-C6H3-3,4-(CF3)(Cl) | 1801 | 3 | 3 | 0.8 |
| 3,5-(CF3)2-C6H3-NH-C(=S)-NH-C6H3-3,5-(CF3)2 | 1804 | 25 | 6 | 0.1 |

NA: Not active;
*Fold over basal;
**Concentration of compound that inhibits proliferation of CRL-2351 human breast cancer cells by 50%.

TABLE 5

| NSC #* | CAS_RN* | Activity 10 uM | Activity 5 uM | Activity 2.5 uM |
|---|---|---|---|---|
| 495 | 3056-73-3 | 3.74 | | 2.32 |
| 774 | 5394-77-4 | 22.38 | | 10.06 |
| 864 | 959-36-4 | 3.57 | | 1.81 |
| 1337 | 4567-99-1 | | | 7.15 |
| 1626 | 5346-51-0 | 5.31 | | 0.79 |
| 1874 | 613-63-8 | 3.99 | | 4.27 |
| 8275 | 22303-26-0 | | | 0.81 |
| 11235 | 2390-54-7 | 9.2 | | 4.88 |
| 12134 | | | | 8.83 |
| 12695 | 5410-88-8 | | | 6.31 |
| 12741 | 5425-32-1 | | | 8.35 |
| 12750 | 5450-50-0 | 4.9 | | 1.79 |
| 13268 | 5423-92-7 | 3.18 | | 1.46 |
| 14209 | 5429-71-0 | 14.32 | | 0.85 |
| 14238 | 5429-90-3 | 3.02 | | 1.37 |
| 14739 | | 4.06 | | 1.12 |
| 14755 | | 6.63 | | 0.68 |
| 19143 | 5444-68-8 | 3.2 | | 1.72 |
| 19763 | 6957-97-7 | 13.29 | | 4.63 |
| 21293 | | | | 3.16 |
| 21533 | 5436-20-4 | 8.88 | | 2.03 |
| 21620 | 2152-70-7 | 16.28 | | 0.74 |
| 24794 | | 3.37 | | 0.55 |
| 24863 | 2083-09-2 | 3.22 | | 1.87 |
| 26101 | 7770-76-5 | 4.13 | | 0.78 |
| 26672 | 7375-42-0 | 57.61 | | 1.44 |
| 26847 | | 8.15 | | 1.83 |
| 29215 | 68-76-8 | | | 36.4 |
| 30759 | | 6.9 | | 0.88 |
| 32929 | 5636-91-9 | 5.76 | | 0.35 |
| 32994 | 7511-84-4 | 6.52 | | 2.83 |

TABLE 5-continued

| NSC #* | CAS_RN* | Activity 10 uM | Activity 5 uM | Activity 2.5 uM |
|---|---|---|---|---|
| 32999 | | 6.87 | | 2.41 |
| 35424 | | 3.07 | | 2.55 |
| 35730 | | 6.76 | | 5.35 |
| 36684 | 6267-09-0 | 4.2 | | 0.76 |
| 38062 | 6337-31-1 | 5.58 | | 2.61 |
| 39901 | | 4.1 | | 1.41 |
| 42108 | 6935-42-8 | 3.7 | | |
| 42112 | 135-64-8 | 3.76 | | 3.76 |
| 43683 | 550-15-2 | 5.26 | | 3.73 |
| 45171 | 6300-60-3 | | | 3.08 |
| 45226 | 2691-81-8 | 7.27 | | 3.03 |
| 45884 | 27031-73-8 | 16.23 | | 0.47 |
| 47145 | 6330-21-8 | 5.16 | | 3.4 |
| 49546 | | 4.62 | | 3 |
| 50915 | 39077-64-0 | 7.81 | | 1.11 |
| 51522 | | 10.99 | | 1.66 |
| 52531 | 7355-32-0 | 5.18 | | 0.8 |
| 65429 | 6827-10-7 | | | 3.49 |
| 66326 | 14354-56-4 | 5.2 | | |
| 66379 | 2083-55-8 | 7.36 | | 0.74 |
| 68751 | | | | 4.46 |
| 76068 | 900-95-8 | 3.68 | | 1.02 |
| 78577 | | 3.56 | | 0.74 |
| 83335 | 3743-99-5 | 3.31 | | 2.77 |
| 86489 | 1027-40-3 | 3.17 | | 2.73 |
| 86537 | | 7.51 | | 3.85 |
| 87240 | 7375-42-0 | 37.28 | | 1.45 |
| 87695 | 16208-00-7 | 4.42 | | 3.28 |
| 88655 | 19320-23-1 | 18.32 | | 0.7 |
| 89160 | | | | 9.22 |
| 90299 | 22397-40-6 | 3.21 | | 2.1 |
| 90467 | | 3.88 | | 2.6 |
| 91815 | 20329-54-8 | 15.17 | | 3.3 |
| 91816 | 20329-55-9 | 29.75 | | 17.64 |
| 92938 | 7600-14-8 | 4.68 | | 3.41 |
| 95832 | | 3.2 | | 0.46 |
| 96942 | 2562-90-5 | 7.54 | | 4.17 |
| 97372 | 29676-50-4 | 4.98 | | 1.62 |
| 97681 | 88893-89-4 | 8.98 | | 1.17 |
| 99639 | 17958-62-2 | 8.32 | | 0.7 |
| 100622 | | 3.12 | | 2.25 |
| 102003 | | 9.46 | | 0.42 |
| 102516 | 13266-07-4 | 3.4 | | |
| 103749 | 30117-68-1 | 5.25 | | 2.76 |
| 105326 | 92967-81-2 | | | 9.56 |
| 106291 | | 3.15 | | 2.7 |
| 106378 | | 3.69 | | 2.55 |
| 106656 | 35694-47-4 | 3.26 | | 1.89 |
| 107229 | | 3.14 | | 1.06 |
| 108310 | 20691-83-2 | 4.88 | | 3.62 |
| 109326 | 23159-13-9 | 17.89 | | 0.69 |
| 112921 | 61446-06-8 | 242.82 | | 97.42 |
| 113085 | 1630-53-1 | 5.05 | | 3.18 |
| 114995 | 20852-34-0 | 3.43 | | 2.69 |
| 118028 | 17154-51-7 | 4.1 | | |
| 119675 | | 8.78 | | 5.52 |
| 122844 | | 13.27 | | 1.77 |
| 122854 | 13864-38-5 | 3.2 | | |
| 124738 | | 3.7 | | 0.79 |
| 125369 | 6683-64-3 | 9.98 | | 1.08 |
| 125516 | | 13.57 | | 0.79 |
| 126650 | 77800-85-2 | 8.04 | | 0.64 |
| 128665 | 22242-98-4 | 3.18 | | 17.83 |
| 130140 | | 19.67 | | 0.74 |
| 130216 | 92295-16-4 | 4.77 | | 0.51 |
| 131237 | 27117-05-1 | 3.3 | | 0.87 |
| 131464 | 20958-78-5 | 3.99 | | 3.63 |
| 131584 | 18754-93-3 | 7.95 | | 0.89 |
| 131663 | 22242-87-1 | 8.18 | | 7 |
| 131747 | 21628-67-1 | 3.25 | | 2.54 |
| 134404 | | 12.72 | | 5.44 |
| 135155 | | 7.19 | | 0.94 |
| 135854 | 28558-65-8 | 5.75 | | 3.56 |
| 141112 | | 3.76 | | 0.98 |
| 141226 | | 3.5 | | 1.05 |
| | | 3.8 | | 1.02 |
| 142606 | | 34.1 | | 16.57 |
| 146184 | 2381-85-3 | | | 3.13 |
| 146216 | 21771-92-6 | 5.04 | | 2.73 |
| 146249 | 15672-98-7 | | | 3.04 |
| | | 3.25 | | 2.57 |
| 149109 | 59094-49-4 | | | 18.18 |
| 150279 | | 3.9 | | 0.62 |
| 150781 | 19802-61-0 | | | 3.78 |
| 150787 | | 5.6 | | 2.94 |
| 151117 | | 12.07 | | 0.85 |
| 151119 | | 6.62 | | 0.72 |
| 155015 | 73163-54-9 | 3.73 | | 2.19 |
| 157236 | | 3.4 | | 0.75 |
| 157306 | | 3.94 | | 1.77 |
| 157382 | 23886-57-9 | 9.04 | | 0.68 |
| 157487 | 34749-63-8 | 5.81 | | 2.53 |
| 157507 | | 3.33 | | 2.07 |
| 158091 | 30710-21-5 | 4.83 | | 1.66 |
| 158959 | | 4.01 | | 3.2 |
| 161089 | 19161-98-9 | 3.53 | | 1.67 |
| 162375 | | 3.07 | | 1.7 |
| 163547 | 40114-82-7 | 4.38 | | 3.27 |
| 163948 | 102-98-7 | | | 5.67 |
| 164212 | | 4.07 | | 2.04 |
| 165765 | 60696-76-6 | 4.44 | | 1.34 |
| 168745 | 15963-72-1 | 36.37 | | 0.39 |
| 170334 | | 4.45 | | 0.98 |
| 170444 | | 12.56 | | 0.66 |
| 170582 | 24596-38-1 | 4.44 | | 3.72 |
| 170589 | 17010-61-6 | 6.57 | | 3.81 |
| 170600 | 63019-82-9 | 3.46 | | 2.21 |
| 170633 | 17076-37-8 | 8.99 | | 5.12 |
| 170639 | 92296-17-8 | 5.38 | | 3.93 |
| 171129 | | 7.98 | | 5.1 |
| 171134 | | 3.68 | | 2.89 |
| 172879 | | 3.6 | | 1.11 |
| 173000 | | 3.68 | | 0.61 |
| 173710 | 57013-87-3 | 16.35 | | 0.83 |
| 174877 | | 3.29 | | 3.04 |
| 176145 | 108-07-6 | | | 3.81 |
| 176657 | | 4.64 | | 1.67 |
| 179739 | 27605-35-2 | 3.62 | | 0.98 |
| 179762 | | 18.35 | | 0.72 |
| 179764 | 25094-60-4 | | | |
| 179944 | 52494-54-9 | 6.1 | | 0.54 |
| 187755 | | 3.08 | | 1.12 |
| 193484 | | 22.72 | | 1.24 |
| 193713 | 52197-19-0 | 24.26 | | 0.55 |
| 194646 | | 6.24 | | 8.08 |
| 194807 | 77547-08-1 | 3.45 | | 1.72 |
| 201570 | | 3.02 | | 2.16 |
| 202491 | 18723-92-7 | 3.05 | | 0.5 |
| 202674 | 21227-23-6 | | | 4.67 |
| 203205 | 994-71-8 | | | 3.12 |
| 203373 | 20745-97-5 | 5.25 | | 10.51 |
| 203423 | 20745-98-6 | 3.09 | | 7.7 |
| 204163 | 56661-50-8 | 4.83 | | 2.44 |

TABLE 5-continued

| NSC #* | CAS_RN* | Activity 10 uM | Activity 5 uM | Activity 2.5 uM |
|---|---|---|---|---|
| 204246 | | 3.49 | | 1.92 |
| 204512 | 3837-55-6 | 4.16 | | 2.67 |
| 204514 | 3010-57-9 | 4.66 | | 3.6 |
| 204515 | 3789-77-3 | 5.31 | | 2.84 |
| 204548 | | 3.99 | | 2.82 |
| 204716 | 37666-22-1 | 3.01 | | 2.2 |
| 204750 | 29771-69-5 | 24.26 | | 3.53 |
| 204751 | | 4.76 | | 2.91 |
| 205530 | 73190-69-9 | 3.34 | | 3.08 |
| 205545 | | 4.54 | | 2.41 |
| 205548 | | 4.01 | | 2.94 |
| 205787 | | 4.39 | | 1.79 |
| 205789 | | 7.26 | | 3.99 |
| 212379 | 31191-41-0 | 4.4 | | 2.28 |
| 229344 | | 4.4 | | 1.28 |
| 234486 | | | | 10 |
| 236237 | | 57.44 | | 1.78 |
| 240577 | | 4.63 | | 2.68 |
| 258618 | | 3.2 | | 0.85 |
| 260514 | | 3.87 | | 1.94 |
| 262421 | 76609-51-3 | 107.79 | | 24.56 |
| 263517 | 3529-04-2 | 8.78 | | 1.39 |
| 268393 | 70380-40-4 | | | 0.71 |
| 270151 | | 3.16 | | 1.24 |
| 271272 | 71007-82-4 | 4.93 | | 2.76 |
| 271654 | | 18.07 | | 0.44 |
| 276293 | 40919-31-1 | | | 20.35 |
| 278352 | | | | 3.81 |
| 280894 | | | | 2.06 |
| 281986 | 3561-04-4 | 3.37 | | 3.11 |
| 286678 | 1124-50-1 | | | 1.72 |
| 287407 | | 36.2 | | 3.93 |
| 287413 | | 17.06 | | 0.68 |
| 291104 | 83379-23-1 | 3.83 | | 1.4 |
| 293939 | 36539-81-8 | 7.78 | | 1.54 |
| 295477 | | 9.07 | | 6.24 |
| 295679 | 75082-14-3 | 3.69 | | 0.78 |
| 297153 | 67675-62-1 | 4.39 | | 0.95 |
| 297154 | 67675-64-3 | 5.62 | | 1.24 |
| 297156 | | 5.15 | | 1.08 |
| 297621 | 59404-25-0 | | | 18.95 |
| 298153 | 64862-32-4 | 3.43 | | 3.67 |
| 299107 | | 279.99 | | 8.13 |
| 300554 | 56213-52-6 | 8.96 | | 0.48 |
| 300559 | | 4.71 | | 0.71 |
| 306697 | | 19.5 | | 1.77 |
| 309898 | | 13.68 | | 1.07 |
| 310008 | 4256-25-1 | 4.92 | | 1.66 |
| 310545 | | 6.96 | | 0.46 |
| 313162 | | 4.03 | | 1.07 |
| 315819 | 67507-09-9 | 13.17 | | 2.12 |
| 315820 | | 17.6 | | 1.5 |
| 316746 | | 6.11 | | 0.88 |
| 319697 | 75602-17-4 | | | 3.1 |
| 319699 | 75602-13-0 | 3.62 | | 0.29 |
| 322306 | | 63.6 | | 7.11 |
| 323938 | | 5.53 | | 0.99 |
| 324978 | | 9.9 | | 6.13 |
| 326059 | 82641-26-7 | 50.81 | | 7.62 |
| 326123 | 77921-36-9 | 12.9 | | 0.47 |
| 332426 | 71508-74-2 | 3.15 | | 2.37 |
| 337856 | | 25.44 | | 5.52 |
| 338631 | | 3.39 | | 1.12 |
| 339119 | 71568-54-2 | 4.42 | | 1.01 |
| 339567 | 39997-88-1 | 11.94 | | 1.94 |
| 340215 | | 3.11 | | 2.4 |
| 340302 | 36536-22-8 | 4.54 | | 3.29 |
| 343387 | | 3.33 | | 2.32 |
| 344506 | 71781-96-9 | 5.08 | | 0.69 |
| 349125 | | 13.75 | | 0.47 |
| 353255 | 7487-94-7 | | | 3.3 |
| 353738 | | | | 7.02 |
| 354087 | | 10.14 | | 2.65 |
| 354215 | 66646-01-3 | 4.14 | | 3.08 |
| 355167 | 79441-89-7 | 4.17 | | 3.09 |
| 359827 | | 6.27 | | 0.61 |
| 360648 | | 3.85 | | 1.88 |
| 361407 | | 3.7 | | 0.62 |
| 361597 | 13969-30-7 | 17.56 | | 0.32 |
| 361889 | 91327-55-8 | 12.01 | | 0.88 |
| 366233 | 88061-94-3 | 30.55 | | 17.26 |
| 367620 | | 16.04 | | 0.49 |
| 369110 | 73723-79-2 | 6.46 | | 1.84 |
| 369741 | 84405-20-9 | 6.34 | | 0.96 |
| 370463 | 52837-61-3 | 5.98 | | 4.76 |
| 370589 | | 39.54 | | 11.87 |
| 374924 | | 6.35 | | 2.1 |
| 374999 | | 15.92 | | 9.15 |
| 376265 | | 7.26 | | 2.72 |
| 376674 | | 16 | | 9.42 |
| 377376 | | 5.14 | | 0.96 |
| 377377 | | 34.93 | | 0.77 |
| 377378 | 87405-03-6 | 21.49 | | 0.87 |
| 377831 | 23047-95-2 | 3.79 | | 2.19 |
| 378135 | | 3.15 | | 1.75 |
| 379578 | | 27.15 | | 0.61 |
| 379665 | 67485-29-4 | 35.03 | | 1.08 |
| 380207 | 88000-87-7 | 6.39 | | 0.47 |
| 400077 | 888-71-1 | 3.14 | | 2.04 |
| 400538 | 2150-58-5 | 6.8 | | 0.57 |
| 400939 | 7467-29-0 | 3.56 | | 2.36 |
| 401234 | 7621-92-3 | 24.65 | | 1 |
| 401304 | 7469-11-6 | 43.11 | | 1.04 |
| 402193 | 1940-43-8 | 3.19 | | 0.56 |
| 402291 | | 4.43 | | 0.73 |
| 402592 | 2703-27-7 | 3.48 | | 2.25 |
| 402600 | 4638-48-6 | 4.82 | | 1.14 |
| 402785 | | | | 50.88 |
| 402826 | | 5.42 | | 0.85 |
| 402866 | | 26.02 | | 1.66 |
| 403440 | 7404-15-1 | 3.83 | | 1.41 |
| 403488 | 7502-07-0 | 4.41 | | 1.55 |
| 403534 | | 9.9 | | 7.33 |
| 405522 | 6043-40-9 | 3.69 | | 2.47 |
| 406018 | 7509-97-9 | 4.09 | | 1.51 |
| 406824 | 7497-80-5 | 4.25 | | 1.76 |
| 407396 | 426-79-9 | 4.74 | | 1.72 |
| 407658 | 7499-45-8 | 5.17 | | 1.57 |
| 408380 | | 4.36 | | 2.28 |
| 408383 | | 10.77 | | 0.84 |
| 408399 | | 3.42 | | 1.63 |
| 408711 | | 21.88 | | 1.47 |
| 408712 | | 21.65 | | 1.57 |
| 409777 | 19434-42-5 | 5.55 | | 20.85 |
| 601076 | | 3.17 | | 2.48 |
| 601994 | | 5.21 | | 3.42 |
| 602807 | | 3.12 | | 2.08 |
| 603554 | | 8.45 | | 0.35 |
| 603854 | | 4.19 | | 0.93 |
| 604861 | | 4.82 | | 0.8 |
| 604868 | | 5.36 | | 0.86 |
| 607085 | | 3.55 | | 2.21 |
| 608144 | | 112.47 | | 3.82 |
| 609211 | | 18.74 | | 5.68 |
| 609810 | | 4.69 | | 2.44 |
| 610051 | | 9.23 | | 1.52 |
| 615538 | | 4.53 | | 1.65 |
| 617570 | | 94.55 | | 2.36 |
| 617738 | | 7.65 | | 1.05 |
| 617743 | | 3.08 | | 1.47 |
| 618767 | | 6.58 | | 0.7 |
| 620291 | | 9.07 | | 8.39 |
| 620296 | | 3.13 | | 5.24 |
| 620852 | | 16.94 | | 4.79 |
| 621482 | | 5.15 | | 1.17 |
| 621504 | | | | 14.68 |
| 621792 | | 3.75 | | 1.27 |
| 621794 | | 6.6 | | 9.24 |
| 621795 | | | | 18.49 |
| 621796 | | | | 26.11 |
| 621797 | | 30.28 | | 25.08 |
| 621882 | | 3.1 | | 2.37 |
| 622579 | | 6.29 | | 2.99 |
| 622683 | | 3.82 | | 2.84 |

TABLE 5-continued

| NSC #* | CAS_RN* | Activity 10 uM | Activity 5 uM | Activity 2.5 uM |
|---|---|---|---|---|
| 623141 | | 4.84 | | 0.53 |
| 624851 | | | | 12.65 |
| 625863 | | 3.72 | | 3.75 |
| 627459 | | 7.21 | | 1.68 |
| 628577 | | 3.06 | | 1.45 |
| 628578 | | | | 3.53 |
| 628594 | | | | 3.94 |
| 631943 | | | | 6.31 |
| 631945 | | 5.72 | | 0.76 |
| 631946 | | | | 13.13 |
| 632134 | | 3.5 | | 1.26 |
| 633123 | | 3.88 | | 0.89 |
| 633268 | | 16.53 | | 3.96 |
| 633334 | | 28.14 | | 4.12 |
| 633346 | | 11.64 | | 8.05 |
| 633992 | | | | 13.09 |
| 633995 | | 11.56 | | 14.38 |
| 633997 | | 12.56 | | 17.11 |
| 634000 | | 12.96 | | 1.1 |
| 634004 | | 9.64 | | 3.7 |
| 634014 | | 12.92 | | 11.17 |
| 634157 | | 3.99 | | 0.8 |
| 634838 | | 30.9 | | 13.01 |
| 634842 | | 8.37 | | 1.71 |
| 635009 | | 10.57 | | 5.71 |
| 635022 | | 4.8 | | 0.96 |
| 635030 | | 71.33 | | 1.68 |
| 635072 | | 5.58 | | 1.59 |
| 638113 | | 3.17 | | 1.87 |
| 642485 | | 3.59 | | 1.93 |
| 643139 | | | | 1.53 |
| 643713 | | 4.87 | | 2.72 |
| 643762 | | 3.47 | | 1.99 |
| 644907 | | | | 4.97 |
| 645170 | | 5.1 | | 3 |
| 647131 | | 17.42 | | 1.96 |
| 647134 | | | | 3.1 |
| 647590 | | 3.22 | | 2.31 |
| 648479 | | 3.37 | | 2.55 |
| 650027 | | 4.42 | | 4.2 |
| 652047 | | 3.51 | | 1.15 |
| 652257 | | 8.74 | | 3.09 |
| 652531 | | 12.9 | | 0.71 |
| 652594 | | 14.89 | | 1.46 |
| 652890 | | 7.57 | | 2.23 |
| 652917 | | 3.31 | | 2.33 |
| 652924 | | 3.58 | | 1.78 |
| | | | | 7.29 |
| 655141 | | 3.91 | | 2.18 |
| 656075 | | 7.97 | | 2.33 |
| 656076 | | 17.27 | | 4.6 |
| 656711 | | 6.66 | | 0.59 |
| 657189 | | 3.16 | | 2.65 |
| 657424 | | 3.36 | | 1.17 |
| 658163 | | 4.46 | | 2.63 |
| 658355 | | 8.48 | | 0.5 |
| 658358 | | 20.35 | | 0.4 |
| 658830 | | 4.21 | | 0.48 |
| 659608 | | 3.07 | | 1.34 |
| 661223 | | 11.8 | | 1.05 |
| 661225 | | 25.16 | | 1.76 |
| 662875 | | 40.72 | | 10.55 |
| 664259 | | 4.24 | | 2.76 |
| 665512 | | 15.46 | | 0.47 |
| 665702 | | 3.38 | | 1.79 |
| 665910 | | 4.69 | | 0.72 |
| 666131 | | 8.72 | | 4.12 |
| 666356 | | 30.26 | | 2.43 |
| 667223 | | 6.01 | | 0.42 |
| 667226 | | 4.79 | | 0.34 |
| 667463 | | 3.45 | | 3.13 |
| 667472 | | 9.48 | | 0.35 |
| 667875 | | 7.27 | | 4.59 |
| 667885 | | 15.62 | | 8.61 |
| 668262 | | 3.33 | | 0.78 |
| 668297 | | 37.53 | | 10.51 |
| 668298 | | 30.06 | | 11.99 |
| 668332 | | 63.38 | | 27.24 |
| 668484 | | 3.57 | | 1.59 |
| 668494 | | 13.68 | | 3.76 |
| 668605 | | 3.17 | | 0.8 |
| 670779 | | 6.67 | | 2.57 |
| 670788 | | 4.08 | | 6.58 |
| 670961 | | 4.46 | | 7.92 |
| 670965 | | 23.32 | | 50.7 |
| 671441 | | | | 5.35 |
| 671442 | | 7.03 | | 9.59 |
| 671896 | | 4.31 | | 0.85 |
| 673797 | | 4.7 | | 2.54 |
| 674469 | | 23.82 | | 1.37 |
| 678036 | | 12.77 | | 0.85 |
| 680834 | | 4.25 | | 0.76 |
| 682512 | | 10.02 | | 0.57 |
| 687849 | | 12.02 | | 0.88 |
| 690404 | | 3.03 | | 1.46 |
| 690734 | | 10.02 | | 0.48 |
| 186257 | 52197-26-9 | 59.966 | 49.982 | |
| 185066 | | 20.339 | 44.91067 | |
| 118026 | 17154-55-1 | 40.338 | 37.512 | |
| 150311 | | 39.7 | 36.66967 | |
| 75382 | 15091-30-2 | 21.055 | 33.125 | |
| 273747 | 64724-84-1 | 26.646 | 29.296 | |
| 174794 | 52197-13-4 | 33.869 | 24.857 | |
| 150320 | | 16.4 | 19.9 | |
| 165688 | 22933-76-2 | 14.6965 | 17.91033 | |
| 94582 | | 17.458 | 17.82567 | |
| 65486 | 3820-71-1 | 20.8755 | 17.496 | |
| 177407 | 58885-11-3 | 21.876 | 16.53 | |
| 135331 | | 31.606 | 15.388 | |
| 99047 | 17490-47-0 | 13.186 | 14.82433 | |
| 148342 | | 19.7555 | 14.51333 | |
| 101539 | | 6.8175 | 14.033 | |
| 327371 | 71156-12-2 | 22.247 | 13.29167 | |
| 55869 | 6947-89-3 | 13.613 | 13.23667 | |
| 83318 | 88210-37-1 | 14.6225 | 12.02733 | |
| 88001 | | 21.4655 | 12.00033 | |
| 58338 | 6627-15-2 | 17.599 | 11.604 | |
| 54905 | | 16.011 | 11.55767 | |
| 167334 | 38633-42-0 | 12.373 | 11.387 | |
| 72005 | 101-20-2 | 16.9235 | 11.24533 | |
| 343385 | | 8.3265 | 11.19733 | |
| 93360 | 485-72-3 | 10.283 | 11.07867 | |
| 98409 | 10432-50-5 | 25.659 | 10.997 | |
| 152111 | 16436-29-6 | 10.391 | 10.85133 | |
| 79681 | | 5.9 | 10.5 | |
| 83089 | 2428-35-5 | 5.1265 | 10.155 | |
| 209832 | | 4.7795 | 9.509333 | |
| 89864 | | 10.1 | 9.4 | |
| 133463 | 1166-52-5 | 4.63 | 8.8 | |
| 135741 | 25201-67-6 | 7.226 | 8.604667 | |
| 321198 | | 9.062 | 8.313333 | |
| 73118 | 4273-92-1 | 10.008 | 8.006333 | |
| 156572 | | 7.9345 | 7.884 | |
| 82910 | 2785-54-8 | 12.4425 | 7.653667 | |
| 81523 | | 8.879 | 7.525667 | |
| 328479 | 2867-96-1 | 7.342 | 7.501667 | |
| 68292 | | 18.3 | 7.2 | |
| 115157 | | 40.7 | 7.1 | |
| 135744 | 32251-73-3 | 21.9 | 7 | |
| 693037 | | 8.088 | 6.794333 | |
| 100239 | 54980-33-5 | 7.6705 | 6.748 | |
| 214041 | | 8.374 | 6.705333 | |
| 276393 | 64724-83-0 | 8.706 | 6.644333 | |
| 87086 | | 5.461 | 6.572333 | |
| 90777 | 57532-86-2 | 8.406 | 6.553 | |
| 104498 | | 8.4845 | 6.367333 | |
| 240870 | 27128-58-1 | 7.2395 | 6.351667 | |
| 63346 | 21970-53-6 | 6.8235 | 6.234333 | |
| 240575 | | 7.0215 | 6.229667 | |
| 59070 | | 7.423 | 6.227 | |
| 337757 | 22295-55-2 | 5.978 | 6.204667 | |
| 69625 | 13208-31-6 | 4.8565 | 6.200667 | |
| 109156 | 7204-43-5 | 9.1 | 6.2 | |
| 367416 | 74396-45-5 | 7.3545 | 6.047333 | |

TABLE 5-continued

| NSC #* | CAS_RN* | Activity 10 uM | Activity 5 uM | Activity 2.5 uM |
|---|---|---|---|---|
| 227290 | 61471-39-4 | 6.8065 | 5.934667 | |
| 268776 | | 5.5035 | 5.767 | |
| 71689 | | 7.139 | 5.723667 | |
| 69510 | | 10.9 | 5.6 | |
| 74740 | 7533-73-5 | 4.1 | 5.6 | |
| 326181 | 67829-21-4 | 7.027 | 5.584333 | |
| 240576 | | 6.2885 | 5.469667 | |
| 57019 | 2872-52-8 | 5.441 | 5.388 | |
| 204668 | | 4.923 | 5.386 | |
| 346212 | 72499-61-7 | 5.7595 | 5.376 | |
| 214004 | | 6.0655 | 5.299333 | |
| 87323 | 30041-69-1 | 6.0905 | 5.277333 | |
| 204386 | | 6.0225 | 5.251667 | |
| 214029 | | 6.8665 | 5.244667 | |
| 104959 | 6824-07-3 | 5.474 | 5.189667 | |
| 369061 | 93745-54-1 | 6.3 | 5.136667 | |
| 321197 | | 5.0845 | 5.014333 | |
| 694092 | | 5.898 | 4.958 | |
| 687753 | | 6.931 | 4.921667 | |
| 86430 | 2428-30-0 | 6.063 | 4.871333 | |
| 689962 | | 7.987 | 4.784333 | |
| 101082 | 5784-95-2 | 5.896 | 4.772333 | |
| 292796 | 52053-74-4 | 5.6 | 4.759333 | |
| 136768 | 28069-65-0 | 3.271 | 4.667667 | |
| 213848 | | 3.5355 | 4.586 | |
| 691256 | | 5.7865 | 4.563 | |
| 338462 | 7560-35-2 | 6.4125 | 4.540333 | |
| 222612 | | 2.88 | 4.521333 | |
| 186948 | | 4.4425 | 4.507333 | |
| 230359 | 72648-43-2 | 8.3955 | 4.464667 | |
| 76429 | | 5.2405 | 4.409333 | |
| 356111 | 90760-42-2 | 3.2 | 4.4 | |
| 159209 | 612-81-7 | 8.5 | 4.3 | |
| 54895 | 74305-79-6 | 4.975 | 4.287667 | |
| 332423 | 71536-10-2 | 5.4265 | 4.287 | |
| 347204 | 72499-57-1 | 6.6455 | 4.245667 | |
| 343386 | | 5.4775 | 4.235333 | |
| 55240 | 6951-36-6 | 5.2 | 4.2 | |
| 213710 | | 5.091 | 4.183 | |
| 78949 | | 7.7 | 4.1 | |
| 231980 | 31392-73-1 | 3.8 | 4.1 | |
| 332543 | 88324-30-5 | 5.182 | 4.082667 | |
| 119026 | 90111-22-1 | 12.6 | 4 | |
| 115724 | 21299-50-3 | 7.3 | 4 | |
| 691255 | | 5.5705 | 3.963 | |
| 86544 | 637-47-8 | 4.845 | 3.953667 | |
| 136889 | | 16.7 | 3.9 | |
| 109535 | | 6.3 | 3.9 | |
| 691258 | | 3.904 | 3.891333 | |
| 290436 | 53655-17-7 | 20.4 | 3.8 | |
| 327414 | | 6.977 | 3.793333 | |
| 91885 | 2440-22-4 | 4.473 | 3.742333 | |
| 191390 | 73108-79-9 | 4.295 | 3.709667 | |
| 292795 | 35299-76-4 | 4.66 | 3.69 | |
| 202060 | 64985-95-1 | 5.049 | 3.629667 | |
| 191395 | 42174-34-5 | 7.0185 | 3.608667 | |
| 240724 | | 4.257 | 3.594 | |
| 69580 | 6959-97-3 | 6.4 | 3.5 | |
| 149581 | 41962-27-0 | 4.3 | 3.5 | |
| 338119 | 6443-79-4 | 5.6885 | 3.434667 | |
| 55237 | 6624-17-5 | 6.6 | 3.4 | |
| 56345 | | 3.64 | 3.4 | |
| 82278 | | 3.1525 | 3.287667 | |
| 72035 | 87-22-9 | 3.8265 | 3.275 | |
| 186256 | 52197-25-8 | 3.71 | 3.212333 | |
| 159569 | | 5.804 | 3.210333 | |
| 135745 | 32251-74-4 | 6.5 | 3.2 | |
| 122241 | 20286-82-2 | 5 | 3.2 | |
| 94585 | | 3.525 | 3.148333 | |
| 347816 | 72499-65-1 | 3.5245 | 3.142667 | |
| 85646 | | 4.18 | 3.126667 | |
| 75971 | | 3.3355 | 3.111333 | |
| 204931 | 93008-58-3 | 3.539 | 3.100333 | |
| 67112 | | 16.3 | 3.1 | |
| 106344 | 61653-37-0 | 4.1 | 3.1 | |
| 103755 | 16504-14-6 | 3.394 | 3.089667 | |
| 99696 | 10499-10-2 | 3.4275 | 3.031333 | |
| 191346 | | 4.4055 | 3.017667 | |
| 61369 | 5137-55-3 | 4.4 | 3 | |
| 72266 | 7149-62-4 | 3.233 | 2.946333 | |
| 71676 | 786-50-5 | 4.1015 | 2.921667 | |
| 71690 | 34243-33-9 | 3.4315 | 2.888667 | |
| 112668 | 13228-40-5 | 3.3905 | 2.854333 | |
| 61626 | 2508-13-6 | 3.1685 | 2.793 | |
| 101544 | 16722-41-1 | 3.1185 | 2.767 | |
| 298243 | 64273-27-4 | 3.327 | 2.747 | |
| 170680 | 1123-51-9 | 6.8 | 2.7 | |
| 93861 | | 3.171 | 2.622 | |
| 71968 | 7779-17-1 | 3.5615 | 2.615 | |
| 161504 | 22974-38-5 | 5.3 | 2.6 | |
| 106343 | 5302-41-0 | 4.1 | 2.6 | |
| 103842 | 27702-26-7 | 3.3 | 2.6 | |
| 292587 | 239-58-7 | 3.294 | 2.576667 | |
| 343979 | | 3.1255 | 2.571333 | |
| 369331 | 84859-31-4 | 2.7605 | 2.533 | |
| 136886 | | 28.5 | 2.5 | |
| 230415 | 2829-28-9 | 3.3005 | 2.468333 | |
| 119688 | | 3.9 | 2.45 | |
| 123507 | 3568-90-9 | 10.5 | 2.41 | |
| 366583 | | 3.134 | 2.409 | |
| 356110 | 84633-99-8 | 3.9 | 2.4 | |
| 101484 | 19749-34-9 | 3.4 | 2.4 | |
| 120440 | 30251-61-7 | 3.8 | 2.3 | |
| 168465 | 50286-86-7 | 6 | 2.2 | |
| 96306 | | 5.7 | 2.2 | |
| 163454 | 10173-53-2 | 3.5 | 2.2 | |
| 139221 | 5064-89-1 | 9 | 2.1 | |
| 74568 | | 4.8 | 2.1 | |
| 85573 | | 3.1 | 2.1 | |
| 96375 | | 5.9 | 2 | |
| 94029 | 5659-13-2 | 3.2135 | 1.933667 | |
| 116685 | 13432-87-6 | 4.5 | 1.9 | |
| 59465 | 7400-23-9 | 6.8 | 1.8 | |
| 106208 | 74037-43-7 | 4.3 | 1.8 | |
| 146007 | | 3.4 | 1.8 | |
| 55879 | 6947-93-9 | 3.8 | 1.7 | |
| 74566 | 13595-34-1 | 3.7 | 1.7 | |
| 172656 | 53219-25-3 | 3.9 | 1.6 | |
| 208394 | | 13.4 | 1.5 | |
| 112369 | | 3.1 | 1.4 | |
| 144126 | | 7.3 | 1.3 | |
| 106909 | 22966-82-1 | 3.4 | 1.2 | |
| 55867 | 6947-88-2 | 3.2 | 1.1 | |
| 11235 | 2390-54-7 | 27.11026 | | 7.299852 |
| 163482 | | 3.207313 | | 1.587711 |
| 380207 | 88000-87-7 | 3.061186 | | 0.36152 |
| 401162 | 64693-19-2 | 7.084166 | | 0.378361 |
| 527347 | 7385-99-1 | 5.590928 | | 2.550671 |
| 622579 | | 10.08266 | | 0.38273 |
| 643139 | | 7.511198 | | 0.181398 |
| 653438 | | 12.31648 | | 0.754953 |
| 658354 | | 6.608676 | | 0.23793 |
| 658916 | | 3.180133 | | 2.046552 |
| 667223 | | 8.726255 | | 0.154498 |
| 670779 | | 8.739112 | | 2.72082 |
| 670961 | | 14.2083 | | 3.272683 |
| 670965 | | 25.3088 | | 44.32161 |
| 670969 | | 3.643563 | | 1.549795 |

*Entering either the NSC number (NSC followed by the number) of a compound or the CAS number of the compound in the PubChem compound database will bring up the chemical structure and other publicly available information about the compound.

TABLE 6

Effect of anti-cancer agents (20 μM) on F-luc/R-luc ratio in the ternary complex assay.

| Agent | Mechanism of Action | Relative F-luc/R-luc Ratio (+/− SEM) |
|---|---|---|
| Camptothecin | Topoisomerase inhibitor | 1.3 + 0.3 |
| Colchicine | Inhibitor of tubulin polymerization | 1.2 + 0.3 |
| Threo-1-phenyl | Glucolipid synthase inhibitor | 1.5 + 0.4 |
| Mitomycin C | Alkylating agent, DNA synthesis inhibitor | 0.9 + 0.3 |
| H-89 | PK-A inhibitor | 1.5 + 0.6 |
| 5-fluorouracil | Thymidilate synthase inhibitor | 1 + 0.2 |
| Epigallocatechin | Laminin Receptor 1 activation | |
| 3-isobutyl-1-methylxanthine | Phosphodiesterase inhibitor | 1.1 + 0.2 |
| Dilthiazem | Ca++ channel blocker | 1.4 + 0.4 |
| Amiloride | Na+ channel blocker | 1.1 + 0.3 |
| Okadaic acid | Protein Phosphatase 1 inhibitor | 1 + 0.3 |
| Somatostatin | Inhibitor of growth hormone secretion | 0.9 + 0.2 |
| Glycyl-1-histidyl acetate | Not known | 1 + 0.1 |
| Etoposite | Topoisomerase I inhibitor | 1 + 0.2 |
| CLT | Ca++ store depletion | 6 + 1.1 |

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference herein in their entirety for all purposes to the same extent as if each individual publication or patent application was specifically indicated to be so incorporated by reference.

What is claimed is:
1. A compound of formula
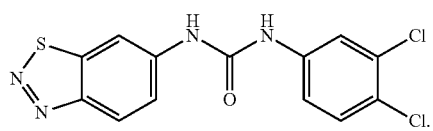 [SMILES: O=C(Nc1ccc(Cl)c(Cl)c1)Nc1ccc2nnsc2c1]

UNITED STATES PATENT AND TRADEMARK OFFICE
CERTIFICATE OF CORRECTION

PATENT NO. : 9,932,300 B2
APPLICATION NO. : 15/216057
DATED : April 3, 2018
INVENTOR(S) : Aktas et al.

It is certified that error appears in the above-identified patent and that said Letters Patent is hereby corrected as shown below:

In the Specification

Column 1, under STATEMENT OF GOVERNMENT INTERESTS, Line 21-23:
Please delete "This invention was made with government support under 5 U19 CA87427 awarded by the National Institutes of Health. The government has certain rights in the invention." and insert --This invention was made with government support under CA087427 awarded by National Institutes of Health (NIH). The government has certain rights in this invention.--

Signed and Sealed this
Twenty-seventh Day of September, 2022

Katherine Kelly Vidal
*Director of the United States Patent and Trademark Office*